US010012627B2

(12) United States Patent
Wolf et al.

(10) Patent No.: US 10,012,627 B2
(45) Date of Patent: Jul. 3, 2018

(54) DETERMINING STEREOISOMERIC EXCESS, CONCENTRATION AND ABSOLUTE CONFIGURATION

(71) Applicant: GEORGETOWN UNIVERSITY, Washington, DC (US)

(72) Inventors: Christian Wolf, Arlington, VA (US); Peng Zhang, Arlington, VA (US)

(73) Assignee: Georgetown University, Washington, DC (US)

(*) Notice: Subject to any disclaimer, the term of this patent is extended or adjusted under 35 U.S.C. 154(b) by 0 days.

(21) Appl. No.: 14/777,264

(22) PCT Filed: Mar. 15, 2014

(86) PCT No.: PCT/US2014/029982
§ 371 (c)(1),
(2) Date: Sep. 15, 2015

(87) PCT Pub. No.: WO2014/145251
PCT Pub. Date: Sep. 18, 2014

(65) Prior Publication Data
US 2016/0011156 A1 Jan. 14, 2016

Related U.S. Application Data

(60) Provisional application No. 61/903,360, filed on Nov. 12, 2013, provisional application No. 61/902,204, filed on Nov. 9, 2013, provisional application No. 61/791,832, filed on Mar. 15, 2013.

(51) Int. Cl.
*G01N 31/10* (2006.01)
*G01N 21/19* (2006.01)

(52) U.S. Cl.
CPC ............. *G01N 31/10* (2013.01); *G01N 21/19* (2013.01)

(58) Field of Classification Search
CPC ................................ G01N 31/10; G01N 21/19
See application file for complete search history.

(56) References Cited

U.S. PATENT DOCUMENTS

| | | | |
|---|---|---|---|
| 5,763,679 | A | 6/1998 | Nicholson et al. |
| 6,875,877 | B2 | 4/2005 | Li et al. |
| 7,045,360 | B2 | 5/2006 | Shair et al. |
| 7,332,343 | B2 | 2/2008 | Anslyn et al. |
| 7,648,841 | B2 | 1/2010 | Inoue et al. |
| 7,670,847 | B2 | 3/2010 | Anslyn et al. |
| 7,736,902 | B2 | 6/2010 | Inoue et al. |
| 8,189,188 | B2 | 5/2012 | Busch et al. |
| 2011/0045598 | A1 | 2/2011 | Busch et al. |

OTHER PUBLICATIONS

Nieto et al. Rapid enantiomeric excess and concentration determination using simple racemic metal complexes. Organic Letters 2008, vol. 10., No. 2, pp. 5167-5170.*
Aikawa & Mikami, "Asymmetric Catalysis Based on Tropos Ligands," Chem. Commun. 48:11050-69 (2012).
Bull et al., "Exploiting the Reversible Covalent Bonding of Boronic Acids: Recognition, Sensing, and Assembly," Acc. Chem. Res. 46(2):312-26 (2013).
Gajewy et al., "Asymmetric Hydrosilylation of Ketones Catalyzed by Complexes Formed from Trans-Diaminocyclohexane-Based Diamines and Diethylzinc," Monatsh Chem. 143:1045-54 (2012).
Gajewy et al., "Mechanism and Enantioselectivity of [Zinc(diamine)(diol)]-Catalyzed Asymmetric Hydrosilylation of Ketones: DFT, NMR and ECD Studies," Eur. J. Org. Chem. 2013(2):307-18 (2013).
Iwaniuk & Wolf, "Chiroptical Sensing of Citronellal: Systematic Development of a Stereodynamic Probe Using the Concept of Isostericity," Chem. Commun. 48:11226-28 (2012).
Iwaniuk et al., "Enantioselective Sensing of Chiral Amino Alcohols with a Stereodynamic Arylacetylene-Based Probe," Chirality 24:584-89 (2012).
Joyce et al., "Enantio- and Chemoselective Differentiation of Protected Alpha-Amino Acids and Beta-Homoamino Acids with a Single Copper Host," Chemistry 18(26):8064-69 (2012).
Li et al., "Absolute Configuration for 1,n-Glycols: A Nonempirical Approach to Long-Range Stereochemical Determination," J. Am. Chem. Soc. 134:9026-29 (2012).
Wolf & Bentley, "Chirality Sensing Using Stereodynamic Probes with Distinct Electronic Circular Dichroism Output," Chem. Soc. Rev. 42:5408-24 (2013).
You et al., "An Exciton-Coupled Circular Dichroism Protocol for the Determination of Identity, Chirality, and Enantiomeric Excess of Chiral Secondary Alcohols," J. Am. Chem Soc. 134:7117-25 (2012).
Zhang & Wolf, "Sensing of the Concentration and Enantiomeric Excess of Chiral Compounds with Tropos Ligand Derived Metal Complexes," Chem. Commun. 49:7010-12 (2013).
Ghosn & Wolf, "Chiral Amplification with a Stereodynamic Triaryl Probe: Assignment of the Absolute Configuration and Enantiomeric Excess of Amino Alcohols," J. Am. Chem. Soc.131:16360-61 (2009).
International Search Report and Written Opinion for corresponding International Application No. PCT/US14/29982 (dated Aug. 12, 2014).
Mikami & Aikawa, "Dynamic Asymmetric Catalysis by Diphenylphosphinoferrocene (DPPF)-Nickel Complexes Through Control of Axial Chirality by Chiral Diamines," Org. Lett. 4(1):99-101 (2002).
Nieto et al., "A Facile CD Protocol for Rapid Determination of Enantiomeric Excess and Concentration of Chiral Primary Amines," Chemistry 16(1):227-32 (2010).
Nieto et al., "Rapid Enantiomeric Excess and Concentration Determination Using Simple Racemic Metal Complexes," Org. Lett. 10(22):5167-70 (2008).
Yu et al., "Simultaneous Determination of Both the Enantiomeric Composition and Concentration of a Chiral Substrate with One Fluorescent Sensor," J. Am. Chem.Soc. 134(50):20282-85 (2012).
Meca et al., "Racemization Barriers of 1,1'-Binaphthyl and 1,1'-Binapthalene-2,2'-Diol: A DFT Study," J. Org. Chem. 68:5677-80 (2003).

(Continued)

*Primary Examiner* — Shafiqul Haq
(74) *Attorney, Agent, or Firm* — LeClairRyan PLLC

(57) ABSTRACT

The present invention is directed to analytical methods for determining the concentration, and/or stereoisomeric excess, and/or absolute configuration of chiral analytes in a sample.

14 Claims, 53 Drawing Sheets

(56) References Cited

OTHER PUBLICATIONS

Mikami et al., "Tropos or Atropos? That Is the Question!," Synlett 10:1561-78 (2002).

Miyashita et al., "Synthesis of 2,2'-Bis(Diphenylphosphino)-1,1'-Binaphthyl (BINAP), an Atropisomeric Chiral Bis.(Triaryl)Phosphine, and Its Use in the Rhodium(I)-Catalyzed Asymmetric Hydrogenation of α-(Acylamino)Acrylic Acids," J. Am. Chem. Soc. 102:7932-34 (1980).

\* cited by examiner

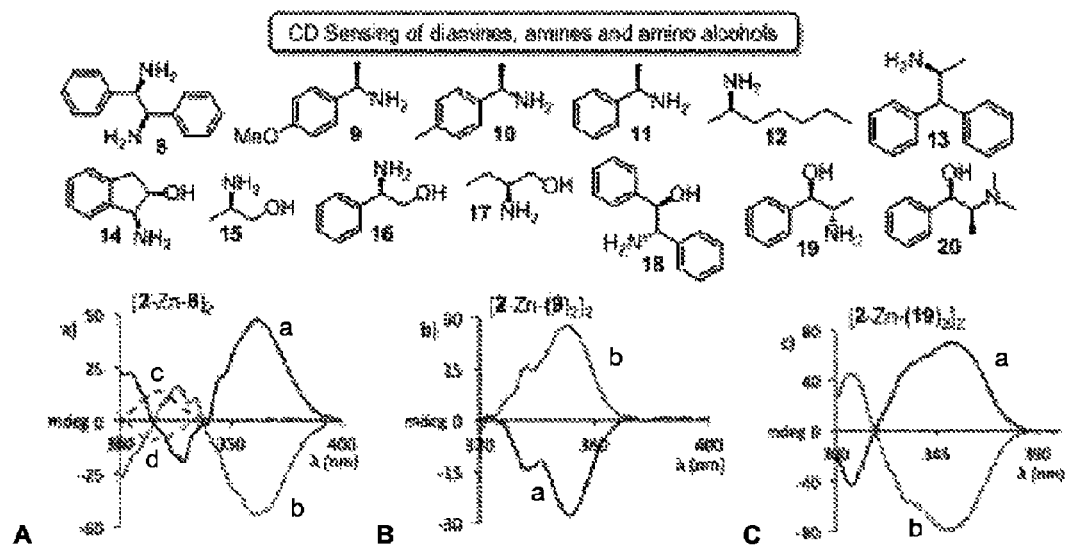
Figures 97A–C
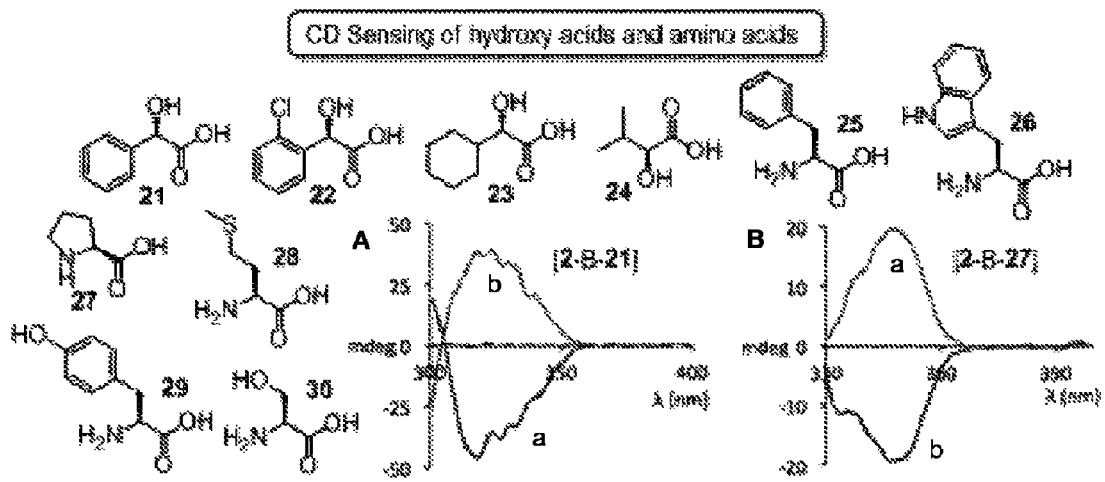
Figures 98A–B

DETERMINING STEREOISOMERIC EXCESS, CONCENTRATION AND ABSOLUTE CONFIGURATION

This application is a national stage application under 35 U.S.C. § 371 of PCT Application No. PCT/US2014/029982, filed Mar. 15, 2014, which claims the priority benefit of of U.S. Provisional Patent Application Ser. No. 61/791,832, filed Mar. 15, 2013; U.S. Provisional Patent Application Ser. No. 61/902,204, filed Nov. 9, 2013; and U.S. Provisional Patent Application Ser. No. 61/903,360, filed Nov. 12, 2013, each of which is hereby incorporated by reference in its entirety.

This invention was made with U.S. Government support under Grant Nos. CHE 1213019 and REU-1156788 awarded by the National Science Foundation. The U.S. Government has certain rights in this invention.

FIELD OF THE INVENTION

The present invention relates to evaluating the concentration, and/or stereoisomeric excess, and/or absolute configuration of chiral analytes in a sample.

BACKGROUND OF THE INVENTION

Chirality plays an essential role in nature and throughout the chemical sciences. Enantioselective synthesis and analysis of chiral compounds have become central aspects of drug discovery, material sciences, and other rapidly expanding research areas. The importance of chiral compounds in the pharmaceutical industry and other fields has stimulated the development of numerous asymmetric catalysts and reaction strategies (14 GAWLEY & AUBÉ, Principles of Asymmetric Synthesis, in TETRAHEDRON ORGANIC CHEMISTRY SERIES (J. E. Baldwin & P. D. Magnus eds., 1996); CHRISTIAN WOLF, DYNAMIC STEREOCHEMISTRY OF CHIRAL COMPOUNDS 180-398 (2008)). Optimization efforts typically entail elaborate chiral ligand modifications to fine-tune the catalyst in addition to conventional screening of a wide range of reaction parameters.

The introduction of tropos ligands such as biphenol phosphite (Reetz & Neugebauer, *Angew. Chem. Int. Ed.* 38:179-81 (1999); Blackmond et al., *Angew. Chem. Int. Ed.* 38:2196-99 (1999); Reetz & Li, *Angew. Chem. Int. Ed.* 44:2959-62 (2005)), DPPF (Mikami & Aikawa, *Org. Lett.* 4:99-101 (2002)), BIPHEP (Ohkuma et al., *J. Am. Chem. Soc.* 120:1086-87 (1998); Mikami et al., *Angew. Chem. Int. Ed.* 38:495-97 (1999); Becker et al., *J. Am. Chem. Soc.* 123:9478-79 (2001); Aikawa & Mikami, *Angew. Chem. Int. Ed.* 42:5455-58 (2003); Aikawa & Mikami, *Angew. Chem. Int. Ed.* 42:5458-61 (2003); Mikami et al., *Angew. Chem. Int. Ed.* 44:7257-60 (2005); Aikawa et al., *Angew. Chem. Int. Ed.* 48:6073-77 (2009)), and BIPHOS (Tissot et al., *Angew. Chem. Int. Ed.* 40:1076-78 (2001)) to asymmetric catalysis has greatly facilitated these efforts and led to a variety of highly effective reactions (Aikawa & Mikami, Review, *Chem. Commun.* 48:11050-69 (2012)) (selected examples of tropos ligands used in asymmetric catalysis are shown below).

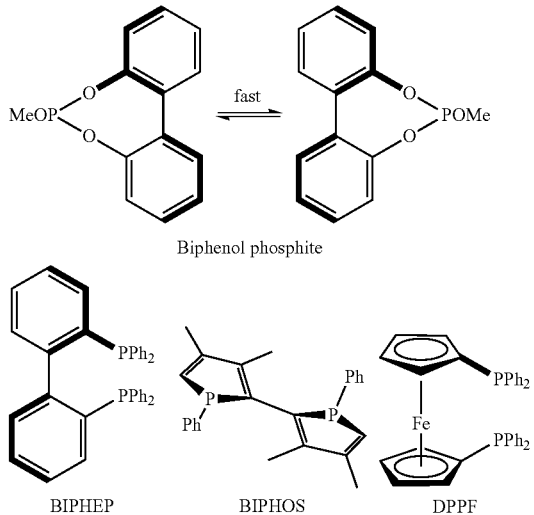

An important feature of tropos ligands is that they exist as a mixture of rapidly interconverting rotamers at room temperature (CHRISTIAN WOLF, DYNAMIC STEREOCHEMISTRY OF CHIRAL COMPOUNDS 292 (2008)). In many cases, addition of an enantiopure diamine or another activator to a metal complex carrying a tropos ligand, for example [(DPPF)Pd(II)], affords chiral catalysts that give exceptional yields and ee's in hydrogenation, Diels-Alder, ene, and other reactions. The presence of a stereodynamic ligand in the coordination sphere of a chiral metal complex often favors the population of a distinct conformation or configuration, and this chiral amplification process can ultimately enhance the asymmetric induction process (CHRISTIAN WOLF, DYNAMIC STEREOCHEMISTRY OF CHIRAL COMPOUNDS 180-398 (2008)). Because many tropos ligands are readily available and inexpensive compared to their nonracemizable enantiopure analogues, the optimization of the ee of a catalytic reaction by screening of tropos additives is economically attractive and has been adapted by many laboratories.

Cobalt complexes carrying chiral N,N'-bis(salicylidene) ethylenediamine (salen) ligands have also been used very successfully as polymerization catalysts (Nakano et al., *Angew. Chem. Int. Ed.* 50:4868-71 (2011); Jeon et al., *Dalton Trans.* 42:9245-54 (2013); Wu et al., *Macromolecules* 46:2128-33 (2013)) and in asymmetric catalytic reactions (Canali & Sherrington, *Chem. Soc. Rev.* 28:85-93 (1999); Baleizão & Garcia, *Chem. Rev.* 106:3987-4043 (2006); Decortes et al., *Angew. Chem. Int. Ed.* 49:9822-37 (2010)). Impressive results have been reported by Jacobsen and others with epoxide desymmetrizations (Birrell & Jacobsen, *Org. Lett.* 78:2895-97 (2013)), and hydrolytic (Tokunaga et al., *Science* 277:936-38 (1997); Schaus et al., *J. Am. Chem. Soc.* 124:1307-15 (2002); Liu et al., *J. Am. Chem. Soc.* 133:14260-63 (2011); Ford et al., *J. Am. Chem. Soc.* 135:15595-608 (2013)) or aminolytic (Kumar et al., *J. Org. Chem.* 78:9076-84 (2013)) kinetic resolutions of epoxides (Bredihhina et al., *J. Org. Chem.* 78:2379-85 (2013)). The general usefulness of chiral (salen)cobalt complexes in asymmetric catalysis has inspired several enantioselective recognition (Mizuno et al., *Tetrahedron* 55:9455-68 (1999)) and resolution studies (Fujii et al., *Bull. Chem. Soc. Jpn.* 54:2029-38 (1981); Fujii et al., *J. Chem. Soc. Chem. Commun.* 7:415-17 (1985)). For example, it has been shown that the lipophilic cobalt(III) complex derived from the $C_2$-symmetric salen 3 (see Example 26 for structure), which is a very effective catalyst in hydrolytic kinetic resolutions of terminal epoxides, can be used for practical separation of racemic N-benzyl α-amino acids via liquid-liquid extraction (Dzygiel et al., *Eur. J. Org. Chem.* 1253-64 (2008)). It has also been demonstrated that the cobalt(III) complex of the asymmetric ligand 4 (see Example 26 for structure) has potential for enantioselective differentiation of unprotected chiral amino alcohols (Kim et al., *J. Am. Chem. Soc.* 127:16776-77 (2005)).

The advance of combinatorial methods and automated synthesis allows the production of large numbers of chiral samples literally overnight. The steadily increasing efficiency in asymmetric synthesis has shifted focus toward the development of time efficient optical techniques with potential for high-throughput screening (Leung et al., *Chem. Soc. Rev.* 41:448 (2012)). In contrast to the advance of asymmetric synthesis, which is partly due to the widespread use of combinatorial methods that yield large numbers of chiral samples overnight, the analysis of the enantiomeric composition of chiral products is typically time-consuming and delays the discovery progress (Leung et al., *Chem. Soc. Rev.* 41:448-79 (2012)). Several groups have begun to address this bottleneck with the development of optical methods based on fluorescence (Lee & Lin, *J. Am. Chem. Soc.* 124:4554-55 (2002); Lin et al., *J. Am. Chem. Soc.* 124:2088-89 (2002); Mei & Wolf, *Chem. Commun.* 2078-79 (2004); Zhao et al., *Angew. Chem. Int. Ed.* 43:3461-64 (2004); Mei & Wolf, *J. Am. Chem. Soc.* 126:14736-37 (2004); Li et al., *Angew. Chem. Int. Ed.* 44:1690-93 (2005); Tumambac & Wolf, *Org. Lett.* 7:4045-48 (2005); Mei et al., *J. Org. Chem.* 71:2854-61 (2006); Mei & Wolf, *Tetrahedron Lett.* 47:7901-04 (2006); Wolf et al., *Chem. Commun.* 40:4242-44 (2006); Liu et al., *J. Org. Chem.* 73:4267-70 (2008); Yu & Pu, *J. Am. Chem. Soc.* 132:17698-700 (2010); Wu et al., *Chem. Eur. J.* 17:7632-44 (2011); Yang et al., *Org. Lett.* 13:3510-13 (2011); He et al., *Chem. Commun.* 47:11641-43 (2011); Wanderley et al., *J. Am. Chem. Soc.* 134:9050-53 (2012); Pu, Review, *Chem. Rev.* 104:1687-716 (2004)), UV absorbance (Zhu & Anslyn, *J. Am. Chem. Soc.* 126:3676-77 (2004); Mei & Wolf, *J. Am. Chem. Soc.* 128:13326-27 (2006); Leung et al., *J. Am. Chem. Soc.* 130:12318-27 (2008); Leung & Anslyn, *J. Am. Chem. Soc.* 130:12328-33 (2008); Iwaniuk et al., *J. Org. Chem.* 77:5203-08 (2012)), and circular dichroism (Superchi et al., *Angew. Chem. Int. Ed.* 40:451-54 (2001); Kurtan et al., *J. Am. Chem. Soc.* 123:5974-82 (2001); Huang et al., *J. Am. Chem. Soc.* 124:10320-35 (2002); Mazaleyrat et al., *J. Am. Chem. Soc.* 126:12874-79 (2004); Superchi et al., *J. Am. Chem. Soc.* 128:6893-902 (2006); Holmes et al., *J. Am. Chem. Soc.* 129:1506-07 (2007); Dutot et al., *J. Am. Chem. Soc.* 130:5986-92 (2008); Kim et al., *Angew. Chem. Int. Ed.* 47:8657-60 (2008); Waki et al., *Angew. Chem. Int. Ed.* 46:3059-61 (2007); Katoono et al., *J. Am. Chem. Soc.* 131:16896-904 (2009); Ghosn & Wolf, *J. Am. Chem. Soc.* 131:16360-61 (2009); Ghosn & Wolf, *Tetrahedron* 66:3989-94 (2010); Ghosn & Wolf, *J. Org. Chem.* 76:3888-97 (2011); Ghosn & Wolf, *Tetrahedron* 67:6799-803 (2011); Joyce et al., *J. Am. Chem. Soc.* 133:13746-52 (2011); You et al., *J. Am. Chem. Soc.* 134:7117-25 (2012); Wezenberg et al., *Angew. Chem. Int. Ed.* 50:713-16 (2011); Iwaniuk & Wolf, *J. Am. Chem. Soc.* 133:2414-17 (2011); Iwaniuk & Wolf, *Org. Lett.* 13:2602-05 (2011); Iwaniuk et al., *Chirality* 24:584-89 (2012); Li et al., *J. Am. Chem. Soc.* 134:9026-29 (2012); Iwaniuk & Wolf, *Chem. Commun.* 48:11226-28 (2012)).

Circular dichroism spectroscopy is one of the most powerful techniques commonly used for elucidation of the three-dimensional structure, molecular recognition events, and stereodynamic processes of chiral compounds (Gawroński & Grajewski, *Org. Lett.* 5:3301-03 (2003); Allenmark, *Chirality* 15:409-22 (2003); Berova et al., *Chem. Soc. Rev.* 36:914-31 (2007)). The potential of chiroptical CD (circular dichroism) and CPL (circular polarized luminescence) assays with carefully designed probes that produce a circular dichroism signal upon recognition of a chiral substrate has received increasing attention in recent years, and bears considerable promise with regard to high-throughput ee screening (Nieto et al., *J. Am. Chem.* 130:9232-33 (2008); Leung et al., *Chem. Soc. Rev.* 41:448-79 (2012); Song et al., *Chem. Commun.* 49:5772-74 (2013) (chirality CPL sensing)).

Many examples of chirality chemosensing with stereodynamic molecular receptors or supramolecular arrangements that generate a characteristic CD signal upon covalent or non-covalent binding of a target compound have been reported (e.g., Bentley & Wolf, *J. Am. Chem. Soc.* 135: 12200 (2013); Ghosn & Wolf, *J. Am. Chem. Soc.* 131:16360 (2009); Ghosn & Wolf, *J. Org. Chem.* 76:3888 (2011); Ghosn & Wolf, *Tetrahedron* 67:6799 (2011); Hembury et al., Review, *Chem. Rev.* 108:1-73 (2008) (supramolecular sensors); Holmes et al., *Chirality* 14:471 (2002); Iwaniuk & Wolf, *Chem. Commun.* 48:11226 (2012); Iwaniuk & Wolf, *J. Am. Chem. Soc.* 133:2414 (2011); Iwaniuk & Wolf, *Org. Lett.* 13:2602 (2011); Iwaniuk et al., *Chirality* 24:584 (2012); Katoono et al., *Tetrahedron Lett.* 47:1513-18 (2006); Kawai et al., *Chem. Eur. J.* 11:815-24 (2005); Kohmoto et al., *Tetrahedron Lett.* 49:1223-27 (2008); Leung & Anslyn, *Org. Lett.* 13:2298 (2011); Matile et al., *J. Am. Chem. Soc.* 33:2072 (1993); Nieto et al., *J. Am. Chem. Soc.* 130:9232 (2008); Tartaglia et al., *J. Org. Chem.* 73:4865 (2008); Tartaglia et al., *Org. Lett.* 10:3421-24 (2008); Tumambac et al., *Eur. J. Org. Chem.* 3850-56 (2004); Wolf & Bentley, Review, *Chem. Soc. Rev.* 42:5408 (2013); Zhang & Wolf, *Chem. Comm.* 49:7010 (2013)). This includes biphenyl-derived probes that populate a thermodynamically favored chiral conformation upon reaction with one enantiomer of an amino acid, carboxylic acid, amine, or alcohol. This chiral induction process yields a Cotton effect that can be correlated to the absolute configuration of the covalently-bound substrate (Superchi et al., *Angew. Chem. Int. Ed.* 40:451-54 (2001); Hosoi et al., *Tetrahedron Lett.* 42:6315-17 (2001); Mazaleyrat et al., *J. Am. Chem. Soc.* 126:12874-79 (2004); Mazaleyrat et al., *Chem. Eur. J.* 11:6921-29 (2005); Superchi et al., *J. Am. Chem. Soc.* 128:6893-902 (2006); Dutot et al., *J. Am. Chem. Soc.* 130:5986-92 (2008); Kuwahara et al., *Org. Lett.* 15:5738-41 (2013)). Essentially the same concept has been exploited for chirality chemosensing by using molecular bevel gears (Sciebura et al., *Angew. Chem. Int. Ed.* 48:7069-72 (2009); Sciebura & Gawronski, *Chem. Eur. J.* 17:13138-41 (2011)), propellers (Katoono et al., *J. Am. Chem. Soc.* 131:16896-904 (2009)), or other probes that can afford a CD-active helical arrangement (Waki et al., *Angew. Chem. Int. Ed.* 46:3059-61 (2007); Tartaglia et al., *Org. Lett.* 10:3421-24 (2008); Kim et al., *Angew. Chem. Int. Ed.* 47:8657-60 (2008)). Similarly, a variety of intriguing stereodynamic chemosensors that generate strong CD signals in the presence of a chiral bias have been developed (Balaz et al., *Angew. Chem. Int. Ed.* 44:4006-09 (2005); Berova et al., *Chem. Commun.* 5958-80 (2009); Borovkov et al., *J. Am. Chem. Soc.* 123:2979-89 (2001); Canary et al., *Chem. Commun.* 46:5850-60 (2010); Holmes et al., *J. Am. Chem. Soc.* 129:1506-07 (2007); Huang et al., *J. Am. Chem. Soc.* 124: 10320-35 (2002); Ishii et al., *Chirality* 17:305-15 (2005); Joyce et al., *Chem. Eur. J.* 18:8064-69 (2012); Joyce et al., *J. Am. Chem. Soc.* 133:13746-52 (2011); Katoono et al.,

*Tetrahedron Lett.* 47:1513-18 (2006); Kikuchi et al., *J. Am. Chem. Soc.* 114:1351-58 (1992); Kim et al., *Chem. Commun.* 49:11412-14 (2013); Kurtan et al., *J. Am. Chem. Soc.* 123:5962-73 (2001); Kurtan et al., *J. Am. Chem. Soc.* 123:5974-82 (2001); Li et al., *J. Am. Chem. Soc.* 130:1885-93 (2008); Li & Borhan, *J. Am. Chem. Soc.* 130:16126-27 (2008); Li et al., *J. Am. Chem. Soc.* 134:9026-29 (2012); Nieto et al., *Chem. Eur. J.* 16:227-32 (2010); Proni et al., *Chem. Commun.* 1590-91 (2002); Proni et al., *J. Am. Chem. Soc.* 125:12914-27 (2003); Tamiaki et al., *Tetrahedron* 59:10477-83 (2003); Tsukube et al., *J. Chem. Soc. Dalton Trans.* 1:11-12 (1999); Waki et al., *Angew. Chem. Int. Ed.* 46:3059-61 (2007); Wezenberg et al., *Angew. Chem. Int. Ed.* 50:713-16 (2011); Yang et al., *Org. Lett.* 4:3423-26 (2002); You et al., *J. Am. Chem. Soc.* 134:7117-25 (2012); You et al., *J. Am. Chem. Soc.* 134:7126-34 (2012); You et al., *Nat. Chem.* 3:943-48 (2011); Zhang et al., *Chirality* 15:180-89 (2003)). In many cases, the CD output of the chemosensor allows determination of the absolute configuration and the enantiomeric composition of the chiral analyte (Wolf & Bentley, *Chem. Soc. Rev.* 42:5408-24 (2013)).

But the analysis of the concentration and the enantiomeric composition of chiral substrates by a single optical chemosensor is a difficult task, and a practical method that is applicable to many chiral compounds and avoids time consuming derivatization and purification steps is very desirable (Nieto et al., *Org. Lett.* 10:5167-70 (2008); Nieto et al., *Chem. Eur. J.* 16:227-32 (2010); Yu et al., *J. Am. Chem. Soc.* 134:20282-85 (2012)). Despite the general usefulness of tropos ligands in asymmetric catalysis, their potential as induced circular dichroism probes for fast concentration and ee analysis has remained unexplored. Achiral (salen)cobalt complexes have also not been used to probe chirality and to determine ee's.

The present invention is directed to overcoming these and other deficiencies in the art.

SUMMARY OF THE INVENTION

A first aspect of the present invention relates to an analytical method comprising:

providing a sample potentially containing a chiral analyte that can exist in stereoisomeric forms;

providing a racemic mixture of a probe having the formula $A_m$-$MR_n$—$Y_o$, wherein:
  each A is independently a chiral ligand that undergoes rapid stereoisomeric interconversion,
  M is a metal,
  each R is independently a metal coordinating ligand,
  each Y is independently a displaceable ligand,
  m is an integer from 1 to 6, and
  n and o are each independently an integer from 0 to 6, wherein the sum of m, n, and o is from 1 to 6;

contacting the sample with the racemic mixture under conditions effective to form probe-analyte complexes; and determining, based on the probe-analyte complexes that form, the stereoisomeric excess of the analyte in the sample, and/or the concentration of the analyte in the sample, and/or the absolute configuration of the analyte in the sample.

A second aspect of the present invention relates to an analytical method comprising:

providing a sample potentially containing a chiral analyte that can exist in stereoisomeric forms;

providing probes having the formula $A_m$-$MR_n$—$Y_o$, wherein:
  each A is independently an achiral ligand capable of populating one or more chiral conformations or chiral configurations in the presence of the analyte,
  M is a metal,
  each R is independently a metal coordinating ligand,
  each Y is independently a displaceable ligand,
  m is an integer from 1 to 6, and
  n and o are each independently an integer from 0 to 6, wherein the sum of m, n, and o is from 1 to 6;

contacting the sample with the probes under conditions effective to form probe-analyte complexes; and determining based on the probe-analyte complexes that form, the stereoisomeric excess of the analyte in the sample, and/or the concentration of the analyte in the sample, and/or the absolute configuration of the analyte in the sample.

A third aspect of the present invention relates to an analytical method comprising:

providing a sample potentially containing a chiral analyte that can exist in stereoisomeric forms;

providing a racemic mixture of a stereodynamic ligand having the formula $A'R'_p Y'_q$, wherein:
  A' is a chiral moiety that undergoes rapid stereoisomeric interconversion,
  each R' is independently a metal coordinating moiety,
  each Y' is independently a displaceable moiety, and
  p and q are each independently an integer from 0 to 6, wherein the sum of p and q is from 1 to 6;

providing a metal complex having the formula $MR_r Y_s$, wherein:
  M is a metal,
  each R is independently a metal coordinating ligand,
  each Y is independently a displaceable ligand, and
  r and s are each independently an integer from 0 to 6, wherein the sum of r and s is from 0 to 6;

contacting the sample with the stereodynamic ligand and the metal complex under conditions effective to form probe-analyte complexes; and determining, based on the probe-analyte complexes that form, the stereoisomeric excess of the analyte in the sample, and/or the concentration of the analyte in the sample, and/or the absolute configuration of the analyte in the sample.

A fourth aspect of the present invention relates to an analytical method comprising:

providing a sample potentially containing a chiral analyte that can exist in stereoisomeric forms;

providing a stereodynamic ligand having the formula $A'R'_p Y'_q$, wherein:
  A' is an achiral moiety capable of populating one or more chiral conformations or chiral configurations in the presence of the analyte,
  each R' is independently a metal coordinating moiety,
  each Y' is independently a displaceable moiety, and
  p and q are each independently an integer from 0 to 6, wherein the sum of p and q is from 1 to 6; and providing a metal complex having the formula $MR_r Y_s$, wherein:
  M is a metal,
  each R is independently a metal coordinating ligand,
  each Y is independently a displaceable ligand, and
  r and s are each independently an integer from 0 to 6, wherein the sum of r and s is from 0 to 6;

contacting the sample with the stereodynamic ligand and the metal complex under conditions effective to form probe-analyte complexes; and determining, based on the probe-analyte complexes that form, the stereoisomeric excess of the analyte in the sample, and/or the concentration of the analyte in the sample, and/or the absolute configuration of the analyte in the sample.

As demonstrated herein, palladium(II) complexes carrying chromophoric tropos ligands show a characteristic UV change and strong Cotton effects upon coordination of a number of substrates. The distinct (chir)optical responses can be used for instantaneous in situ determination of the concentration and ee of the substrates at low concentrations.

Stereodynamic ligand-metal complexes for determination of the absolute configuration and enantiomeric composition of a variety of chiral analytes are also described herein. The molecular recognition and chirality sensing events are based on spontaneous asymmetric transformation of the first kind with stereolabile binaphtholate boron and zinc complexes. The substrate binding and chiral amplification processes yield a distinctive chiroptical sensor output at high wavelength that can be used for rapid and accurate ee detection of minute sample amounts.

Coordination of a chiral substrate to (meso-salen)cobalt (II) nitrate and subsequent oxidation generates a Co(III) complex exhibiting a strong chiroptical readout that is attributed to spontaneous substrate-to-ligand chirality imprinting. The characteristic CD response of the (salen) cobalt complex can be used for enantiomeric analysis of a variety of chiral substrates based on a simple CD measurement at low concentration and without additional purification steps. This chirality sensing approach has potential for high-throughput ee screening applications and minimizes solvent waste production.

It is expected that other metal-stereodynamic ligand probes can also be used to determine the stereoisomeric excess, and/or the concentration, and/or the absolute configuration of various analytes.

BRIEF DESCRIPTION OF THE DRAWINGS

FIGS. 97A-C relate to the CD sensing of diamines, amines, and amino alcohols. FIG. 97A is the CD spectra of the Zn complex derived from 2 and (1R,2R)-8 (solid blue (a)) or (1S,2S)-8 (solid red (b)) and from 1 and (1R,2R)-8 (dashed blue (c)) or (1S,2S)-8 (dashed red (d)). FIG. 97B is the CD spectra of the Zn complex derived from 2 and (R)-9 (solid blue (a)) or (S)-9 (solid red (b)). FIG. 97C is the CD spectra of the Zn complex derived from 2 and (1R,2S)-19 (solid blue (a)) or (1S,2R)-19 (solid red (b)). Concentrations of samples were $3.0 \times 10^{-4}$ M in $Et_2O$. Only one enantiomer of the substrates tested is shown.

FIGS. 98A-B relate to the CD sensing of hydroxy acids and amino acids. FIG. 98A is the CD spectra of the B complex derived from 2 and (R)-21 (solid blue (a)) or (S)-21 (solid red (b)) and from 1 and (R)-21 (dashed blue (c)). FIG. 98B is the CD spectra of the B complex derived from 2 and (R)-27 (solid red (a)) or (S)-27 (solid blue (b)). Concentrations of samples were $3.0 \times 10^{-4}$ M in $Et_2O$. Only one enantiomer of the substrates tested is shown.

FIG. 119 is the MS spectrum of the complex obtained from 5, $Co(NO_3)_2$, and (1R,2R)-6. [5-Co-6]$^+$: m/z=789.26; [5-Co]$^+$: m/z=577.13.

FIG. 120 is the MS spectrum of the complex obtained from 5, $Co(NO_3)_2$, and (1R,2R)-10. [5-Co-10]$^+$: m/z=726.22; [5-Co]$^+$: m/z=577.13.

FIG. 121 shows the configurations of octahedral cobalt (III) complexes.

DETAILED DESCRIPTION OF THE INVENTION

Figure 1A:
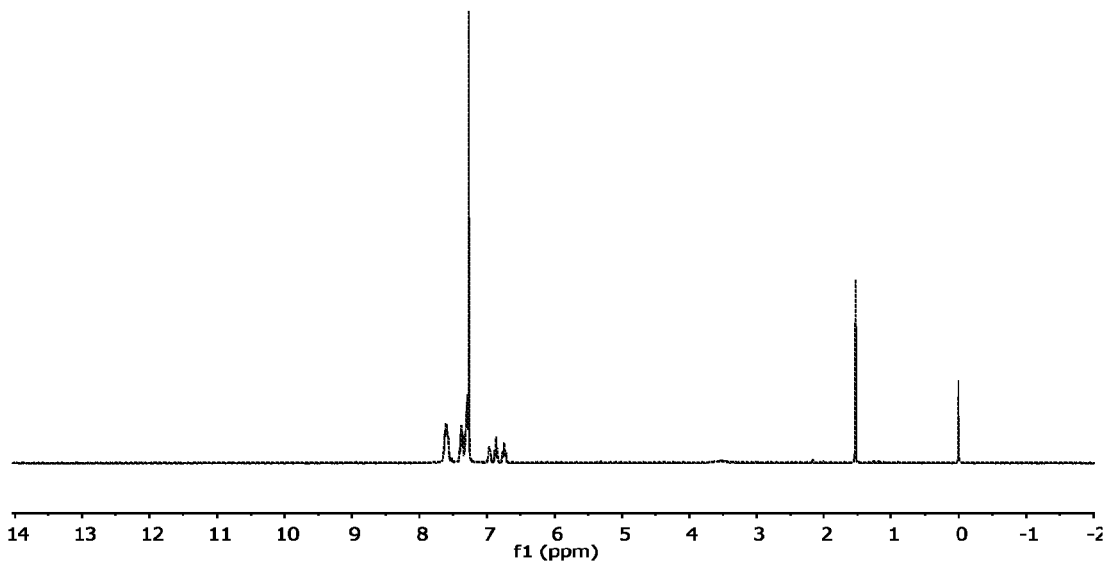
FIGS. 1A-B are $^1$H NMR (FIG. 1A) and $^{13}$C NMR (FIG. 1B) spectra of [bis(2-(diphenylphosphino)phenyl)ether]palladium(II) dichloride.

The methods of the present invention involve analyzing chiral analytes that can exist in stereoisomeric (enantiomeric or diastereomeric) forms, using stereodynamic ligands and metal complexes. Generally, a sample potentially containing the chiral analyte is contacted with the stereodynamic ligand and the metal ligand and a stereodynamic metal complex is formed. When analyte is present, the analyte coordinates to the metal center and initiates a chiral induction process and a spectroscopic signal change. The chiral information contained in the analyte stabilizes a distinct conformation or configuration of the stereodynamic metal complex, which can be correlated to the analyte's stereoisomeric excess, and a change in the spectroscopic signal can be correlated to the analyte concentration.

A first aspect of the present invention relates to an analytical method that involves providing a sample potentially containing a chiral analyte that can exist in stereoisomeric forms and providing a racemic mixture of a probe having the formula $A_m\text{-}MR_n\text{—}Y_o$, where:

each A is independently a chiral ligand that undergoes rapid stereoisomeric interconversion,
M is a metal,
each R is independently a metal coordinating ligand,
each Y is independently a displaceable ligand,
m is an integer from 1 to 6, and
n and o are each independently an integer from 0 to 6, wherein the sum of m, n, and o is from 1 to 6.

In this aspect of the present invention, the sample is contacted with the racemic mixture under conditions effective to form probe-analyte complexes, and the stereoisomeric excess of the analyte in the sample, and/or the concentration of the analyte in the sample, and/or the absolute configuration of the analyte in the sample is determined based on the probe-analyte complexes that form.

A second aspect of the present invention relates to an analytical method that involves providing a sample potentially containing a chiral analyte that can exist in stereoisomeric forms and providing probes having the formula $A_m\text{-}MR_n\text{—}Y_o$, where:

each A is independently an achiral ligand capable of populating one or more chiral conformations or chiral configurations in the presence of the analyte,
M is a metal,
each R is independently a metal coordinating ligand,
each Y is independently a displaceable ligand,
m is an integer from 1 to 6, and
n and o are each independently an integer from 0 to 6, wherein the sum of m, n, and o is from 1 to 6.

In this aspect of the present invention, the sample is contacted with the probes under conditions effective to form probe-analyte complexes, and the stereoisomeric excess of the analyte in the sample, and/or the concentration of the analyte in the sample, and/or the absolute configuration of the analyte in the sample is determined based on the probe-analyte complexes that form.

A third aspect of the present invention relates to an analytical method that involves providing a sample potentially containing a chiral analyte that can exist in stereoisomeric forms, providing a racemic mixture of a stereodynamic ligand having the formula $A'R'_p Y'_q$, where:

A' is a chiral moiety that undergoes rapid stereoisomeric interconversion,
each R' is independently a metal coordinating moiety,
each Y' is independently a displaceable moiety, and
p and q are each independently an integer from 0 to 6, wherein the sum of p and q is from 1 to 6; and
providing a metal complex having the formula $MR_r Y_s$, where:

M is a metal,
each R is independently a metal coordinating ligand,
each Y is independently a displaceable ligand, and
r and s are each independently an integer from 0 to 6, wherein the sum of r and s is from 0 to 6.

In this aspect of the present invention, the sample is contacted with the stereodynamic ligand and the metal complex under conditions effective to form probe-analyte complexes, and the stereoisomeric excess of the analyte in the sample, and/or the concentration of the analyte in the sample, and/or the absolute configuration of the analyte in the sample is determined based on the probe-analyte complexes that form.

A fourth aspect of the present invention relates to an analytical method that involves providing a sample potentially containing a chiral analyte that can exist in stereoisomeric forms, providing a stereodynamic ligand having the formula $A'R'_p Y'_q$, where:

A' is an achiral moiety capable of populating one or more chiral conformations or chiral configurations in the presence of the analyte,
each R' is independently a metal coordinating moiety,
each Y' is independently a displaceable moiety, and
p and q are each independently an integer from 0 to 6, wherein the sum of p and q is from 1 to 6; and
providing a metal complex having the formula $MR_r Y_s$, where:

M is a metal,
each R is independently a metal coordinating ligand,
each Y is independently a displaceable ligand, and
r and s are each independently an integer from 0 to 6, wherein the sum of r and s is from 0 to 6.

In this aspect of the present invention, the sample is contacted with the stereodynamic ligand and the metal complex under conditions effective to form probe-analyte complexes, and the stereoisomeric excess of the analyte in the sample, and/or the concentration of the analyte in the sample, and/or the absolute configuration of the analyte in the sample is determined based on the probe-analyte complexes that form.

By way of example, one embodiment of the methods of the present invention is illustrated in Scheme 2 below.

Scheme 2. Chemosensing and Chiral Induction with Stereodynamic Metal Complexes

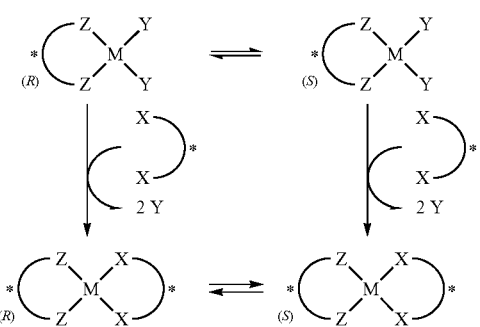

In the example shown in Scheme 2, a probe in the form of a stereodynamic metal complex (i.e.,

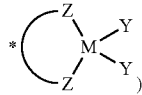

containing a stereodynamic ligand (i.e.,

and displaceable ligands (i.e., Y) is provided. The stereodynamic ligand is either a chiral ligand that undergoes rapid stereoisomeric interconversion or an achiral ligand that can populate one or more chiral conformations or chiral configurations. The displaceable ligand is any ligand that will be displaced in the presence of the analyte. When contacted with a chiral analyte (i.e.,

the analyte displaces the Y ligands, forming a probe-analyte complex, and induces the stereodynamic ligand to adopt a certain chiral conformation depending on which stereoisomer(s) of the analyte is present. (The chiral induction process shown by way of example in Scheme 2 favors the formation of the (S)-enantiomer of the stereodynamic ligand. Alternatively, this process can result in the favored population of the (R)-enantiomer of the ligand.) The particular chiroptical and optical properties of the resulting probe-analyte complex can then be analyzed and used to determine the stereoisomeric excess, and/or concentration, and/or absolute configuration of the chiral analyte originally present in the sample.

By way of example, one embodiment of the methods of the present invention is illustrated in Scheme 3 below.

Scheme 3. Chemosensing and Chiral Induction with Stereodynamic Metal Complexes

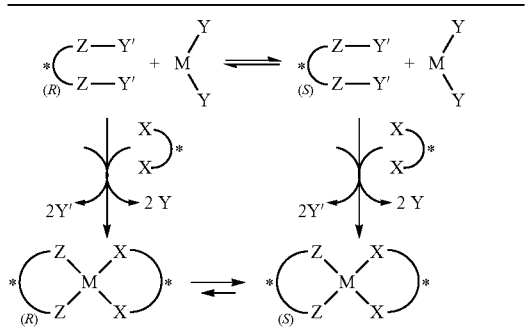

In the example shown in Scheme 3, a stereodynamic ligand (i.e.,

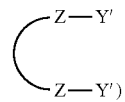

having displaceable moieties (i.e., Y'), and a metal complex (i.e.,

having displaceable ligands (i.e., Y), are provided. The stereodynamic ligand contains either a chiral moiety that undergoes rapid stereoisomeric interconversion or an achiral moiety that can populate one or more chiral conformations or chiral configurations. The displaceable moiety (Y') is any moiety that will be displaced in the presence of the metal complex. When contacted with the metal complex, the metal displaces the Y' moiety(ies), forming a stereodynamic metal complex probe. The displaceable ligand (Y) is any ligand that will be displaced in the presence of the analyte. When contacted with a chiral analyte (i.e.,

the analyte displaces the Y ligand(s), forming a metal-analyte complex. When all three of the stereodynamic ligand, metal complex, and analyte are present, a probe-analyte complex is formed, inducing the stereodynamic ligand to adopt a certain chiral conformation depending on which stereoisomer(s) of the analyte is present. (The chiral induction process shown by way of example in Scheme 3 favors the formation of the (S)-enantiomer of the stereodynamic ligand. Alternatively, this process can result in the favored population of the (R)-enantiomer of the ligand.) The particular chiroptical and optical properties of the resulting probe-analyte complex can then be analyzed and used to determine the stereoisomeric excess, and/or concentration, and/or absolute configuration of the chiral analyte originally present in the sample.

Scheme 3 shows the stereodynamic ligand being mixed with the metal complex and the sample then added. Alternatively, the metal complex can be mixed with the sample first and the stereodynamic ligand then added, or the stereodynamic ligand can be mixed with the sample first and the metal complex then added, or all three can be mixed simultaneously.

As noted above, in the first aspect of the present invention, each A is a chiral ligand that undergoes rapid stereoisomeric interconversion, and, in the third aspect of the present invention, each stereodynamic ligand contains a chiral moiety (A') that undergoes rapid stereoisomeric interconversion. Such ligands are well-known in the art. Preferably, the chiral ligand/stereodynamic ligand containing a chiral moiety is a tropos ligand. Suitable tropos ligands include, for example, 1,1'-bis(diphenylphosphino)ferrocene (DPPF), 2,2'-bis(diphenylphosphino)diphenyl ether (BDPDE), 2,2'-bis(diphenylphosphino)-1,1'-biphenyl (BIPHEP), BIPHOS, 2,2'-diaminobiphenyls, 2,2'-dihydroxybiphenyls, biphenols (e.g., 2,2'-biphenol (biphenol ligand 1 (see Example 11 for structure))), binaphthols (e.g., 1,1'-dihydroxy-2,2'-binaphthalene (binaphthol ligand 2 (see Example 11 for structure), bis(2-hydroxy-1-naphthyl)methanone (binaphthol ligand 34 (see Example 11 for structure))), and analogues of each of the preceding compounds.

As noted above, in the second aspect of the present invention, each A is an achiral ligand capable of populating one or more chiral conformations or chiral configurations in the presence of the analyte, and, in the fourth aspect of the present invention, each stereodynamic ligand contains an achiral moiety (A') capable of populating one or more chiral conformations or chiral configurations in the presence of the analyte. Such ligands can be selected based on the analyte of interest, as will be apparent to the skilled artisan. Suitable achiral ligands/stereodynamic ligands containing an achiral moiety include, for example, diamines, dicarboxylic acids, diols, diimines, diphosphines, meso salens, and analogues of each of the preceding compounds. Suitable examples include, without limitation, bis(diphenylphosphino)ethane (DPPE), meso 1,2-diaminocyclohexane, meso tartaric acid, and meso salen ligand 5 (see Example 26 for structure).

In all aspects of the present invention, the stereodynamic ligand (A or A'R'pY'q) can be monodentate (e.g., A with m being an integer from 1 to 6; e.g., A'R'pY'q with p being 1) or polydentate (e.g., A with m being an integer from 1 to 3; e.g., A'R'pY'q with p being an integer from 2 to 6). In at least one preferred embodiment, the stereodynamic ligand is bidentate. The stereodynamic ligand(s) can be charged (e.g., anionic; e.g., cationic) or neutral.

The probe-analyte complexes shown in Schemes 1 and 2 are monomeric complexes. As will be understood by one skilled in the art, other probe-analyte complexes can also be formed. For example, the probe-analyte complex can have the formula $L_xM_yX_z$, where L is the stereodynamic ligand (e.g., A; e.g., A'R'$_p$Y'$_q$ with any R' moieties present but with any Y' moieties having been displaced), M is the metal complex (e.g., MR$_n$—Y$_o$ with any R ligands present but with any Y ligands having been displaced; e.g., MR$_r$Y$_s$ with any R ligands present but with any Y ligands having been displaced), X is the analyte, and x, y, and z are each independently an integer from 1 to 5. For example, the probe-analyte complex could also be dimeric, trimeric, tetrameric, etc. When x is greater than 1, more than one stereodynamic ligand coordinates with the metal center(s). In such embodiments, each stereodynamic ligand can be the same or different. For example, complexes (i.e., stereodynamic ligand-metal complexes or probe-analyte complexes) containing only monodentate stereodynamic ligands, complexes containing only polydentate stereodynamic ligands, and complexes containing a combination of monodentate and polydentate stereodynamic ligands are contemplated. Likewise, complexes containing only charged (e.g., anionic; e.g., cationic) stereodynamic ligands, complexes containing only neutral stereodynamic ligands, and complexes containing a combination of charged and neutral stereodynamic ligands are also contemplated. Typically, the stereodynamic ligand coordinates to the metal center(s) through phosphorus, nitrogen, oxygen, carbon, or sulfur atoms, or combinations thereof.

As will be apparent to the skilled artisan, any metal may be used in the probes/ligands of the present invention, at any oxidation state. Exemplary metals according to all aspects of the present invention include, without limitation, palladium, magnesium, boron, aluminum, copper, zinc, iron, cobalt, nickel, platinum, gold, titanium, vanadium, manganese, and chromium.

In some embodiments of all aspects of the present invention, the probe, stereodynamic ligand, and/or metal complex may contain one or more metal coordinating moieties (R') or metal coordinating ligands (R). As used herein, these are moieties/ligands that coordinate with the metal but do not act as a stereodynamic ligand (A), a stereodynamic moiety (A'), a displaceable moiety (Y'), or a displaceable ligand (Y). As will be apparent to the skilled artisan, suitable metal coordinating moieties/ligands can be selected based on the particular metal, A ligand(s), A' moiety(ies), Y' and moiety (ies) (if any), and Y ligands (if any), that are present, and may be selected to complete the coordination sphere of the metal. Suitable metal coordinating moieties/ligands include any moiety/ligand that coordinates to a metal through hydrogen, carbon, nitrogen, oxygen, halide, sulfur, or phosphorus atoms. Examples include, without limitation, H, OH, NH$_2$, alkyls (e.g., $C_1$-$C_6$), alkenyls (e.g., $C_1$-$C_6$), alkynyls, halogens, halides, halogen-containing anions, haloalkyls, haloalkenyls, hydroxyls, alcohols, hydrides, carbonyls, aldehydes, carbonate esters, carboxylates, carboxyls, esters, alkoxyls (e.g., $C_1$-$C_6$), alkoxides, ethers, hemiacetals, hemiketals, acetals, ketals, orthoesters, orthocarbonate esters, amides, amines, imines, imides, azides, diimides, cyanates, cyanides, nitrates, nitriles, nitrites, nitrosos, pyridyls, thiols, thioethers, disulfides, sulfoxides, sulfones, sulfonates, thiocyanates, thiones, phosphines, phosphoric acids, phosphates, aryls, heteroaryls, arylalkyls, heterocycles, cycloalkyls, cycloalkenyls, and acyls. In embodiments in which multiple metal coordinating moieties/ligands are present (e.g., when n is greater than 1; e.g., when the sum of p and r is greater than 1), the metal coordinating moieties/ligands may be the same or different. The metal coordinating moieties/ligands may or may not interact with the analyte.

In some embodiments of the third and fourth aspects of the present invention, the stereodynamic ligand may contain one or more displaceable moieties (Y'). As used herein, these are moieties that are displaced from the stereodynamic ligand upon coordination with the metal. As will be apparent to the skilled artisan, suitable displaceable moieties can be selected based on the particular stereodynamic ligand and the particular metal. The displaceable moiety (Y') can be absent (with q being 0), monodentate, polydentate, or bidentate. In at least one preferred embodiment, the displaceable moiety is monodentate. The displaceable moiety(ies) can be charged or neutral. When q is greater than 1, more than one displaceable moiety is displaced upon coordination with the metal center. In such embodiments, each displaceable moiety can be the same or different. For example, stereodynamic ligands containing only monodentate displaceable moieties, stereodynamic ligands containing only polydentate displaceable moieties, and stereodynamic ligands containing a combination of monodentate and polydentate displaceable moieties are contemplated. Likewise, stereodynamic ligands containing only charged displaceable moieties, stereodynamic ligands containing only neutral displaceable moieties, and stereodynamic ligands containing a combination of charged and neutral displaceable moieties are also contemplated. In at least one preferred embodiment, the displaceable moiety is a proton. In at least one preferred embodiment, the displaceable moiety is absent.

In some embodiments of all aspects of the present invention, the probe/metal complex may contain one or more displaceable ligands (Y). As used herein, these are ligands that are displaced from the metal/metal complex in the presence of the analyte. As will be apparent to the skilled artisan, suitable displaceable ligands can be selected based on the particular metal present in the probe/metal complex and the particular analyte of interest. The displaceable ligand (Y) can be monodentate (with o or s being an integer from 1 to 6), polydentate (with o or s being an integer from 1 to 3), or bidentate. In at least one preferred embodiment, the displaceable ligand is monodentate. The displaceable ligand(s) can be charged or neutral. When o or s is greater than 1, more than one displaceable ligand is displaced upon the analyte's coordination with the metal center. In such embodiments, each displaceable ligand can be the same or different. For example, probes/metal complexes containing only monodentate displaceable ligands, probes/metal complexes containing only polydentate displaceable ligands, and probes/metal complexes containing a combination of monodentate and polydentate displaceable ligands are contemplated. Likewise, probes/metal complexes containing only charged displaceable ligands, probes/metal complexes containing only neutral displaceable ligands, and probes/metal complexes containing a combination of charged and neutral displaceable ligands are also contemplated. Typically, the displaceable ligand coordinates to the metal through hydrogen, carbon, phosphorus, nitrogen, oxygen, halide, carbon, or sulfur atoms, or combinations thereof. Suitable examples include, without limitation, H, OH, $NH_2$, $NCCH_3$, $CF_3SO_3^-$, alkyls (e.g., $C_1$-$C_6$), alkenyls (e.g., $C_1$-$C_6$), alkynyls, halogens, halides, halogen-containing anions, haloalkyls, haloalkenyls, hydroxyls, alcohols, hydrides, carbonyls, aldehydes, carbonate esters, carboxylates, carboxyls, esters, alkoxyls (e.g., $C_1$-$C_6$), alkoxides, ethers, hemiacetals, hemiketals, acetals, ketals, orthoesters, orthocarbonate esters, amides, amines, imines, imides, azides, diimides, cyanates, cyanides, nitrates, nitriles, nitrites, nitrosos, pyridyls, thiols, thioethers, disulfides, sulfoxides, sulfones, sulfonates, thiocyanates, thiones, phosphines, phosphoric acids, phosphates, aryls, heteroaryls, arylalkyls, heterocycles, cycloalkyls, cycloalkenyls, phenols, phenolates, and acyls. Some preferred displaceable ligands include $NCCH_3$, $CF_3SO_3^-$, alkyls, alkenyls, hydroxyls, alkoxys, hydrides, sulfonyls, halides, amines, phosphines, and phosphates.

By way of example only, suitable metal complexes according to all aspects of the present invention include $B(OMe)_3$, $Et_2Zn$, $Mg(Ot\text{-}Bu)_2$, $Zn(OTf)_2$, $Al(Oi\text{-}Pr)_3$, 2-formyl-4-methoxyphenyl boronic acid, and cobalt salts.

By way of example only, suitable probes according to the first aspect of the present invention and suitable stereodynamic ligand-metal complexes according to the third aspect of the present invention include, without limitation,

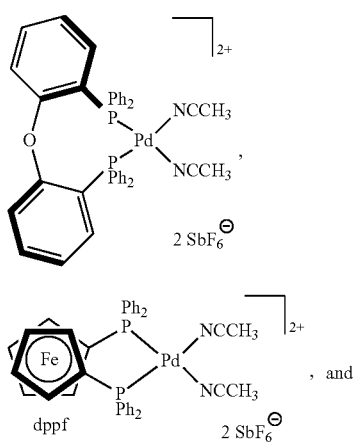

-continued

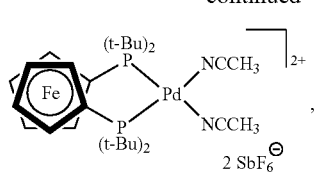

with 1 and 2 being particularly preferred. Any other combination of the stereodynamic ligands containing a chiral moiety and the metal complexes identified above are also suitable.

By way of example only, suitable probes according to the second aspect of the present invention and suitable stereodynamic ligand-metal complexes according to the fourth aspect of the present invention include, without limitation,

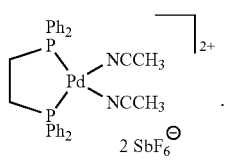

Any other combination of the stereodynamic ligands containing an achiral moiety and the metal complexes identified above are also suitable.

The analytical methods of the present invention may be used to evaluate a wide range of chiral analytes. As noted above, the analyte is one that can exist in stereoisomeric forms. This includes enantiomers, diastereomers, and a combination thereof. As will be understood by one skilled in the art, the analyte can be any chiral analyte that can coordinate with a metal. Suitable analytes include, for example, amines, diamines, alcohols, amino alcohols, carboxylic acids, amino acids, thiols, aldehydes, ketones, amides, esters, α-hydroxy acids, and any combination thereof. The analyte can interact with the probes/metal complexes by displacing a displaceable ligand, by increasing the coordination number of the metal, or a combination thereof.

In all aspects of the present invention, the stereoisomeric excess of the analyte can be determined by correlating the chiroptical signal of the probe-analyte complexes that form to the stereoisomeric excess of the analyte. The chiroptical signal of the complexes can be measured using standard techniques, which will be apparent to the skilled artisan. Such techniques include circular dichroism spectroscopy (e.g., STEREOCHEMISTRY OF ORGANIC COMPOUNDS 1003-07 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety), optical rotatory dispersion (e.g., STEREOCHEMISTRY OF ORGANIC COMPOUNDS 999-1003 (E. L. Eliel & S. H. Wilen eds., 1994), which is hereby incorporated by reference in its entirety), and polarimetry (e.g., STEREOCHEMISTRY OF ORGANIC COMPOUNDS 217-21, 1071-80 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety). By way of example, stereomerically pure samples of each isomer of an analyte of interest can be mixed with the particular probe(s) or the particular stereodynamic ligand(s) and metal complex(es) to generate standard samples, and their optical spectra obtained. The chiroptical signal of the probe-analyte complexes in the test sample can be measured by generating an optical spectrum of the test sample. The stereoisomeric excess of the analyte originally present in the sample can then be determined by comparing the optical spectrum of the test sample to that of the standard sample(s).

In all aspects of the present invention, the concentration of the analyte can be determined by correlating a non-chiroptical spectroscopic signal of the probe-analyte complexes that form to the concentration of the analyte. The non-chiroptical spectroscopic signal can be measured using standard techniques, which will be apparent to the skilled artisan. Such techniques include, but are not limited to, UV spectroscopy (PRINCIPLES OF INSTRUMENTAL ANALYSIS 342-47 (Douglas A. Skoog et al. eds., 5$^{th}$ ed. 1998), which is hereby incorporated by reference in its entirety), fluorescence spectroscopy, and other spectroscopic techniques. By way of example, serial titrations of the analyte of interest can be mixed with the particular probe or the particular stereodynamic ligand(s) and metal complex(es) to generate standard samples and their spectra (e.g., UV, fluorescence) obtained. The spectroscopic signal (e.g., UV, fluorescence) of the probe-analyte complexes can be measured by generating a spectrum (e.g., UV, fluorescence) of the test sample. The total concentration of the analyte originally present in the sample can then be determined by comparing the spectrum of the test sample to the titration curve of the standard samples. As will be apparent to the skilled artisan, if the stereoisomeric excess of the analyte is also determined, the concentration of individual isomers originally present in the test sample can be determined by comparing the stereoisomeric excess to the total analyte concentration.

In all aspects of the present invention, the absolute configuration of the analyte can be assigned from the chiroptical signal of the probe-analyte complexes that form. This assignment can be based on the sense of chirality induction with a reference or by analogy. The chiroptical signal of the complexes can be measured using standard techniques, which will be apparent to the skilled artisan. Such techniques include circular dichroism spectroscopy (e.g., STEREOCHEMISTRY OF ORGANIC COMPOUNDS 1003-07 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety), optical rotatory dispersion (e.g., STEREOCHEMISTRY OF ORGANIC COMPOUNDS 999-1003 (E. L. Eliel & S. H. Wilen eds., 1994), which is hereby incorporated by reference in its entirety), and polarimetry (e.g., STEREOCHEMISTRY OF ORGANIC COMPOUNDS 217-21, 1071-80 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety). By way of example, stereoisomerically pure samples of each isomer of an analyte of interest can be mixed with the particular probe(s) or the particular stereodynamic ligand(s) and metal complex(es) to generate standard samples, and their optical spectra obtained. The chiroptical signal of the probe-analyte complexes in the test sample can be measured by generating an optical spectrum of the test sample. The absolute configuration of the analyte originally present in the sample can then be determined by comparing the optical spectrum of the test sample to that of the standard sample(s).

The methods of the present invention provide, among other things, rapid and convenient tools for determining the stereoisomeric excess, and/or concentration, and/or absolute configuration of chiral analytes. These analytical methods may be particularly useful, for example, for evaluating high-throughput reactions whose desired product is chiral. For example, the present methods can be used to determine the stereoisomeric excess of the desired product, thus indicating the stereoselectivity of the reaction. Similarly, the present methods can be used to determine the concentration of the total product and/or the desired isomer, thus indicating the overall or individual yield of the reaction.

Preferred embodiments include the following methods.

An analytical method comprising: providing a sample potentially containing a chiral analyte that can exist in stereoisomeric forms; providing a racemic mixture of a probe having the formula $A_m$-$MR_n Y_o$, wherein:

each A is independently a chiral ligand that undergoes rapid stereoisomeric interconversion, M is a metal, each R is independently a metal coordinating ligand, each Y is independently a displaceable ligand, m is an integer from 1 to 6, and n and o are each independently an integer from 0 to 6, wherein the sum of m, n, and o is from 1 to 6;

contacting the sample with the racemic mixture under conditions effective to form probe-analyte complexes; and determining, based on the probe-analyte complexes that form, the stereoisomeric excess of the analyte in the sample, and/or the concentration of the analyte in the sample, and/or the absolute configuration of the analyte in the sample.

The analytical method as described in paragraph [0170], wherein A is monodentate and n is an integer from 1 to 6.

The analytical method as described in paragraph [0170], wherein A is polydentate and n is an integer from 1 to 3.

The analytical method as described in paragraph [0172], wherein A is bidentate.

The analytical method as described in paragraph [0170], wherein at least one A is anionic.

The analytical method as described in paragraph [0170], wherein at least one A is neutral.

The analytical method as described in paragraph [0170], wherein A is a tropos ligand.

The analytical method as described in paragraph [0176], wherein A is selected from the group consisting of 1,1'-bis(diphenylphosphino)ferrocene (DPPF), 2,2'-bis(diphenylphosphino)diphenyl ether (BDPDE), 2,2'-bis(diphenylphosphino)-1,1'-biphenyl (BIPHEP), BIPHOS, 2,2'-diaminobiphenyls, 2,2'-dihydroxybiphenyls, and analogues of each of the preceding compounds.

The analytical method as described in paragraph [0177], wherein A is DPPF or BDPDE.

The analytical method as described in paragraph [0170], wherein M is selected from the group consisting of palladium, magnesium, boron, aluminum, copper, zinc, iron, cobalt, nickel, platinum, gold, titanium, vanadium, manganese, chromium and cobalt.

The analytical method as described in paragraph [0179], wherein M is Pd(II).

The analytical method as described in paragraph [0170], wherein Y is monodentate and n is an integer from 1 to 6.

The analytical method as described in paragraph [0170], wherein Y is polydentate and n is an integer from 1 to 3.

The analytical method as described in paragraph [0182], wherein Y is bidentate.

The analytical method as described in paragraph [0170], wherein at least one Y is charged.

The analytical method as described in paragraph [0170], wherein at least one Y is neutral.

The analytical method as described in paragraph [0170], wherein each Y is independently selected from the group consisting of H, OH, $NH_2$, $NCCH_3$, $CF_3SO_3^-$, alkyls, alkenyls, alkynyls, halogens, halides, halogen-containing anions, haloalkyls, haloalkenyls, hydroxyls, alcohols, hydrides, carbonyls, aldehydes, carbonate esters, carboxylates, carboxyls, esters, alkoxyls, alkoxides, ethers, hemiacetals, hemiketals, acetals, ketals, orthoesters, orthocarbonate esters, amides, amines, imines, imides, azides, diimides, cyanates, cyanides, nitrates, nitriles, nitrites, nitrosos, pyridyls, thiols, thioethers, disulfides, sulfoxides, sulfones, sulfonates, thiocyanates, thiones, phosphines, phosphoric acids, phosphates, aryls, heteroaryls, arylalkyls, heterocycles, cycloalkyls, cycloalkenyls, phenols, phenolates, and acyls.

The analytical method as described in paragraph [0186], wherein each Y is $NCCH_3$.

The analytical method as described in paragraph [0170], wherein the probe is selected from the group consisting of

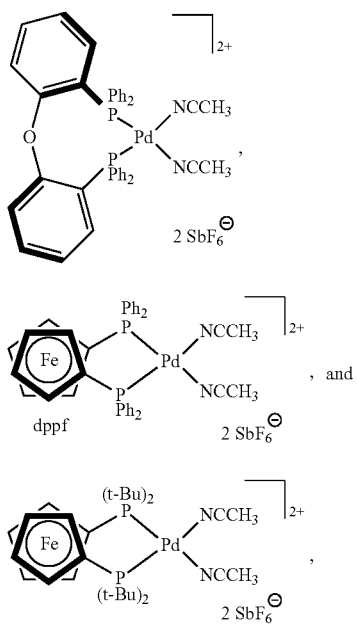

The analytical method as described in paragraph [0188], wherein the probe is

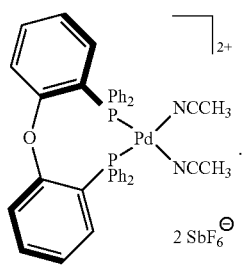

The analytical method as described in paragraph [0188], wherein the probe is

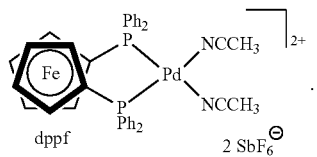

The analytical method as described in paragraph [0170], wherein the analyte is a compound selected from the group consisting of amines, alcohols, amino alcohols, carboxylic acids, amino acids, thiols, aldehydes, ketones, amides, esters, and any combination thereof.

The analytical method as described in paragraph [0191], wherein the analyte is a diamine or an amino alcohol.

The analytical method as described in paragraph [0170], wherein the stereoisomeric excess of the analyte is determined.

The analytical method as described in paragraph [0193], wherein the stereoisomeric excess is determined using circular dichroism spectroscopy, optical rotatory dispersion, or polarimetry.

The analytical method as described in paragraph [0194], wherein the stereoisomeric excess is determined using circular dichroism spectroscopy.

The analytical method as described in paragraph [0193], wherein the analyte is a reaction product and the stereoselectivity of the reaction is determined by determining the stereoisomeric excess of the analyte.

The analytical method as described in paragraph [0170], wherein the concentration of the analyte is determined.

The analytical method as described in paragraph [0197], wherein the concentration is determined using UV spectroscopy, fluorescence spectroscopy, and/or other spectroscopic techniques.

The analytical method as described in paragraph [0198], wherein the concentration is determined using UV spectroscopy.

The analytical method as described in paragraph [0198], wherein the concentration is determined using fluorescence spectroscopy.

The analytical method as described in paragraph [0197], wherein the analyte is a reaction product and the yield of the reaction is determined by determining the concentration of the analyte.

The analytical method as described in paragraph [0170], wherein the absolute configuration of the analyte is determined.

The analytical method as described in paragraph [0170], wherein the stereoisomeric excess of the analyte and the concentration of the analyte are both determined.

The analytical method as described in paragraph [0203] further comprising: determining the individual concentration of any particular stereoisomers present in the sample based on the determined concentration of the analyte and the determined stereoisomeric excess.

The analytical method as described in paragraph [0170], wherein the stereoisomeric excess of the analyte, the concentration of the analyte, and the absolute configuration of the analyte are all determined.

An analytical method comprising: providing a sample potentially containing a chiral analyte that can exist in stereoisomeric forms; providing probes having the formula $A_m\text{-}MR_nY_o$, wherein:

each A is independently an achiral ligand capable of populating one or more chiral conformations or chiral configurations in the presence of the analyte, M is a metal, each R is independently a metal coordinating ligand, each Y is independently a displaceable ligand, m is an integer from 1 to 6, and n and o are each independently an integer from 0 to 6, wherein the sum of m, n, and o is from 1 to 6;

contacting the sample with the probes under conditions effective to form probe-analyte complexes; and determining based on the probe-analyte complexes that form, the stereoisomeric excess of the analyte in the sample, and/or the concentration of the analyte in the sample, and/or the absolute configuration of the analyte in the sample.

The analytical method as described in paragraph [0206], wherein A is monodentate and n is an integer from 1 to 6.

The analytical method as described in paragraph [0206], wherein A is polydentate and n is an integer from 1 to 3.

The analytical method as described in paragraph [0208], wherein A is bidentate.

The analytical method as described in paragraph [0206], wherein at least one A is anionic.

The analytical method as described in paragraph [0206], wherein at least one A is neutral.

The analytical method as described in paragraph [0206], wherein A is selected from the group consisting of diamines, dicarboxylic acids, diols, diimines, diphosphines, and analogues of each of the preceding compounds.

The analytical method as described in paragraph [0212], wherein A is selected from the group consisting of bis(diphenylphosphino)ethane (DPPE), meso 1,2-diaminocyclohexane, and meso tartaric acid.

The analytical method as described in paragraph [0213], wherein A is DPPE.

The analytical method as described in paragraph [0206], wherein M is selected from the group consisting of palladium, magnesium, boron, aluminum, copper, zinc, iron, cobalt, nickel, platinum, gold, titanium, vanadium, manganese, chromium and cobalt.

The analytical method as described in paragraph [0215], wherein M is Pd(II).

The analytical method as described in paragraph [0206], wherein Y is monodentate and n is an integer from 1 to 6.

The analytical method as described in paragraph [0206], wherein Y is polydentate and n is an integer from 1 to 3.

The analytical method as described in paragraph [0218], wherein Y is bidentate.

The analytical method as described in paragraph [0206], wherein at least one Y is charged.

The analytical method as described in paragraph [0206], wherein at least one Y is neutral.

The analytical method as described in paragraph [0206], wherein each Y is independently selected from the group consisting of H, OH, $NH_2$, $NCCH_3$, $CF_3SO_3^-$, alkyls, alkenyls, alkynyls, halogens, halides, halogen-containing anions, haloalkyls, haloalkenyls, hydroxyls, alcohols, hydrides, carbonyls, aldehydes, carbonate esters, carboxylates, carboxyls, esters, alkoxyls, alkoxides, ethers, hemiacetals, hemiketals, acetals, ketals, orthoesters, orthocarbonate esters, amides, amines, imines, imides, azides, diimides, cyanates, cyanides, nitrates, nitriles, nitrites, nitrosos, pyridyls, thiols, thioethers, disulfides, sulfoxides, sulfones, sulfonates, thiocyanates, thiones, phosphines, phosphoric acids, phosphates, aryls, heteroaryls, arylalkyls, heterocycles, cycloalkyls, cycloalkenyls, phenols, phenolates, and acyls.

The analytical method as described in paragraph [0222], wherein each Y is $NCCH_3$.

The analytical method as described in paragraph [0206], wherein the probe is

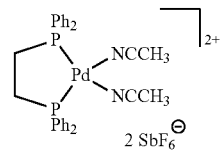

4

The analytical method as described in paragraph [0206], wherein the analyte is a compound selected from the group consisting of amines, alcohols, amino alcohols, carboxylic acids, amino acids, thiols, aldehydes, ketones, amides, esters, and any combination thereof.

The analytical method as described in paragraph [0225], wherein the analyte is a diamine or an amino alcohol.

The analytical method as described in paragraph [0206], wherein the stereoisomeric excess is determined using circular dichroism spectroscopy, optical rotatory dispersion, or polarimetry.

The analytical method as described in paragraph [0227], wherein the stereoisomeric excess is determined using circular dichroism spectroscopy.

The analytical method as described in paragraph [0206], wherein the concentration is determined using UV spectroscopy, fluorescence spectroscopy, and/or other spectroscopic techniques.

The analytical method as described in paragraph [0229], wherein the concentration is determined using UV spectroscopy.

The analytical method as described in paragraph [0229], wherein the concentration is determined using fluorescence spectroscopy.

The analytical method as described in paragraph [0206], wherein the analyte is a reaction product and the stereoselectivity and yield of the reaction are determined by determining the stereoisomeric excess and concentration of the analyte.

The analytical method as described in paragraph [0206] further comprising: determining the individual concentration of any particular stereoisomers present in the sample based on the determined concentration of the analyte and the determined stereoisomeric excess.

The analytical method as described in paragraph [0206], wherein the absolute configuration of the analyte is determined.

An analytical method comprising: providing a sample potentially containing a chiral analyte that can exist in stereoisomeric forms; providing (i) a racemic mixture of a stereodynamic ligand having the formula $A'R'_pY'_q$, wherein:

A' is a chiral moiety that undergoes rapid stereoisomeric interconversion, each R' is independently a metal coordinating moiety, each Y' is independently a displaceable moiety, and p and q are each independently an integer from 0 to 6, wherein the sum of p and q is from 1 to 6; or (ii) a stereodynamic ligand having the formula $A'R'_pY'_q$, wherein:

A' is an achiral moiety capable of populating one or more chiral conformations or chiral configurations in the presence of the analyte, each R' is independently a metal coordinating moiety, each Y' is independently a displaceable moiety, and p and q are each independently an integer from 0 to 6, wherein the sum of p and q is from 1 to 6;

providing a metal complex having the formula $MR_rY_s$, wherein:

M is a metal, each R is independently a metal coordinating ligand, each Y is independently a displaceable ligand, and r and s are each independently an integer from 0 to 6, wherein the sum of r and s is from 0 to 6;

contacting the sample with the stereodynamic ligand and the metal complex under conditions effective to form probe-analyte complexes; and determining, based on the probe-analyte complexes that form, the stereoisomeric excess of the analyte in the sample, and/or the concentration of the analyte in the sample, and/or the absolute configuration of the analyte in the sample.

The analytical method as described in paragraph [0235], wherein the stereodynamic ligand is monodentate and p is 1.

The analytical method as described in paragraph [0235], wherein the stereodynamic ligand is polydentate and p is an integer from 2 to 6.

The analytical method as described in paragraph [0237], wherein the stereodynamic ligand is bidentate.

The analytical method as described in paragraph [0235], wherein at least one stereodynamic ligand is charged.

The analytical method as described in paragraph [0235], wherein at least one stereodynamic ligand is neutral.

The analytical method as described in paragraph [0235], wherein Y' is monodentate.

The analytical method as described in paragraph [0235], wherein Y' is polydentate.

The analytical method as described in paragraph [0242], wherein Y' is bidentate.

The analytical method as described in paragraph [0235], wherein at least one Y' is charged.

The analytical method as described in paragraph [0235], wherein at least one Y' is neutral.

The analytical method as described in paragraph [0235], wherein each Y' is independently a proton or absent.

The analytical method as described in paragraph [0235], wherein M is selected from the group consisting of palladium, magnesium, boron, aluminum, copper, zinc, iron, cobalt, nickel, platinum, gold, titanium, vanadium, manganese, and chromium.

The analytical method as described in paragraph [0247], wherein $MR_rY_s$ is selected from the group consisting of $B(OMe)_3$, $Et_2Zn$, $Mg(Ot-Bu)_2$, $Zn(OTf)_2$, $Al(Oi-Pr)_3$, 2-formyl-4-methoxyphenyl boronic acid, and cobalt salts.

The analytical method as described in paragraph [0235], wherein Y is monodentate.

The analytical method as described in paragraph [0235], wherein Y is polydentate.

The analytical method as described in paragraph [0250], wherein Y is bidentate.

The analytical method as described in paragraph [0235], wherein at least one Y is charged.

The analytical method as described in paragraph [0235], wherein at least one Y is neutral.

The analytical method as described in paragraph [0235], wherein each Y is independently selected from the group consisting of H, OH, $NH_2$, $NCCH_3$, $CF_3SO_3^-$, alkyls, alkenyls, alkynyls, halogens, halides, halogen-containing anions, haloalkyls, haloalkenyls, hydroxyls, alcohols, hydrides, carbonyls, aldehydes, carbonate esters, carboxylates, carboxyls, esters, alkoxyls, alkoxides, ethers, hemiacetals, hemiketals, acetals, ketals, orthoesters, orthocarbonate esters, amides, amines, imines, imides, azides, diimides, cyanates, cyanides, nitrates, nitriles, nitrites, nitrosos, pyridyls, thiols, thioethers, disulfides, sulfoxides, sulfones, sulfonates, thiocyanates, thiones, phosphines, phosphoric acids, phosphates, aryls, heteroaryls, arylalkyls, heterocycles, cycloalkyls, cycloalkenyls, phenols, phenolates, and acyls.

The analytical method as described in paragraph [0235], wherein the probe-analyte complex has the formula $L_xM_yX_z$, wherein:

L is the stereodynamic ligand,

M is the metal,

X is the analyte, and x, y, and z are each independently an integer from 1 to 5.

The analytical method as described in paragraph [0235], wherein a racemic mixture of a stereodynamic ligand having the formula $A'R'_pY'_q$ is provided and wherein A' is a chiral moiety that undergoes rapid stereoisomeric interconversion.

The analytical method as described in paragraph [0256], wherein the stereodynamic ligand is a tropos ligand.

The analytical method as described in paragraph [0257], wherein the stereodynamic ligand is selected from the group consisting of biphenols, binaphthols, and analogues of each of the preceding compounds.

The analytical method as described in paragraph [0258], wherein the stereodynamic ligand is selected from the group consisting of

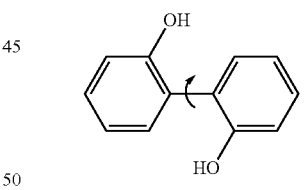

(i.e., 2,2'-biphenol),

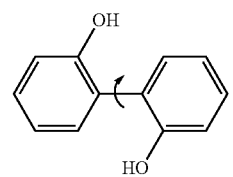

(i.e., 1,1'-dihydroxy-2,2'-binaphthalene), and

34

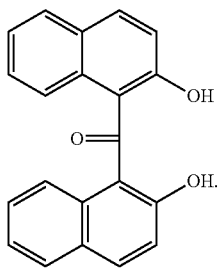

(i.e., bis(2-hydroxy-1-naphthyl)methanone).

The analytical method as described in paragraph [0256], wherein the analyte is a compound selected from the group consisting of amines, diamines, alcohols, amino alcohols, carboxylic acids, amino acids, thiols, aldehydes, ketones, amides, esters, α-hydroxy acids, and any combination thereof.

The analytical method as described in paragraph [0235], wherein a stereodynamic ligand having the formula $A'R'_p Y'_q$ is provided, wherein $A'$ is a an achiral moiety capable of populating one or more chiral conformations or chiral configurations in the presence of the analyte, and wherein the stereoisomeric excess of the analyte in the sample and the concentration of the analyte in the sample are determined.

The analytical method as described in paragraph [0261], wherein the stereodynamic ligand is a meso ligand.

The analytical method as described in paragraph [0262], wherein the stereodynamic ligand is a meso salen or analogue thereof.

The analytical method as described in paragraph [0263], wherein the stereodynamic ligand is

5

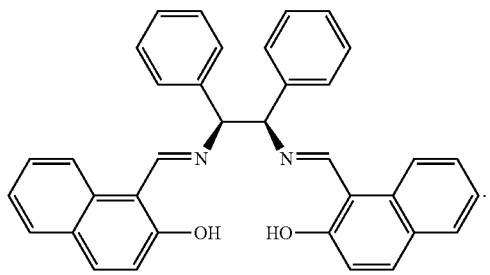

The analytical method as described in paragraph [0261], wherein the analyte is a compound selected from the group consisting of amines, alcohols, amino alcohols, carboxylic acids, amino acids, thiols, aldehydes, ketones, amides, esters, and any combination thereof.

The analytical method as described in paragraph [0265], wherein the analyte is a diamine or an amino alcohol.

The analytical method as described in paragraph [0235], wherein the stereoisomeric excess of the probe-analyte complexes is determined.

The analytical method as described in paragraph [0267], wherein the stereoisomeric excess is determined using circular dichroism spectroscopy, optical rotatory dispersion, or polarimetry.

The analytical method as described in paragraph [0268], wherein the stereoisomeric excess is determined using circular dichroism spectroscopy.

The analytical method as described in paragraph [0267], wherein the analyte is a reaction product and the stereoselectivity of the reaction is determined by determining the stereoisomeric excess of the analyte.

The analytical method as described in paragraph [0235], wherein the concentration of the analyte is determined.

The analytical method as described in paragraph [0271], wherein the concentration is determined using UV spectroscopy, fluorescence spectroscopy, and/or other spectroscopic techniques.

The analytical method as described in paragraph [0272], wherein the concentration is determined using UV spectroscopy.

The analytical method as described in paragraph [0272], wherein the concentration is determined using fluorescence spectroscopy.

The analytical method as described in paragraph [0271], wherein the analyte is a reaction product and the yield of the reaction is determined by determining the concentration of the analyte.

The analytical method as described in paragraph [0235], wherein the absolute configuration of the analyte is determined.

The analytical method as described in paragraph [0235], wherein the stereoisomeric excess of the analyte and the concentration of the analyte are both determined.

The analytical method as described in paragraph [0277] further comprising: determining the individual concentration of any particular stereoisomers present in the sample based on the determined concentration of the analyte and the determined stereoisomeric excess.

The analytical method as described in paragraph [0235], wherein the stereoisomeric excess of the analyte, the concentration of the analyte, and the absolute configuration of the analyte are all determined.

The present invention may be further illustrated by reference to the following examples.

EXAMPLES

Example 1—Synthetic Procedures Generally

All commercially available reagents and solvents were used without further purification. NMR spectra were obtained at 400 MHz ($^1$H NMR) and 100 MHz ($^{13}$C NMR) using $CD_3CN$ or $CDCl_3$ as solvent. Chemical shifts are reported in ppm relative to TMS. Electrospray ionization mass spectra (ESI-MS) were collected on a Thermo Finnigan LCQ instrument. Samples were dissolved in ACN for MS analysis (1 mg/mL).

The compound numbers used in Examples 1-10 refer to the following compounds (where applicable, only one enantiomer is shown). Some of these compounds may be numbered differently in Examples 11-25 and/or Examples 26-32.

1

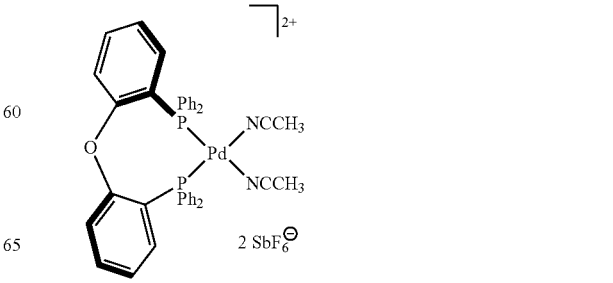

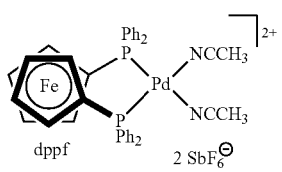
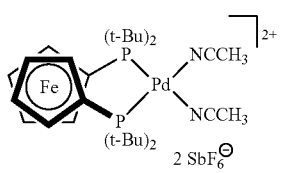
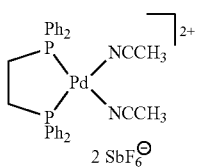
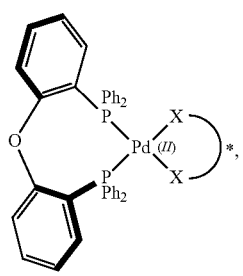
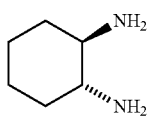
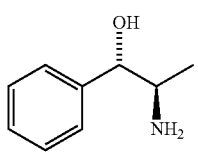
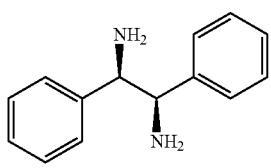
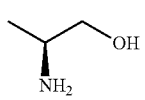
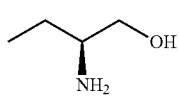
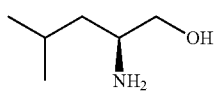

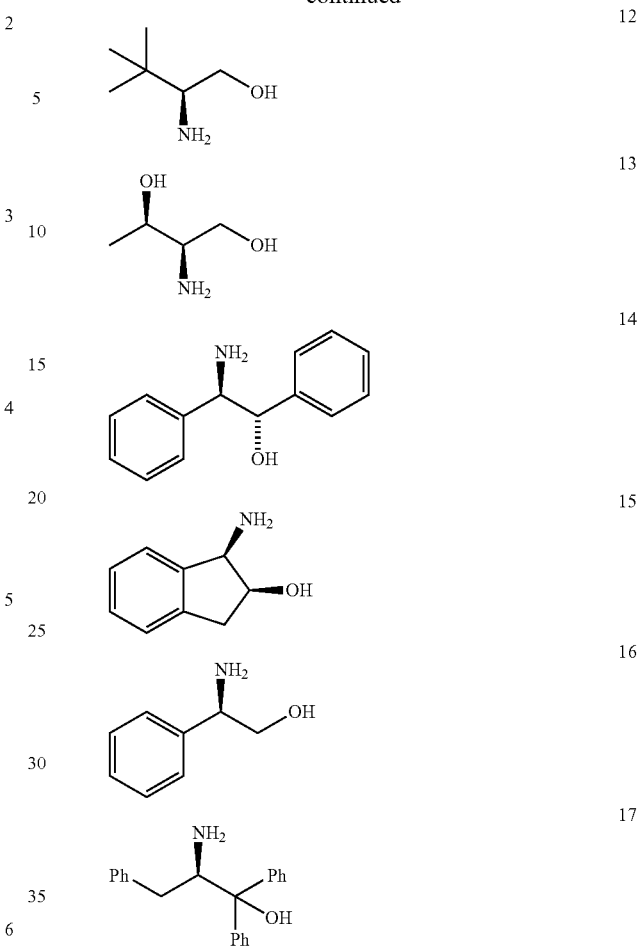

Figure 1B:
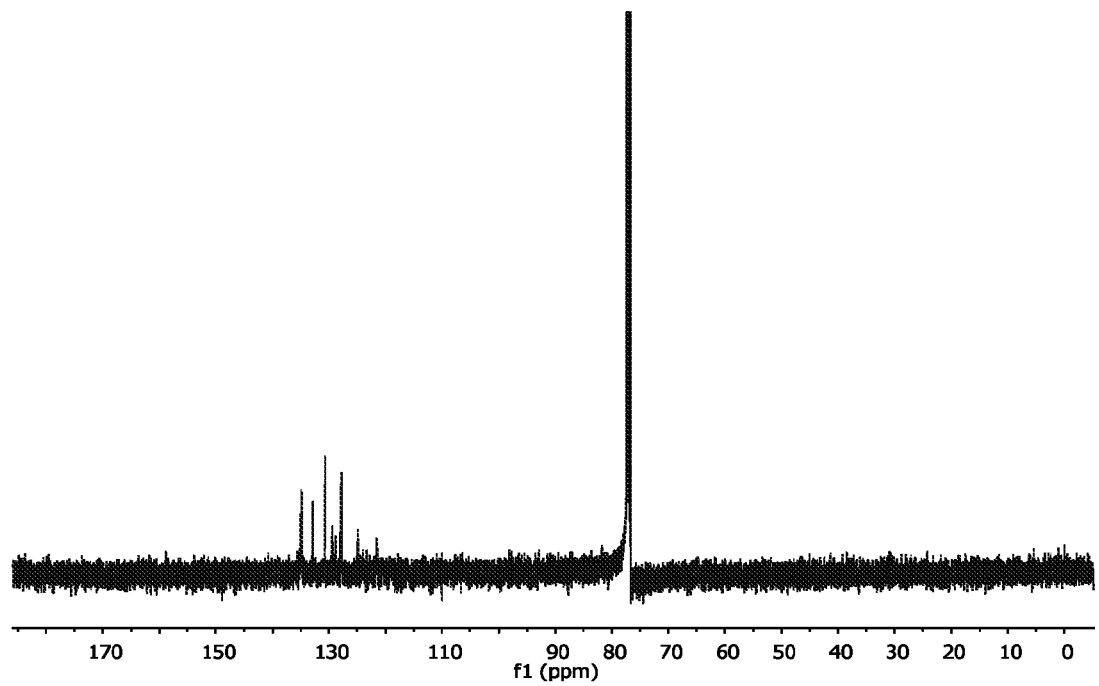

Example 2—Synthesis of [Bis(2-(Diphenylphosphino)Phenyl)Ether]Palladium(II) Dichloride To a solution of (1,5-cyclooctadiene)palladium(II) dichloride (540 mg, 1 mmol) in 25 mL of $CH_2Cl_2$ was added bis[2-(diphenylphosphino)phenyl]ether (285 mg, 1 mmol) dissolved in 6 mL of $CH_2Cl_2$. After stirring at room temperature for 3.5 hours, the mixture was filtrated and the precipitate was washed with 3 mL of $CH_2Cl_2$ followed by 20 mL of hexanes. After drying under vacuum, 586 mg (0.82 mmol, 82%) of [bis(2-(diphenylphosphino)phenyl)ether] palladium(II) dichloride (Bonazzi et al., *J. Am. Chem. Soc.* 132:1432-42 (2010), which is hereby incorporated by reference in its entirety) was obtained. $^1$H NMR ($CDCl_3$) (FIG. 1A): δ=6.73 (dd, J=8.0 Hz, 8.0 Hz, 2H), 6.86 (dd, J=7.5 Hz, 7.5 Hz, 2H), 6.96 (m, 2H), 7.26-7.42 (m, 16H), 7.56-7.63 (m, 6H). $^{13}$C NMR ($CDCl_3$) (FIG. 1B): δ=121.5, 124.9, 127.8, 128.8, 129.4, 130.7, 132.8, 134.9, 135.1.

Example 3—Synthesis of Bis(Acetonitrile)[Bis(2-(Diphenylphosphino)Phenyl)Ether]Palladium(II) Hexafluoroantimonate, 1

Figure 2A:
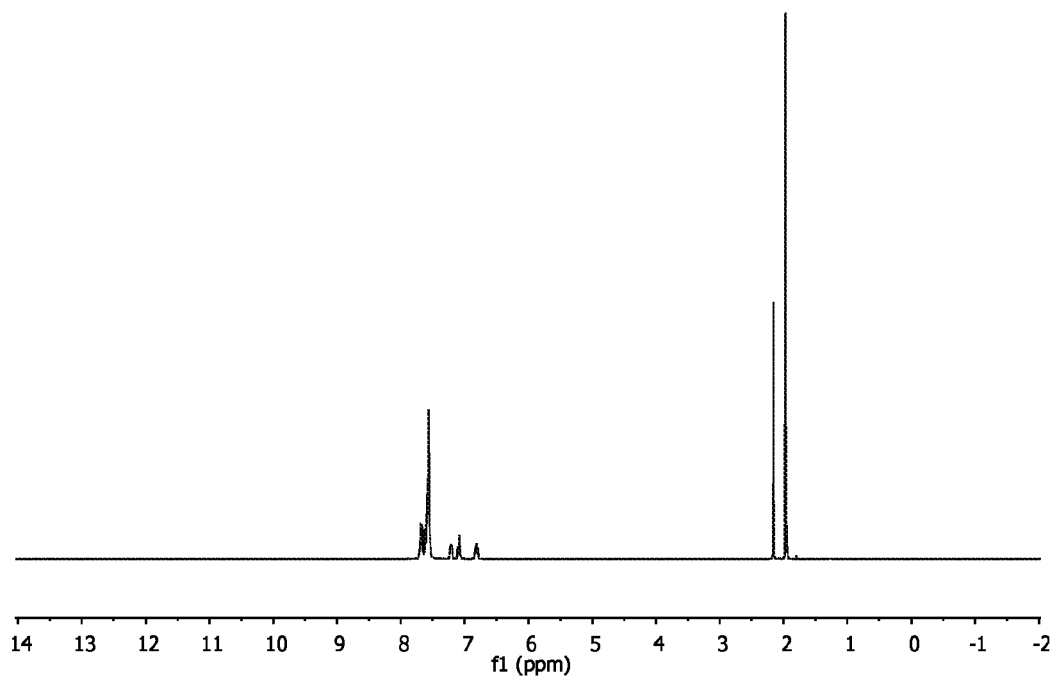
FIGS. 2A-B are $^1$H NMR (FIG. 2A) and $^{13}$C NMR (FIG. 2B) spectra of bis(acetonitrile)[bis(2-(diphenylphosphino)phenyl)ether]palladium(II) hexafluoroantimonate, 1.
Figure 2B:
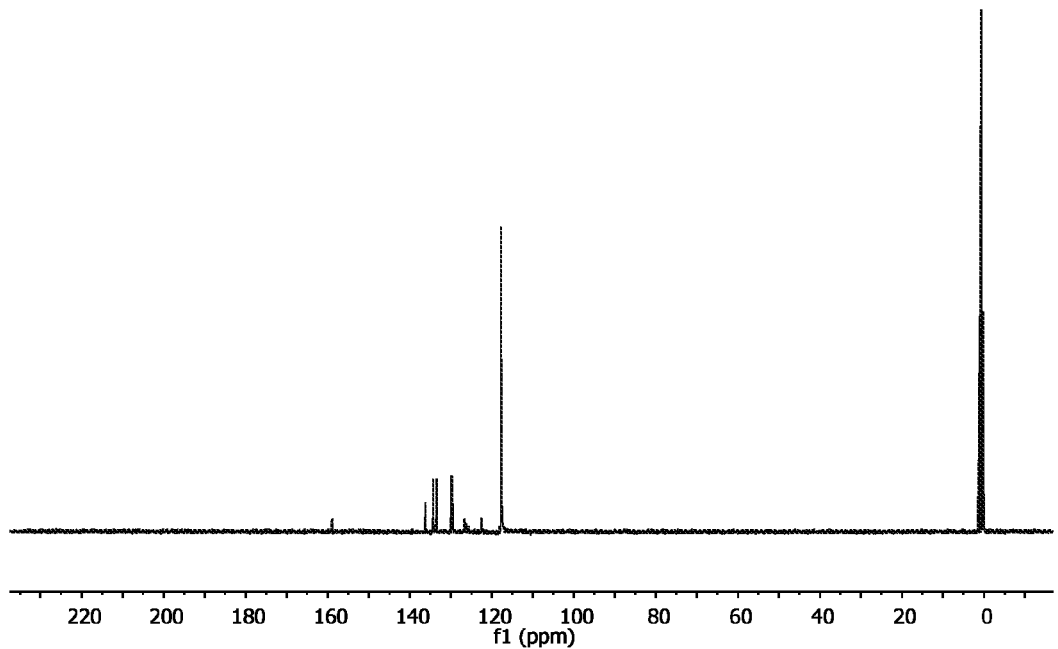

To a solution of [bis(2-(diphenylphosphino)phenyl)ether] palladium(II) dichloride (286 mg, 0.4 mmol) in 5 mL of ACN was added $AgSbF_6$ (274.4 mg, 0.8 mmol, 2 equivalents) dissolved in 3 mL of ACN. After stirring at room temperature for 20 minutes, the mixture was filtrated through a short celite column using CH₂Cl₂ as mobile phase. The solvents were removed and the residue was passed through another celite column using CH₂Cl₂. After redissolving in 3 mL of CH₂Cl₂, recrystallization upon addition of 20 mL of hexanes gave 468 mg (0.4 mmol, 98%) of 1 (Aikawa et al., *Bull. Chem. Soc. Jpn.* 85:201-08 (2012), which is hereby incorporated by reference in its entirety) as a yellow solid. $^1$H NMR (CD₃CN) (FIG. 2A): δ=1.97 (s, 6H), 6.81 (m, 2H), 7.09 (ddd, J=1.2 Hz, 7.4 Hz, 7.4 Hz, 2H), 7.20 (m, 2H), 7.53-7.72 (m, 22H). $^{13}$C NMR (CD₃CN) (FIG. 2B): δ=1.8, 118.9, 123.6, 126.8, 127.4, 127.8, 130.9, 134.7, 135.5, 137.3, 137.4, 160.1. Anal. Calcd. for C₄₀H₃₄F₁₂N₂OP₂PdSb₂: C, 40.08; H, 2.86; N, 2.34. Found: C, 40.44; H, 2.87; N, 2.21.

Example 4—Synthesis of Bis(Acetonitrile)[1,1'-Bis(Diphenylphosphino)Ferrocene]Palladium(II) Hexafluoroantimonate, 2

Figure 3A:
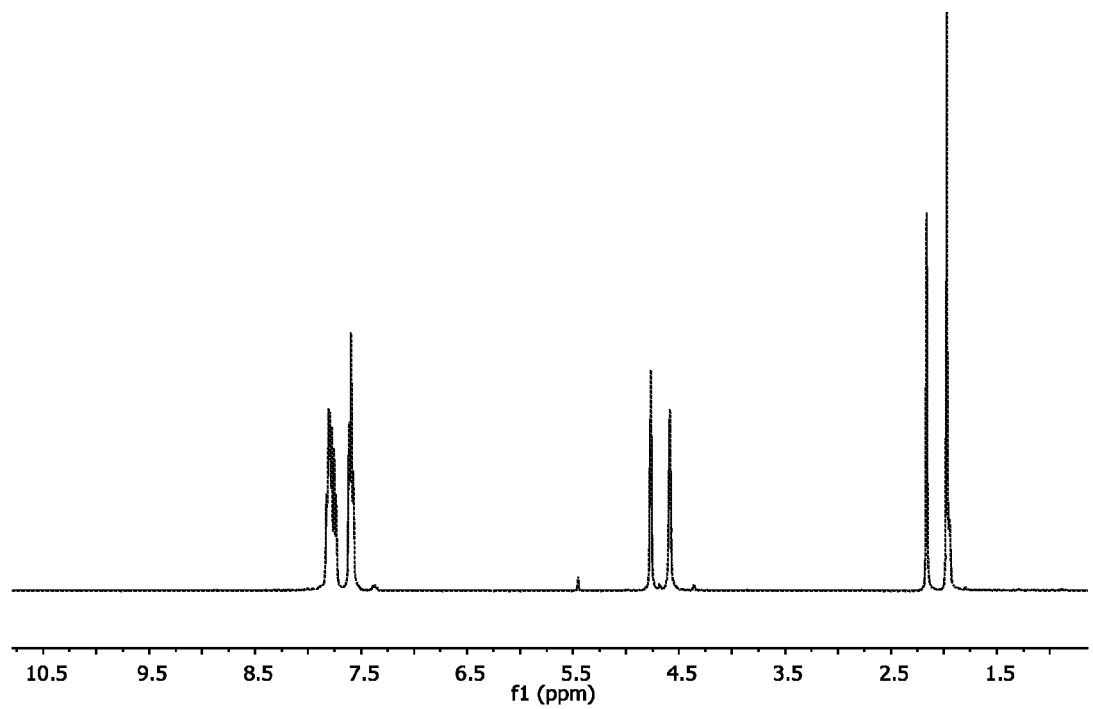
FIGS. 3A-B are $^1$H NMR (FIG. 3A) and $^{13}$C NMR (FIG. 3B) spectra of bis(acetonitrile)[1,1'-bis(diphenylphosphino)ferrocene]palladium(II) hexafluoroantimonate, 2.
Figure 3B:
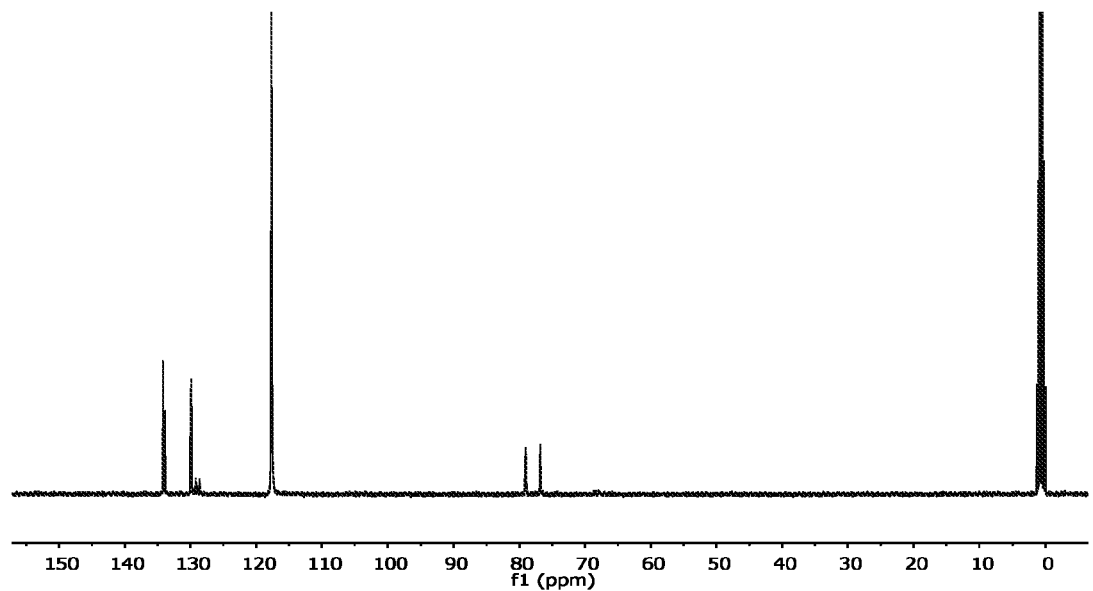
Figure 4:
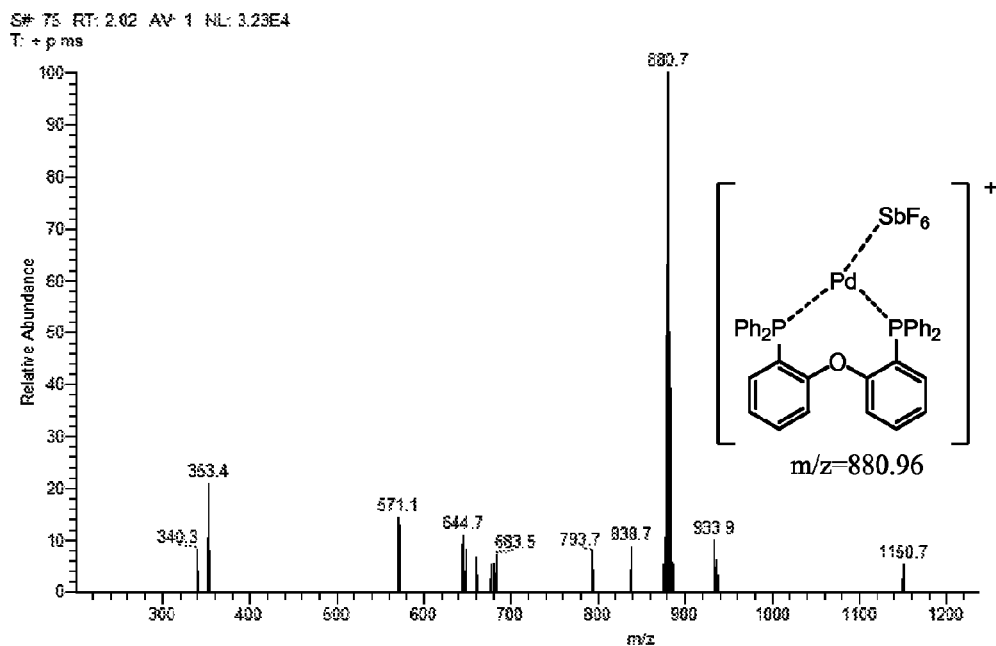
FIG. 4 is the MS spectrum of bis(acetonitrile)[bis(2-(diphenylphosphino)phenyl)ether]palladium(II) hexafluoroantimonate, 1. ESI-MS: m/z=880.7 $(M-2ACN-SbF_6)^+$.
Figure 5:
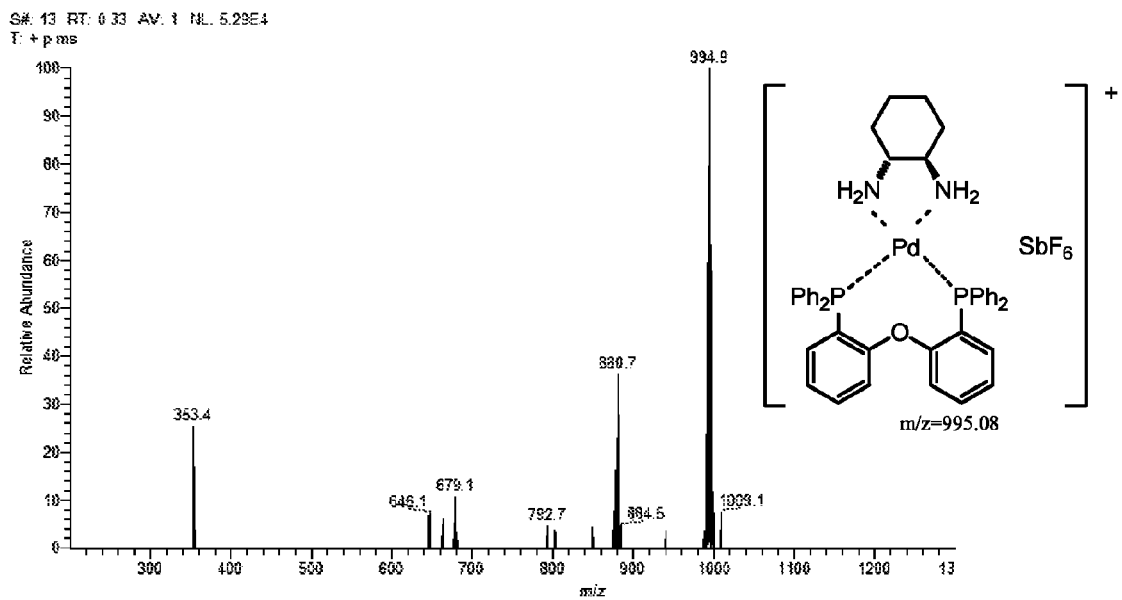
FIG. 5 is the MS spectrum of the complex obtained from 1 and diamine 6. ESI-MS: m/z=994.9 $(M-SbF_6)^+$.
Figure 6:
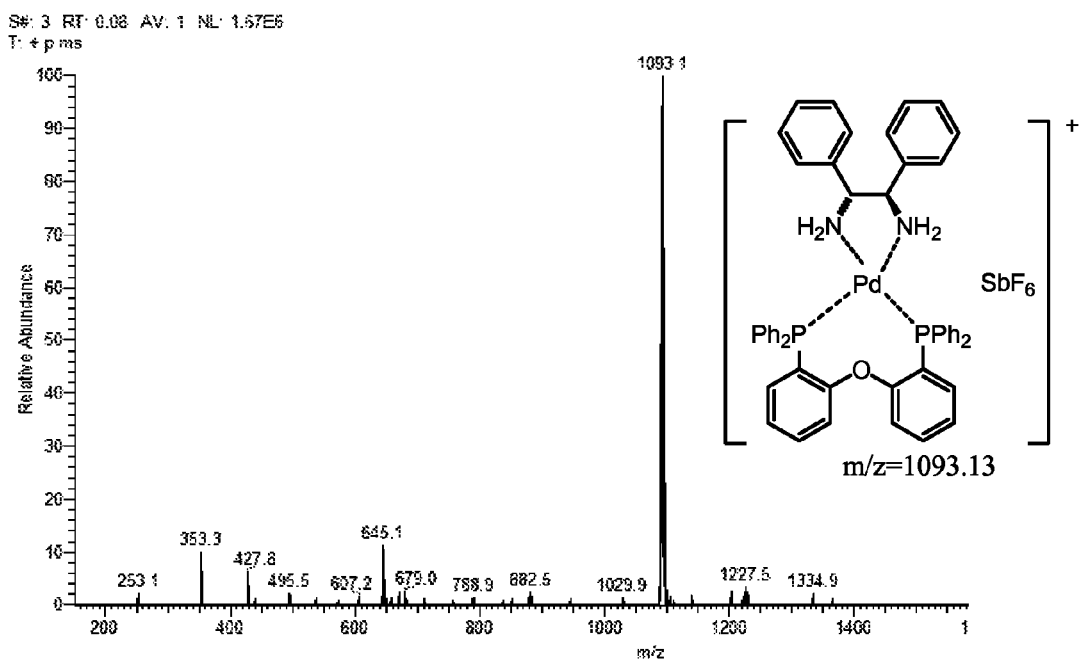
FIG. 6 is the MS spectrum of the complex obtained from 1 and diamine 8. ESI-MS: m/z=1093.1 $(M-SbF_6)^+$.
Figure 7:
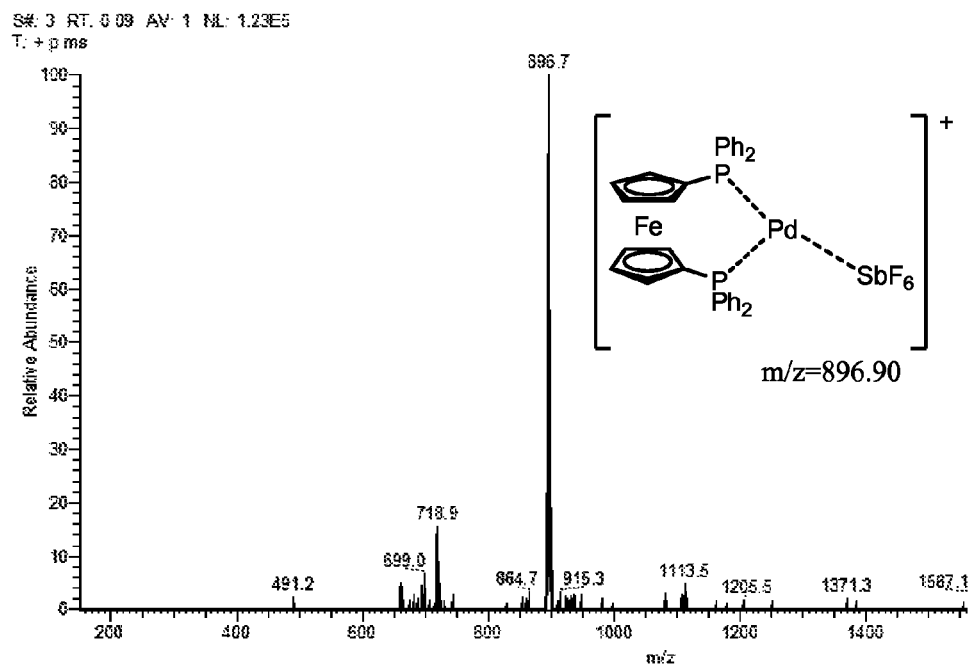
FIG. 7 is the MS spectrum of bis(acetonitrile)[1,1'-bis(diphenylphosphino)ferrocene]palladium(II) hexafluoroantimonate, 2. ESI-MS: m/z=896.7 $(M-2ACN-SbF_6)^+$.
Figure 8:
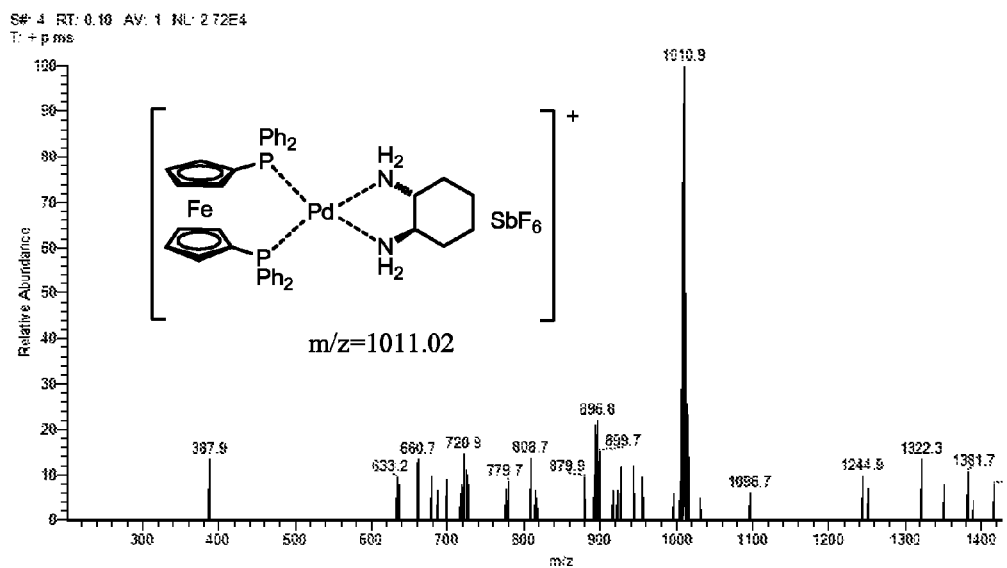
FIG. 8 is the MS spectrum of the complex obtained from 2 and diamine 6. ESI-MS: m/z=1010.9 $(M-SbF_6)^+$.
Figure 9:
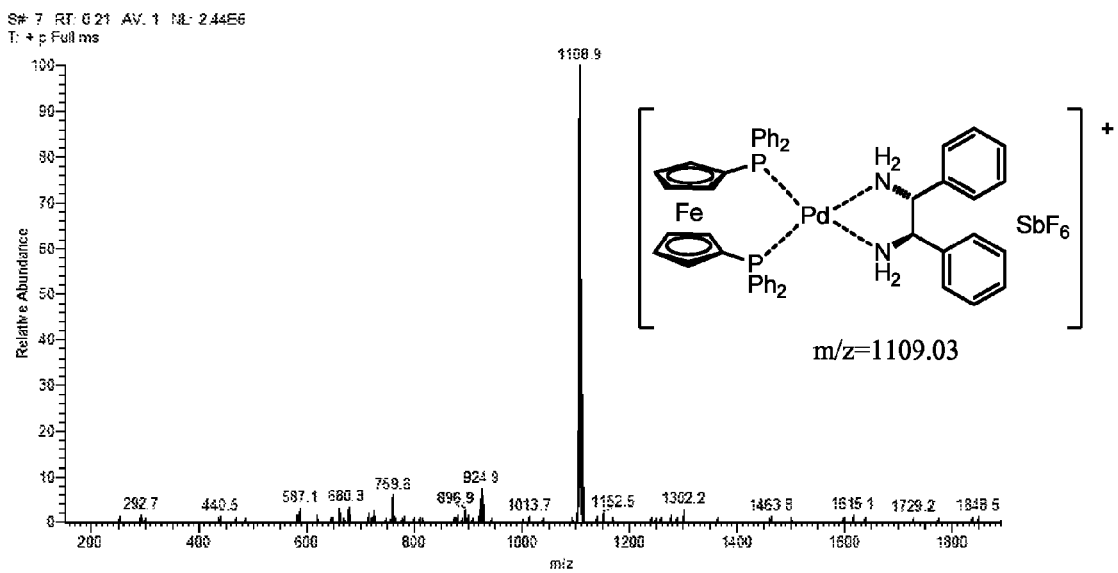
FIG. 9 is the MS spectrum of the complex obtained from 2 and diamine 8. ESI-MS: m/z=1108.9 $(M-SbF_6)^+$.

To a solution of AgSbF₆ (75.6 mg, 0.22 mmol, 2.2 equivalents) in 3 mL of ACN was added 81.6 mg (0.1 mmol) of [1,1'-bis(diphenylphosphino)ferrocene]palladium(II) dichloride (complex with dichloromethane) under nitrogen. After stirring at room temperature for 30 minutes, the mixture was filtrated through a short celite column using CH₂Cl₂ as mobile phase. The solvents were removed and then residue was passed through another celite column using CH₂Cl₂. Removal of solvents gave 118 mg (0.1 mmol, 98%) of 2 (Mikami & Aikawa, *Org. Lett.* 4:99-101 (2002), which is hereby incorporated by reference in its entirety) as a purple solid. $^1$H NMR (CD₃CN) (FIG. 3A): δ=1.97 (s, 6H), 4.57 (s, 4H), 4.77 (s, 4H), 7.56-7.62 (m, 8H), 7.72-7.83 (m, 12H). $^{13}$C NMR (CD₃CN) (FIG. 3B): δ=1.8, 69.0, 78.0, 80.2, 118.9, 130.2, 131.3, 135.2, 135.4.

Example 5—Sensing Experiments Generally

A stock solution of sensor 1 or 2 (0.01 M) in ACN was prepared and 100 μL of this solution was placed into a 4-mL vial. Then, solutions of substrates (0.01 M for diamines and 0.02 M for amino alcohols) in ACN were prepared, and 100 μL of a substrate solution was placed in the vial containing 100 μL of the sensor stock solution. The following amines and amino alcohols (only one enantiomer shown) were analyzed.

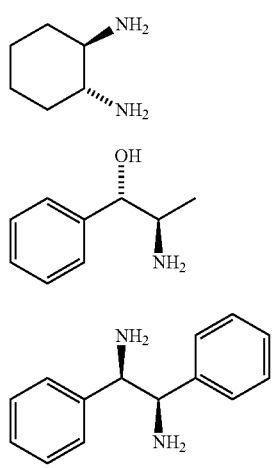

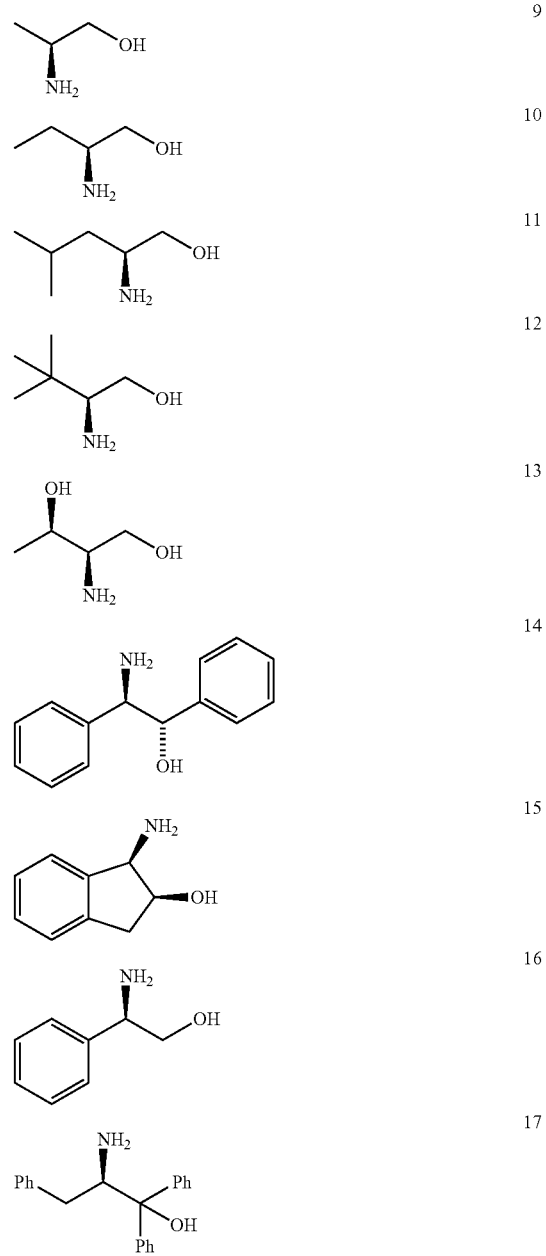

Example 6—MS and NMR Analysis of the Substrate Coordination

Figure 10:
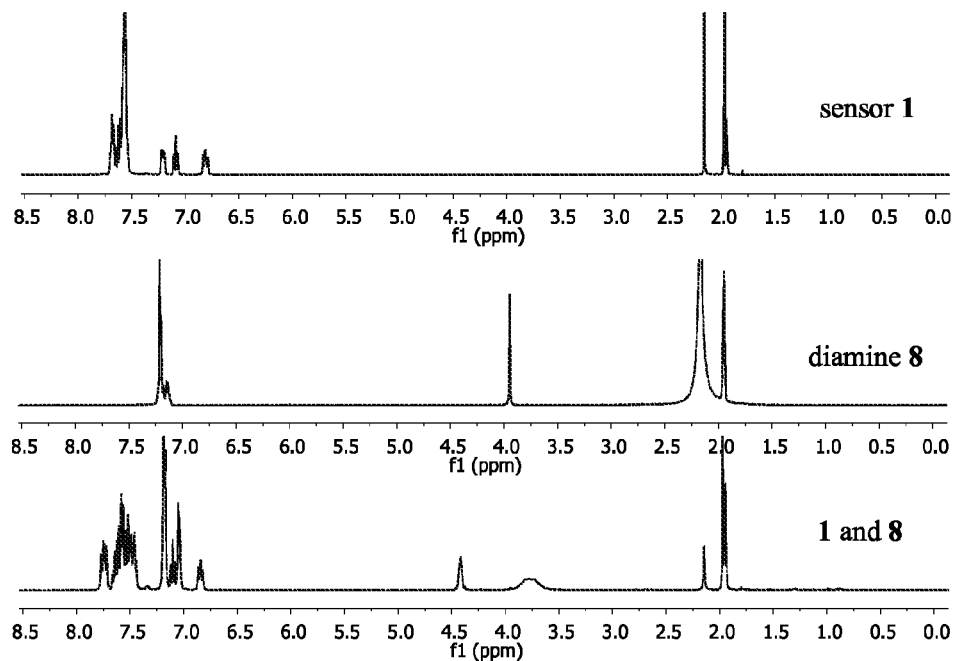
FIG. 10 is $^1$H NMR spectra of sensor 1 (top), diamine 8 (middle), and a 1:1 mixture (bottom) in $CD_3CN$.
Figure 11:
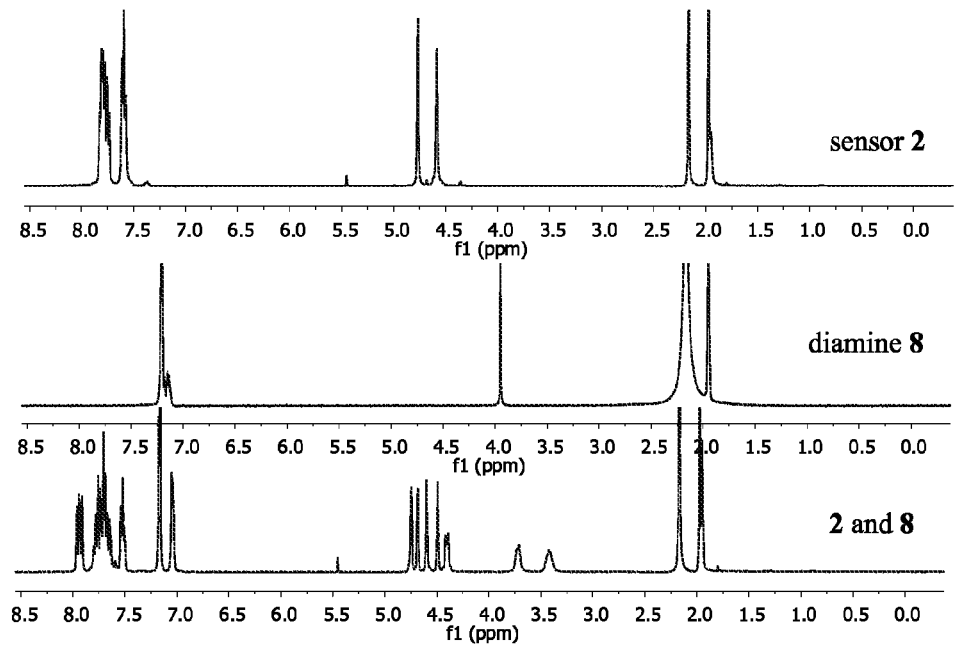
FIG. 11 is the $^1$H NMR spectra of sensor 2 (top), diamine 8 (middle), and a 1:1 mixture (bottom) in $CD_3CN$.
Figure 12:
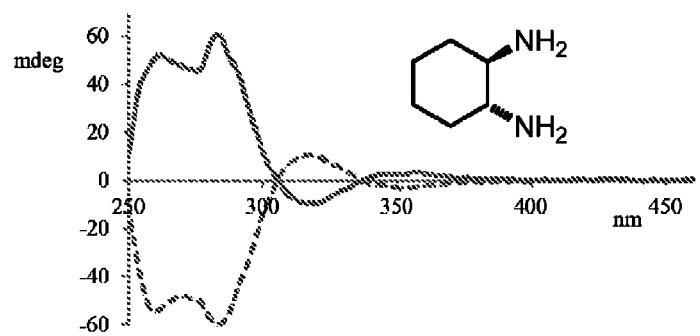
FIG. 12 is the CD spectra of the complex formed from 1 and (1R,2R)-6 (solid line) or (1S,2S)-6 (dashed line) in ACN ($1.25\times10^{-4}$ M).
Figure 13:
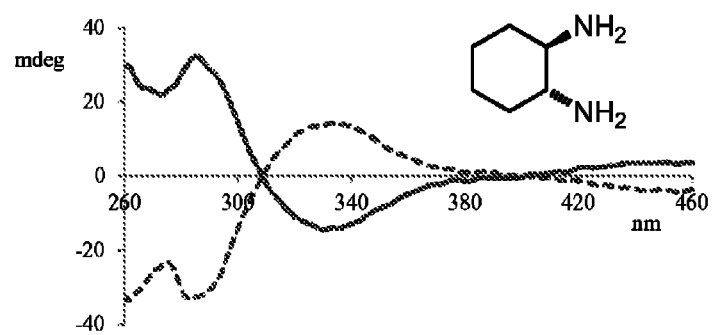
FIG. 13 is the CD spectra of the complex formed from 2 and (1R,2R)-6 (solid line) or (1S,2S)-6 (dashed line) in ACN ($1.25\times10^{-4}$ M).
Figure 14:
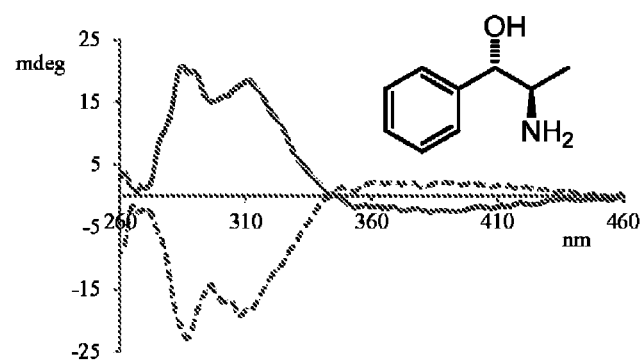
FIG. 14 is the CD spectra of the complex formed from 1 and (1R,2S)-7 (solid line) or (1S,2R)-7 (dashed line) in ACN ($1.25\times10^{-4}$ M).
Figure 15:
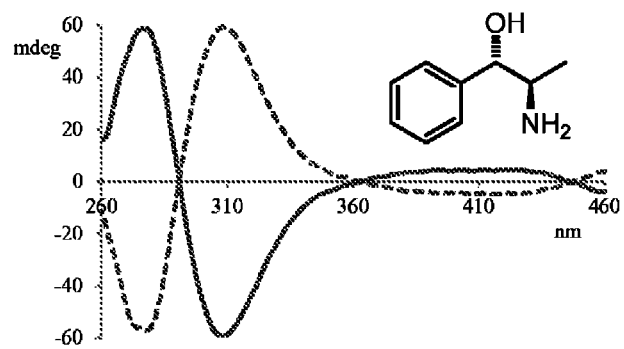
FIG. 15 is the CD spectra of the complex formed from 2 and (1R,2S)-7 (solid line) or (1S,2R)-7 (dashed line) in ACN ($1.25\times10^{-4}$ M).
Figure 16:
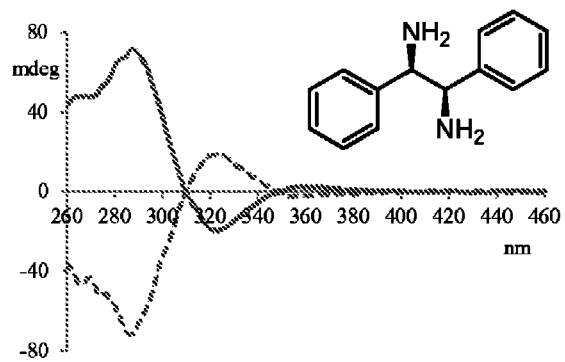
FIG. 16 is the CD spectra of the complex formed from 1 and (1R,2R)-8 (solid line) or (1S,2S)-8 (dashed line) in ACN ($1.25\times10^{-4}$ M).
Figure 17:
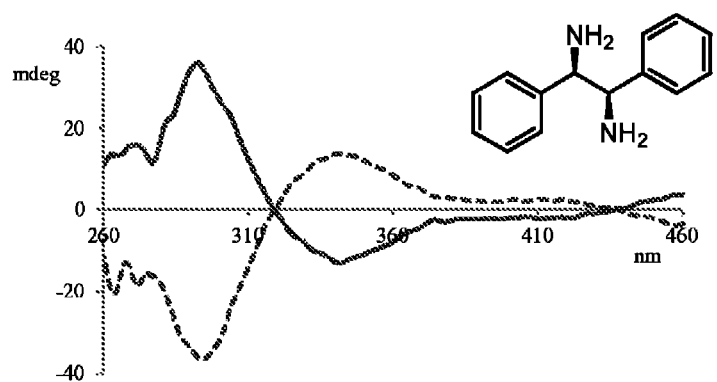
FIG. 17 is the CD spectra of the complex formed from 2 and (1R,2R)-8 (solid line) or (1S,2S)-8 (dashed line) in ACN ($1.25\times10^{-4}$ M).
Figure 18:
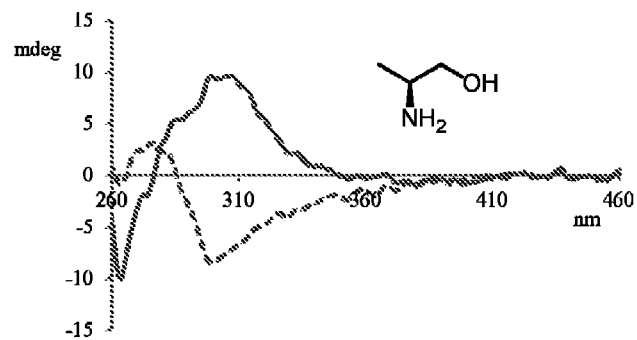
FIG. 18 is the CD spectra of the complex formed from 1 and (R)-9 (solid line) or (S)-9 (dashed line) in ACN ($1.25\times10^{-4}$ M).
Figure 19:
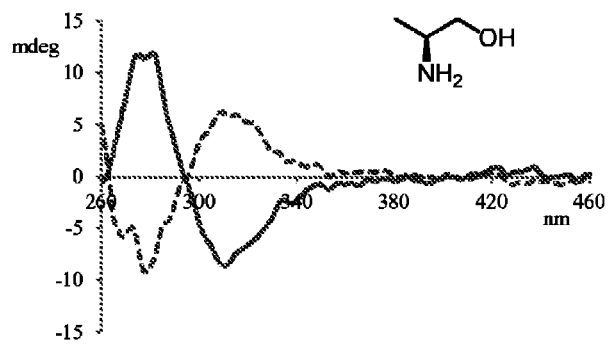
FIG. 19 is the CD spectra of the complex formed from 2 and (R)-9 (solid line) or (S)-9 (dashed line) in ACN ($1.25\times10^{-4}$ M).
Figure 20:
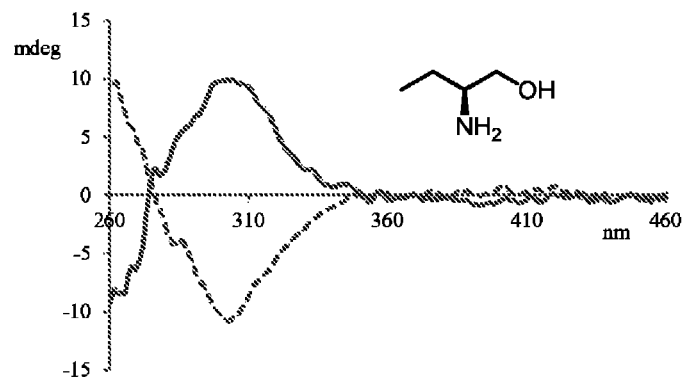
FIG. 20 is the CD spectra of the complex formed from 1 and (R)-10 (solid line) or (S)-10 (dashed line) in ACN ($1.25\times10^{-4}$ M).
Figure 21:
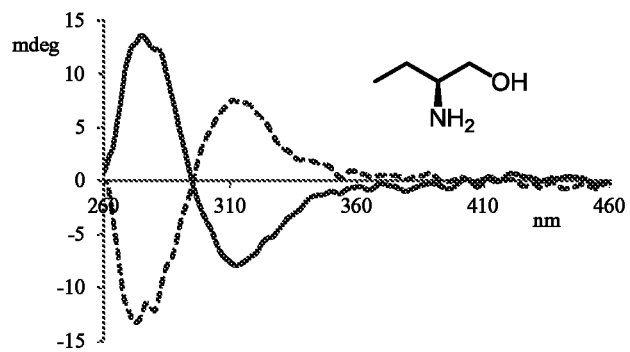
FIG. 21 is the CD spectra of the complex formed from 2 and (R)-10 (solid line) or (S)-10 (dashed line) in ACN ($1.25\times10^{-4}$ M).
Figure 22:
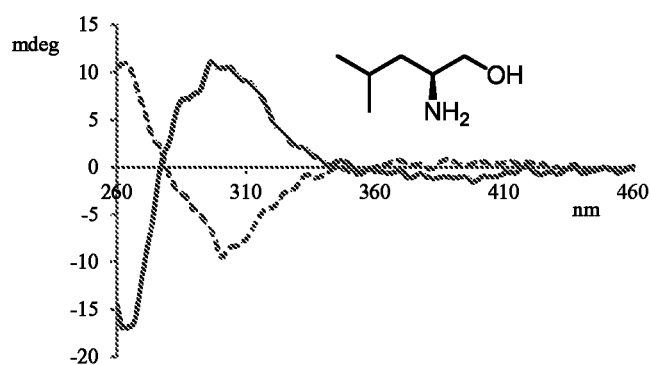
FIG. 22 is the CD spectra of the complex formed from 1 and (R)-11 (solid line) or (S)-11 (dashed line) in ACN ($1.25\times10^{-4}$ M).
Figure 23:
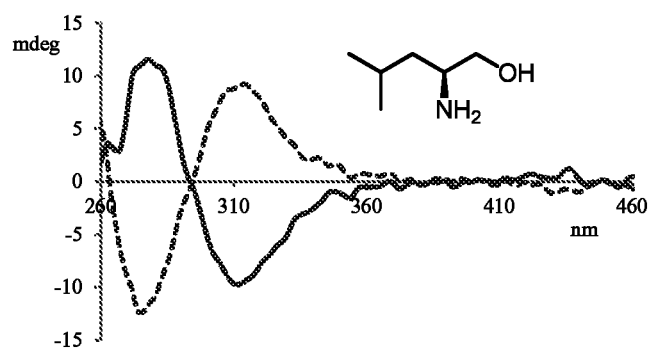
FIG. 23 is the CD spectra of the complex formed from 2 and (R)-11 (solid line) or (S)-11 (dashed line) in ACN ($1.25\times10^{-4}$ M).
Figure 24:
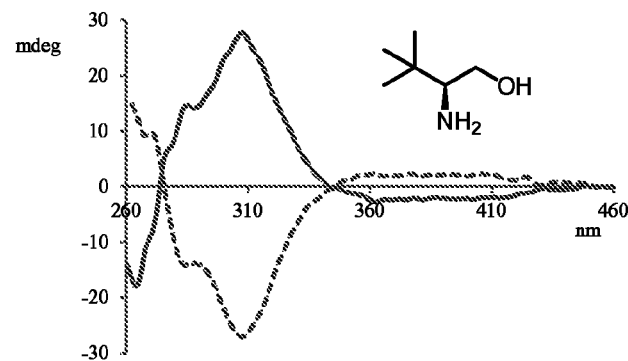
FIG. 24 is the CD spectra of the complex formed from 1 and (R)-12 (solid line) or (S)-12 (dashed line) in ACN ($1.25\times10^{-4}$ M).
Figure 25:
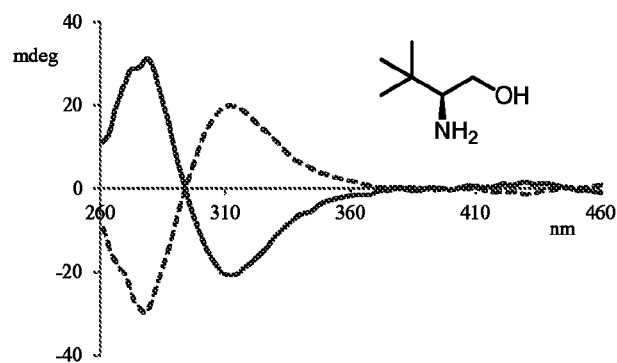
FIG. 25 is the CD spectra of the complex formed from 2 and (R)-12 (solid line) or (S)-12 (dashed line) in ACN ($1.25\times10^{-4}$ M).
Figure 26:
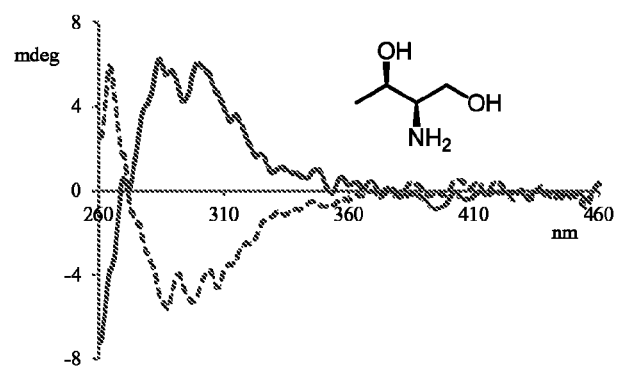
FIG. 26 is the CD spectra of the complex formed from 1 and (2R,3R)-13 (solid line) or (2S,3S)-13 (dashed line) in ACN ($1.25\times10^{-4}$ M).
Figure 27:
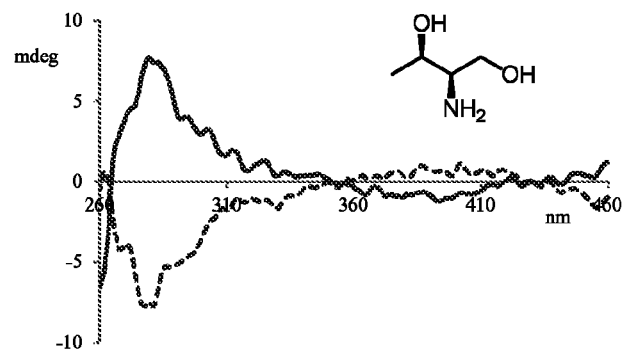
FIG. 27 is the CD spectra of the complex formed from 2 and (2R,3R)-13 (solid line) or (2S,3S)-13 (dashed line) in ACN ($1.25\times10^{-4}$ M).
Figure 28:
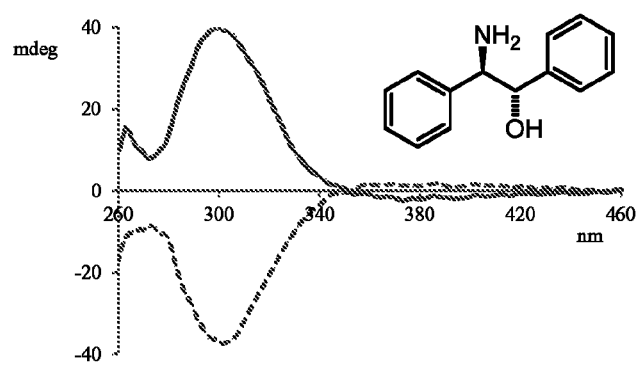
FIG. 28 is the CD spectra of the complex formed from 1 and (1R,2S)-14 (solid line) or (1S,2R)-14 (dashed line) in ACN ($1.0\times10^{-4}$ M).
Figure 29:
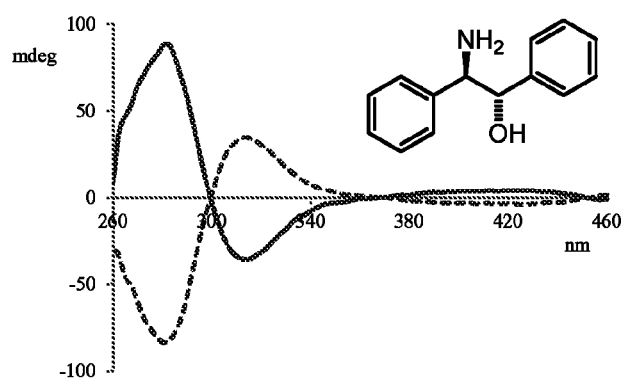
FIG. 29 is the CD spectra of the complex formed from 2 and (1R,2S)-14 (solid line) or (1S,2R)-14 (dashed line) in ACN ($1.25\times10^{-4}$ M).
Figure 30:
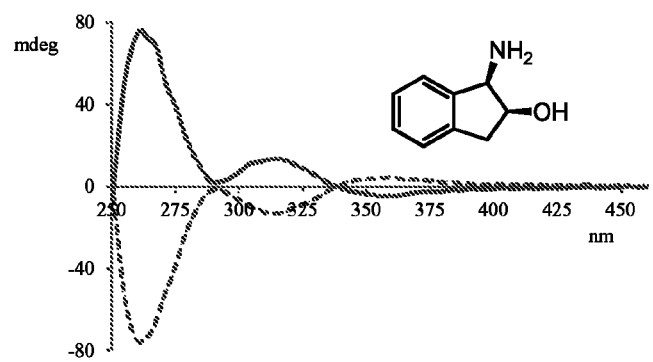
FIG. 30 is the CD spectra of the complex formed from 1 and (1S,2R)-15 (solid line) or (1R,2S)-15 (dashed line) in ACN ($1.0\times10^{-4}$ M).
Figure 31:
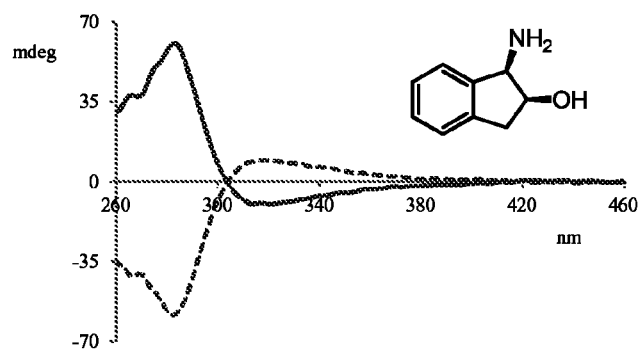
FIG. 31 is the CD spectra of the complex formed from 2 and (1S,2R)-15 (solid line) or (1R,2S)-15 (dashed line) in ACN ($1.25\times10^{-4}$ M).
Figure 32:
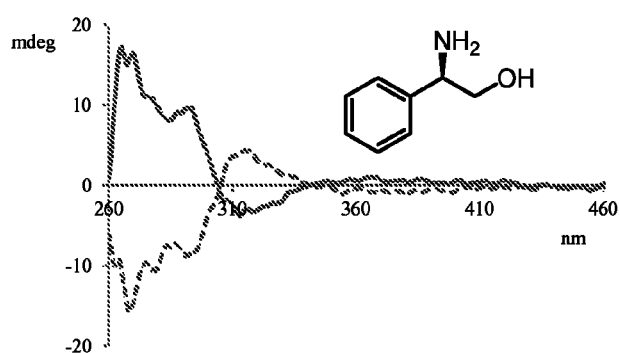
FIG. 32 is the CD spectra of the complex formed from 1 and (S)-16 (solid line) or (R)-16 (dashed line) in ACN ($1.25\times10^{-4}$ M).
Figure 33:
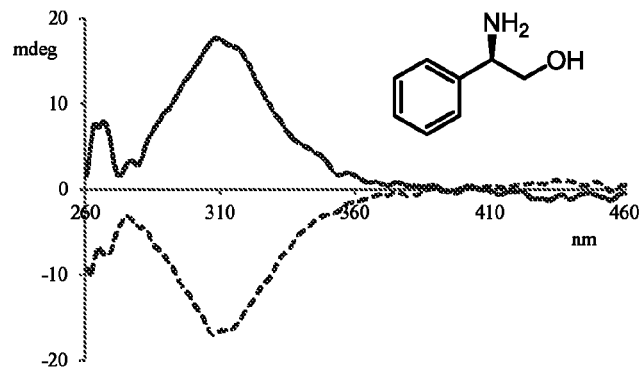
FIG. 33 is the CD spectra of the complex formed from 2 and (S)-16 (solid line) or (R)-16 (dashed line) in ACN ($1.25\times10^{-4}$ M).
Figure 34:
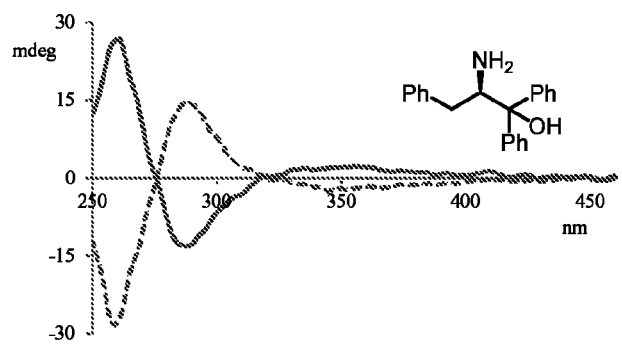
FIG. 34 is the CD spectra of the complex formed from 1 and (R)-17 (solid line) or (S)-17 (dashed line) in ACN (7.5×10⁻⁵M).
Figure 35:
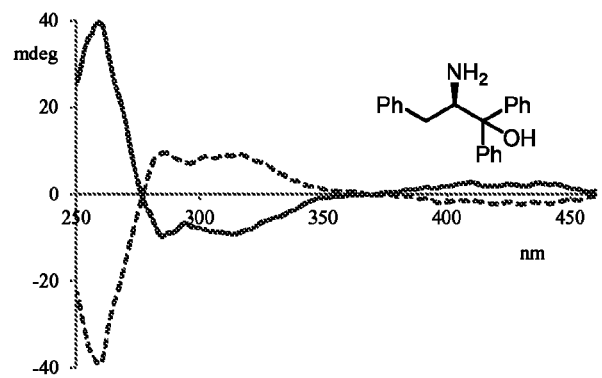
FIG. 35 is the CD spectra of the complex formed from 2 and (R)-17 (solid line) or (S)-17 (dashed line) in ACN (1.0×10⁻⁴M).
Figure 36:
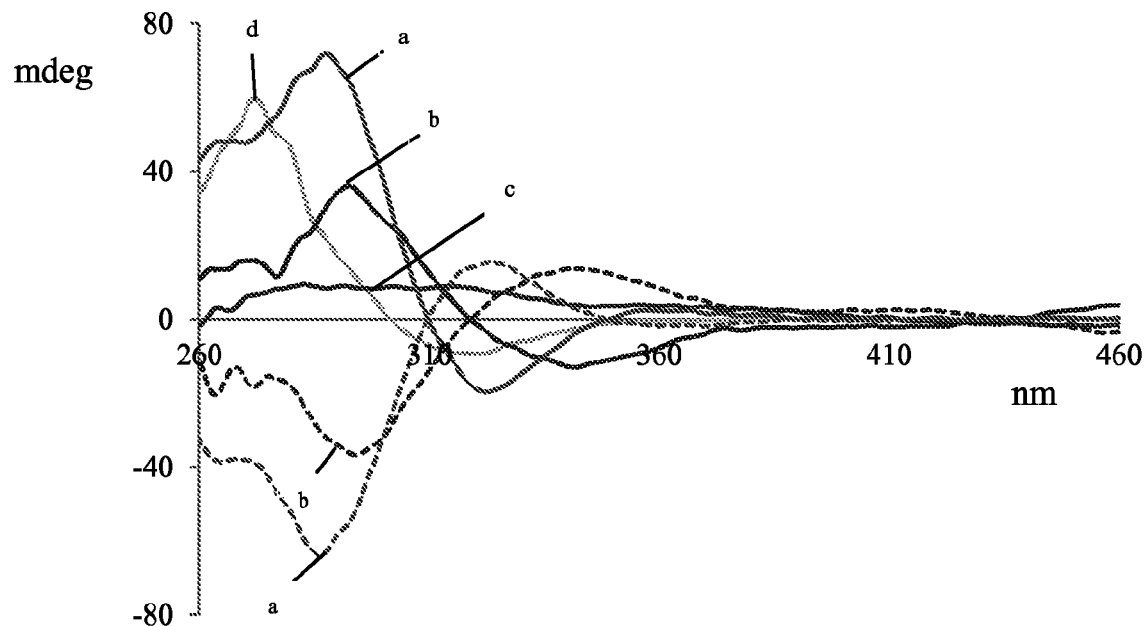
FIG. 36 is the CD spectra of the complexes obtained upon addition of diamine 8 to Pd complexes 1-4 in ACN (1.25×10⁻⁴ M). green (a): 1 and 8; red (b): 2 and 8; purple (c): 3 and 8; yellow (d): 4 and 8 (7.5×10⁻⁵ M).

MS analysis in ACN (1 mg/mL) of a mixture containing the palladium complex 1 or 2 and either diamine 6 or 8 showed formation of a 1:1 complex. Mass spectrometric detection of the corresponding amino alcohol complexes was unsuccessful due to the formation of a palladium hydride species formed through oxidation of the alcohol group. The coordination of the substrate to the palladium center was also evident by NMR analysis. See FIGS. 4-9 (MS spectra) and FIGS. 10-11 ($^1$H NMR spectra).

Example 7—CD Spectroscopy

The mixture described in Example 5, supra, was diluted to 1.25×10⁻⁴ M for CD analysis unless noted otherwise. CD spectra were collected with a standard sensitivity of 100 mdeg, a data pitch of 0.5 nm, a band width of 1 nm, a scanning speed of 500 nm/s, and a response of 0.5 s using a quartz cuvette (1 cm path length). The data were baseline corrected and smoothed using a binomial equation. See FIGS. 12-38.

Example 8—Calibration Curve and Ee Determination Using Palladium Complex 2 and Amino Alcohol 7

Figure 39:
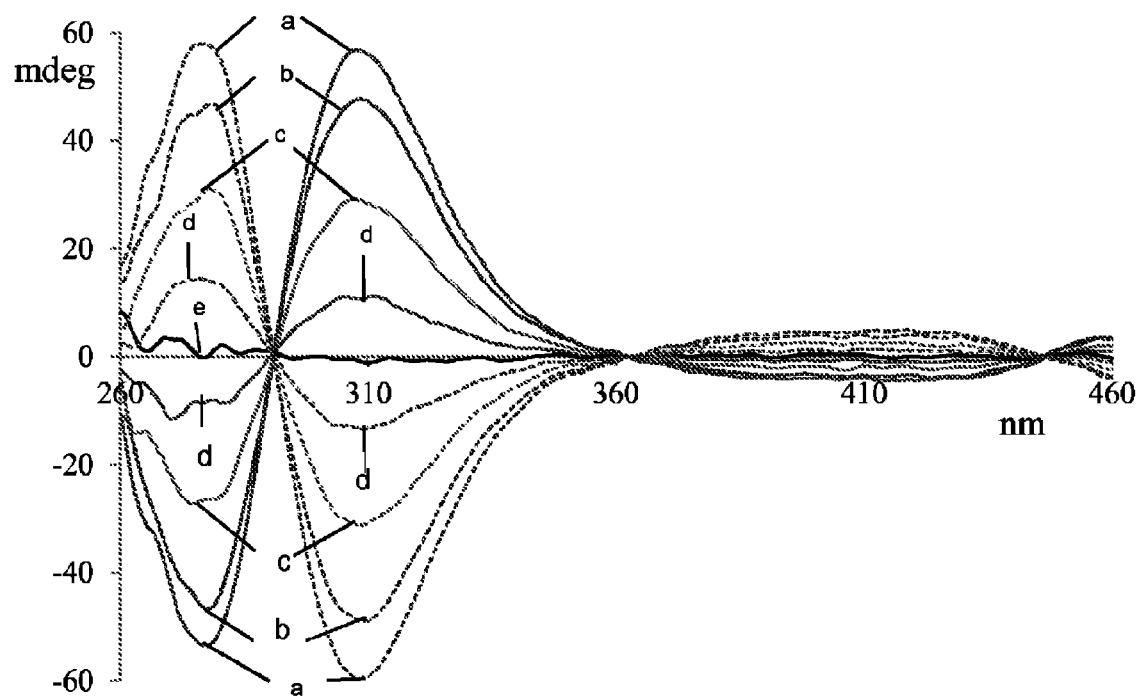
FIG. 39 is the CD spectra of the complex formed from sensor 2 and (1S,2R)-7 (solid lines) and its enantiomer (dashed lines) with varying ee. Red (a): 100% ee; blue (b): 80% ee; green (c): 50% ee; purple (d): 20% ee; black (e): 0% ee. CD measurements were performed at 1.25×10⁻⁴ M in ACN at 25° C.
Figure 40:
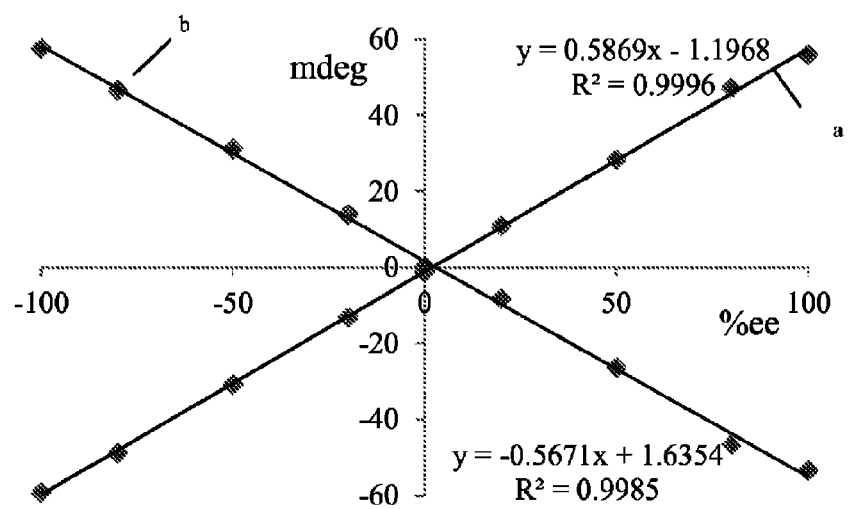
FIG. 40 is a plot of CD amplitude at 310.0 nm and 278.0 nm versus % ee of 7. Red (a): 310.0 nm; blue (b): 278.0 nm.

To determine the practical use of the sensors, the chiroptical response of palladium complex 2 to the coordination of amino alcohol 7 was investigated. Stoichiometric mixtures were prepared in ACN ($1.25 \times 10^{-4}$ M) with varying ee of substrate 7 (100%, 80%, 50%, 20%, 0%, −20%, −50%, −80%, −100%) (FIG. 39). The CD amplitudes (mdeg) at 310.0 nm and 278.0 nm were plotted versus % ee (FIG. 40). The calibration curves showed a linear relationship at both wavelengths ($mdeg_{310\ nm} = 0.5869 \times ee - 1.1968$, $R^2=0.9996$, $mdeg_{278\ nm} = -0.5671 \times ee + 1.6354$, $R^2=0.9985$).

Five scalemic samples of amino alcohol 7 with varying ee were prepared and treated with 2 as described above. Using the linear equation developed above and measuring the CD amplitudes at 310.0 nm and 278.0 nm, the ee of the samples was determined. Experimentally obtained average data were within 3.0% of the actual values. See Table 1.

TABLE 1

Experimental vs. actual ee's of 5 scalemic samples of amino alcohol 7 determined with Pd complex 2.

| Actual ee % | Calculated % ee at 310.0 nm | Calculated % ee at 278.0 nm | Average % ee |
|---|---|---|---|
| 60.0 | 62.0 | 64.0 | 63.0 |
| 40.0 | 42.3 | 40.9 | 41.6 |
| 30.0 | 31.0 | 33.9 | 32.0 |
| −40.0 | −40.3 | −41.1 | −40.7 |
| −60.0 | −61.2 | −61.2 | −61.2 |

Example 9—Linear CD Response Using Palladium Complex 1 and Diamine 8

Figure 41:
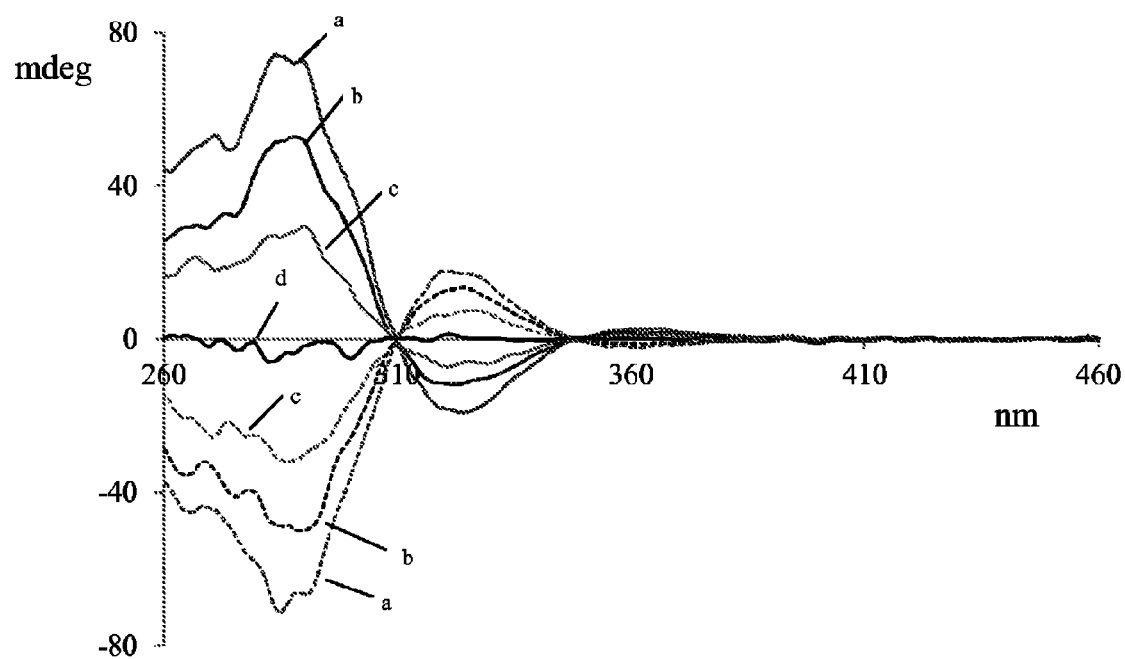
FIG. 41 is the CD spectra of the complex formed from 1 and 8 with varying ee in ACN (1.25×10–4 M). Red (a): 100% ee; blue (b): 70% ee; green (c): 40% ee; black (d): 0% ee.
Figure 42:
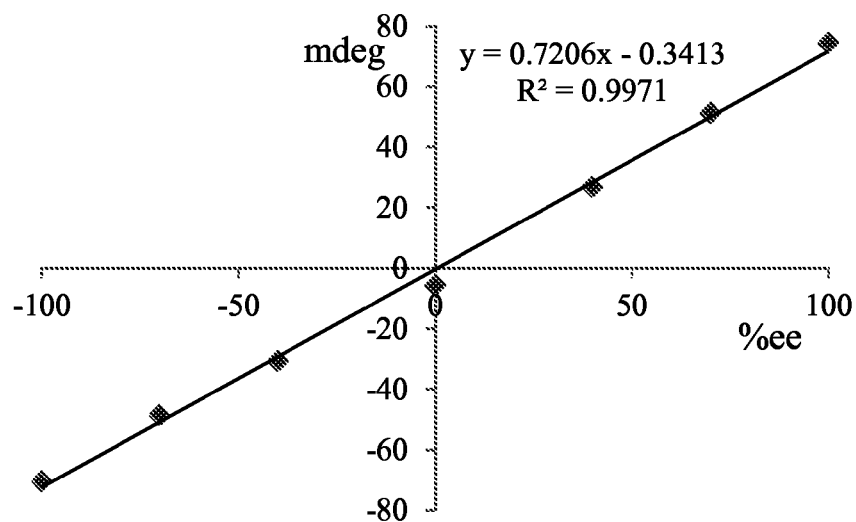
FIG. 42 is a plot of CD amplitude at 284.0 nm versus % ee of 8.

The chiroptical response of 1 to the coordination of diamine 8 was investigated. Solutions containing equimolar amount of the sensor and the substrate with varying ee (100%, 70%, 40%, 0%, −40%, −70%, −100%) in ACN ($1.25 \times 10^{-4}$ M) were prepared (FIG. 41). The CD amplitude (mdeg) at 284.0 nm was plotted versus % ee (FIG. 42). The calibration curve showed a linear relationship ($mdeg = 0.7206 \times ee - 0.3413$, $R^2 = 0.9971$).

Example 10—Determination of Both Enantiomeric Excess and Concentration of Diamine 6 Using Sensor 1

Figure 43:
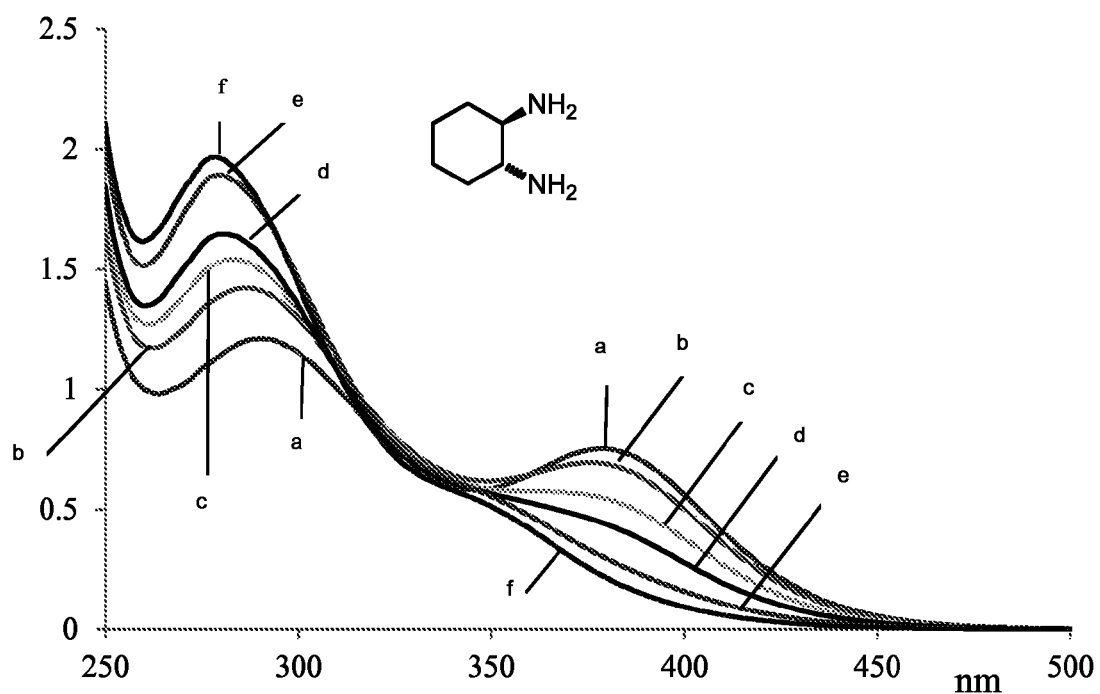
FIG. 43 is the UV-Vis spectra of sensor 1 (1.25×10⁻⁴ M) upon addition of various amounts of diamine 6 in ACN. Red (a): 0 equiv.; green (b): 0.2 equiv.; orange (c): 0.4 equiv.; black (d): 0.6 equiv.; purple (3): 0.8 equiv.; blue (f): 1.0 equiv.
Figure 44:
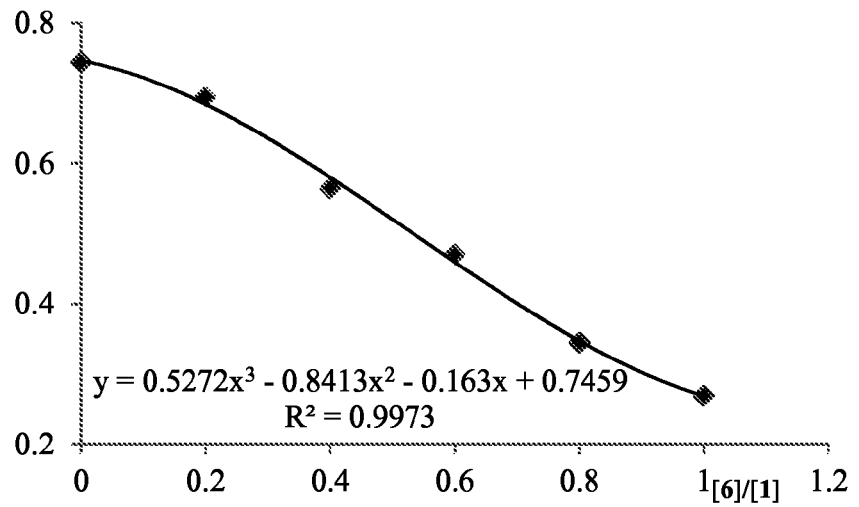
FIG. 44 is a plot of the absorption maximum at 374 nm versus equivalents of 6.

To investigate the possibility of determination of the concentration and ee, a UV calibration curve was plotted using 1 ($1.25 \times 10^{-4}$ M) and diamine 6 with varying ratio (0.0/0.2/0.4/0.6/0.8/1.0 equivalent) (FIG. 43). The calibration curve showed a sigmoidal relationship at 374.0 nm ($A = 0.5272[6/1]^3 - 0.8413[6/1]^2 - 0.163[6/1] + 0.7459$, $R^2 = 0.9973$) (FIG. 44).

Figure 45:
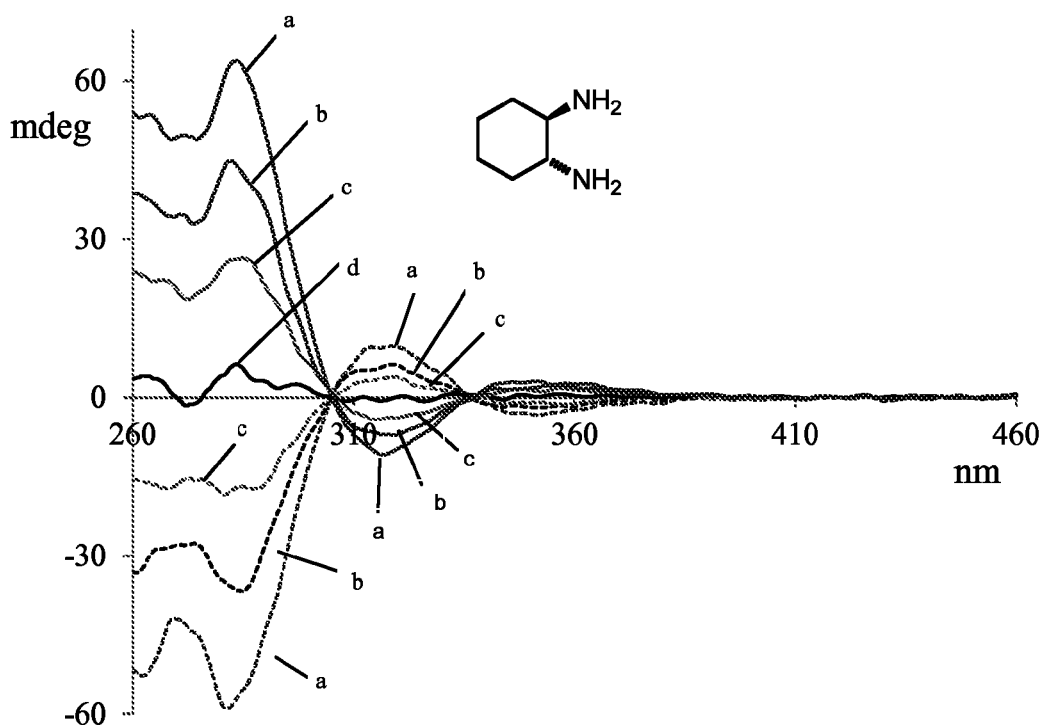
FIG. 45 is the CD spectra of the complex formed from 1 and 6 with varying ee. Red (a): 100% ee; blue (b): 70% ee; green (c): 40% ee; black (d): 0% ee. All measurements were performed using 1 in acetonitrile (1.25 10⁻⁴ M) at room temperature.
Figure 46:
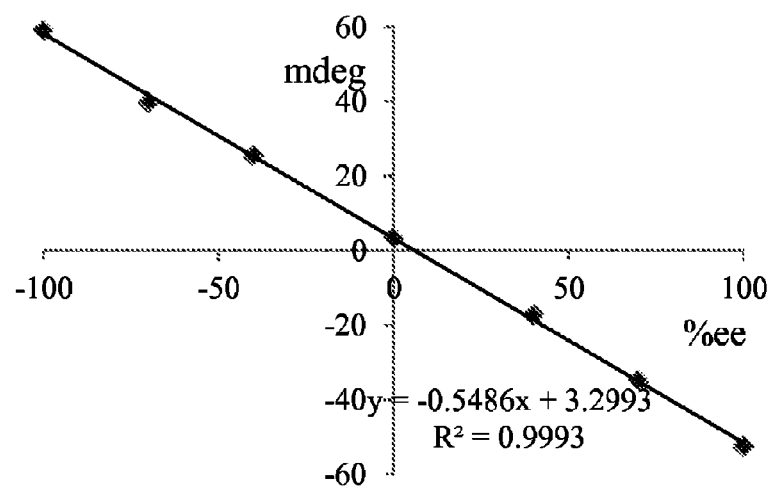
FIG. 46 is a plot of CD amplitude at 287.0 nm versus % ee of 6. All measurements were performed using 1 in acetonitrile (1.25 10⁻⁴ M) at room temperature.

The chiroptical response of 1 to the coordination of diamine 6 was investigated. Solutions containing equimolar amount of the sensor and the substrate with varying ee (100%, 70%, 40%, 0%, −40%, −70%, −100%) in ACN ($1.25 \times 10^{-4}$ M) were prepared (FIG. 45). The CD amplitude (mdeg) at 287.0 nm was plotted versus % ee (FIG. 46). The calibration curve showed a linear relationship ($mdeg = -0.5486 \times ee + 3.2993$, $R^2 = 0.9993$).

Four scalemic samples of diamine 6 with varying concentration and ee were prepared and treated with 1 as described above. Using the UV and CD calibration curves developed above, the concentration and ee of each sample were determined experimentally. This was achieved by fast UV and CD measurements using the same sample solution in ACN ($1.25 \times 10^{-4}$M). The measured UV response was first used to calculate the concentration of 6. Based on the observation that the CD response of the palladium complex increases linearly with relative concentration of the substrate at a given ee, the concentration value determined by UV analysis was then applied in the calculation of the sample ee. See Table 2.

TABLE 2

Actual vs. experimentally determined concentration and ee of 6.

| Actual conc. [$10^{-5}$ M] | Actual % ee | Calc. conc. [$10^{-5}$ M] | Calc. % ee |
|---|---|---|---|
| 11.25 | 80.0 | 11.38 | 85.9 |
| 8.75 | 60.0 | 7.88 | 67.7 |
| 6.25 | 50.0 | 6.13 | 49.6 |
| 6.25 | −60.0 | 6.63 | −66.7 |

Discussion of Examples 1-10

To investigate the possibility and practicality of (chir) optical detection of chiral diamines and amino alcohols, palladium complexes exhibiting either DPPF or 2,2'-bis (diphenylphosphino)diphenyl ether (BDPDE), which are readily available, chromophoric tropos ligands were prepared and tested. As demonstrated in Examples 1-10, stereodynamic metal complexes provide unique means for instantaneous determination of both the concentration and the ee of a variety of chiral samples based on two simple measurements (Scheme 4).

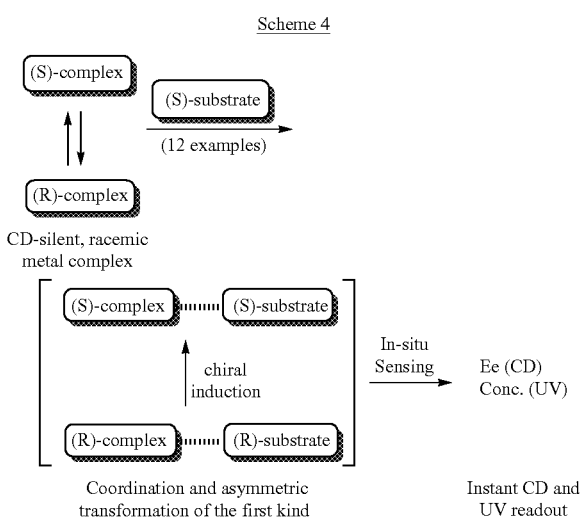

Scheme 4

[(BDPDE)(CH$_3$CN)$_2$Pd](SbF$_6$)$_2$ (complex 1) was prepared from PdCl$_2$(cod) and subsequent anion replacement in acetonitrile in high yields (Scheme 5). For comparison, [(DPPF)(CH₃CN)₂Pd](SbF₆)₂ (complex 2) (metal coordination of 1,1'-binaphthyl-2,2'-diamine and other diamines results in the formation of a single diastereomer within seconds; see Mikami & Aikawa, *Org. Lett.* 4:99-101 (2002), which is hereby incorporated by reference in its entirety) and palladium complexes 3 and 4 were also prepared (Scheme 5).

Scheme 5

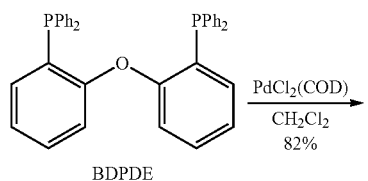

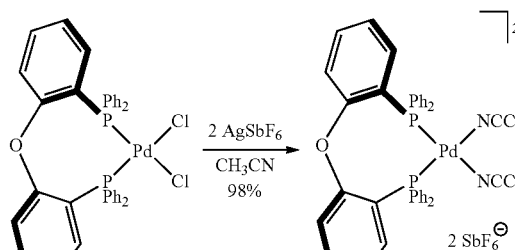

1

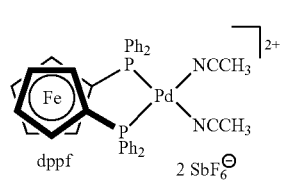

2

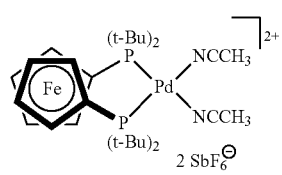

3

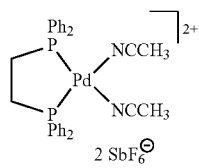

4

Based on the high degree of conformational flexibility of BDPDE, complex 1 exists as a mixture of rapidly interconverting enantiomers (Scheme 6).

Scheme 6

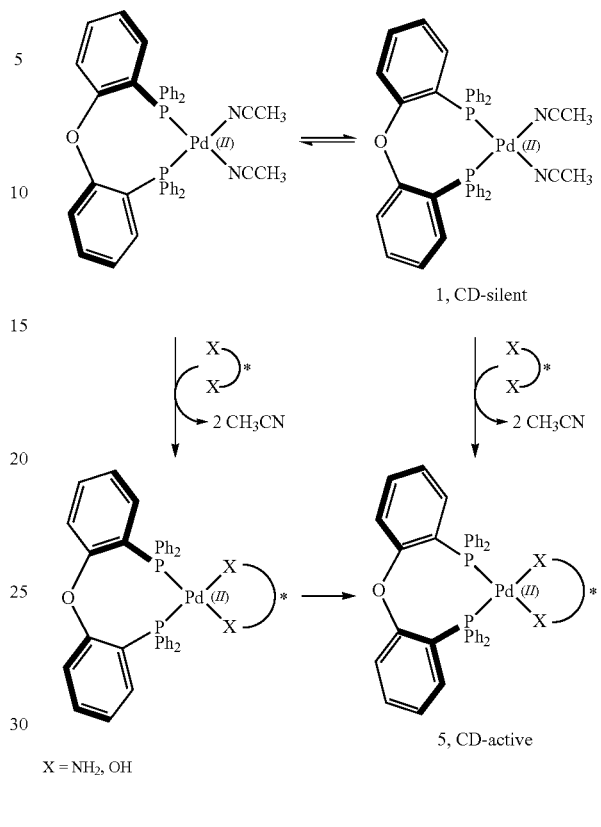

It was envisioned that fast ligand displacement of the two acetonitrile molecules with a chiral diamine or a 1,2-amino alcohol would generate 5, which should undergo instantaneous diastereomerization to the thermodynamically favored adduct. In the case of strong substrate-to-ligand asymmetric induction, the chiral information contained in the substrate will affect the stereochemical bias of the aromatic tropos ligand and favor population of a distinct, CD-active conformation. It was hypothesized that such a chiral amplification process has the potential to produce a strong induced circular dichroism output that can be measured and used for quantitative ee analysis.

Figure 37:
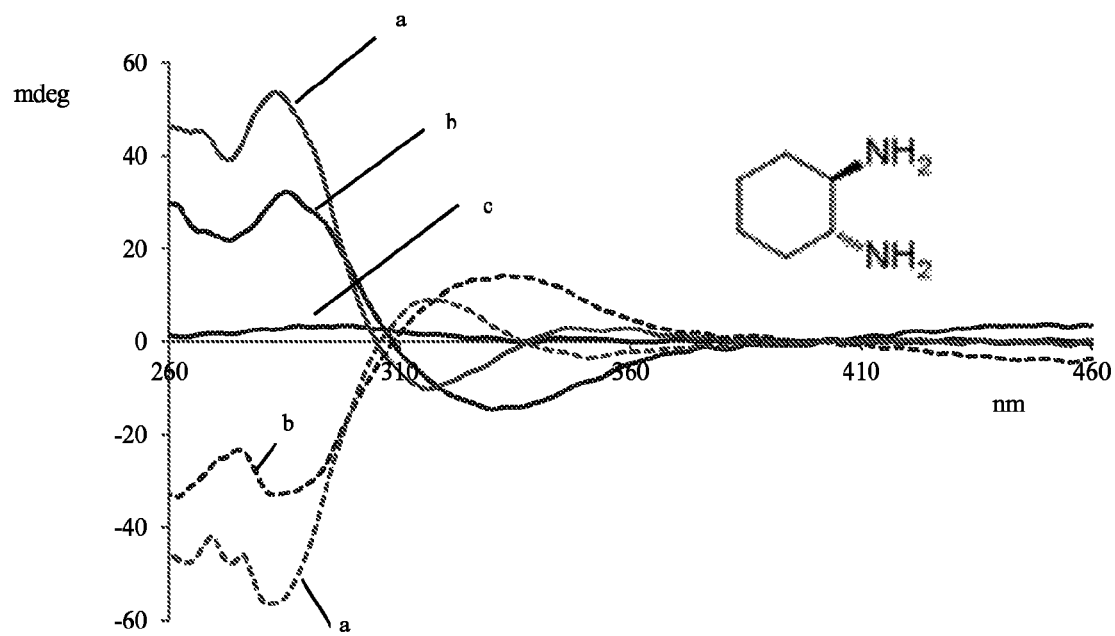
FIG. 37 is a comparison of the CD spectra obtained upon coordination of diamine (1R,2R)-6 (solid lines) and its enantiomer (dashed lines) to either 1 or 2 and to $Pd(SbF_6)_2$ in the absence of a tropos ligand in ACN (1.25×10⁻⁴ M). green (a): 6 and 1; red (b): 6 and 2; blue (c): 6 and $Pd(SbF_6)_2$ (1.0×10⁻⁴M).
Figure 38:
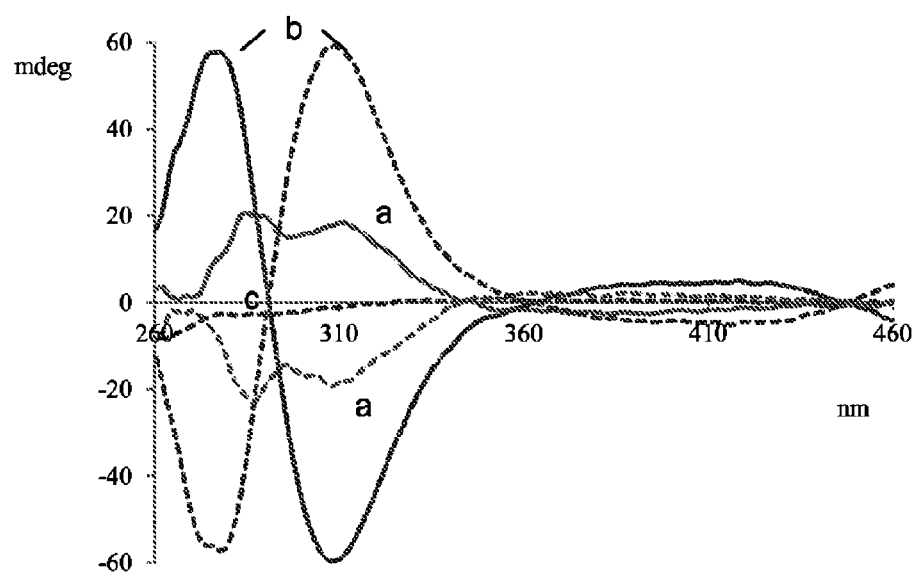
FIG. 38 is a comparison of the CD spectra obtained upon coordination of amino alcohol (1R,2S)-7 (solid lines) and its enantiomer (dashed lines) to either 1 or 2 and to $Pd(SbF_6)_2$ in the absence of a tropos ligand. green (a): 7 and 1; red (b): 7 and 2; blue (c): 7 and $Pd(SbF_6)_2$ (1.0×10⁻⁴M). All measurements were performed at 1.25 10⁻⁴ M in acetonitrile at 25° C.

The effect of (1R,2R)-diaminocyclohexane, 6, and (1S,2R)-2-amino-1-phenylpropan-1-ol, 7, on the chiroptical properties of the racemic palladium(II) complexes 1 and 2 were first tested. Both NMR spectroscopy and MS analysis showed instant coordination of the substrates to the metal center. Strong Cotton effects were obtained with these probes at submillimolar concentrations, indicating that a dramatic chiral induction process must have occurred (FIGS. 37-38). As expected, the opposite Cotton effects were observed when 1 and 2 were treated with (1S,2S)-6 and (1R,2S)-7. The racemic or achiral hosts 1-4 do not give a CD signal, and palladium complexes bearing any of the substrates tested but not a tropos ligand revealed very week Cotton effects that are not suitable for ee analysis. These results proved that inexpensive, readily available transition metal complexes bearing a UV active tropos ligand can be used for sensitive detection of chiral compounds. The CD measurements can be performed without any delay after mixing the palladium probe with the chiral analyte, and sensing experiments conducted with the enantiomers of 8-17 under the same conditions also gave strong CD effects. This is important because it underscores the general usefulness and the possibility of time-efficient CD analysis with tropos ligand-derived metal complexes. The exchange of the chloride anions in the precursor of 1 with acetonitrile is crucial, and no CD induction was observed upon addition of the substrates to (BDPDE)PdCl$_2$ under identical conditions.

A closer look at the CD spectra reveals that the sensors do not only differentiate between enantiomers, but also provide a substrate-specific response (see FIGS. 12-38 and Example 7, supra). For example, the CD spectra obtained with purely aliphatic compounds differ from those produced with compounds containing aromatic groups, which may be attributed to ECCD effects. A comparison of the CD effects obtained with the enantiomers of 1,2-diphenylethane-1,2-diamine, 8, and palladium complexes 1-4 reveals that the CD effects do not solely originate from a chiral induction process at the tropos ligand backbone, but also involve propeller-like geometries at the phosphine hubs (for chirality CD sensing with trityl propellers, see Sciebura et al., *Angew. Chem. Int. Ed.* 48:7069-72 (2009); Sciebura & Gawronski, *Chem. Eur. J.* 17:13138-41 (2011), which are hereby incorporated by reference in their entirety). Although 4 showed a remarkable chiroptical output, 1 and 2 give rise to stronger CD signals at higher wavelengths and were therefore selected as the more promising probes for actual ee measurements.

The practicality of chiral sensing with tropos ligands was examined by using the DPPF derived palladium(II) complex 2 for quantitative analysis of the enantiomeric composition of amino alcohol 7. It was found that the CD response increases linearly with the ee of the samples tested (FIGS. 39-40). Five scalemic samples of 7 covering a wide ee range were prepared and treated with 2. The ee's could be calculated directly from the measured CD amplitudes at 278 and 310 nm (see Example 8, supra). As shown in Table 1 above (see Example 8, supra), the averaged experimentally obtained results were within 3% of the actual values, which is sufficient for high-throughput screening (HTS) applications. Essentially the same linear relationship between the CD response and sample ee using palladium complex 1 and diamine 8 was observed (FIGS. 41-42; see Example 9, supra). It is apparent that chirality sensing with a metal complex bearing a tropos ligand is a generally applicable concept that provides a practical means for fast and accurate ee analysis at approximately 10 times lower concentrations than typically used in HPLC.

It was suspected that the introduction of tropos ligands to chiral sensing bears an excellent opportunity to develop an assay that can achieve fast quantification of the total amount (concentration) and the ee by two simple measurements using a single sample of a chiral substrate. An important observation in this regard was that the displacement of the two acetonitrile molecules coordinated to palladium complex 1 by a substrate results in a characteristic UV absorption change. For example, the UV band at 370 nm steadily decreased upon addition of one equivalent of 6 to 1, while no further change occurred with excess of the diamine (FIGS. 43-44; see Example 10, supra).

Together with the distinct induced CD spectra that originate from the coordination of diamine 6 to this palladium complex and the linear relationship between the CD amplitude measured and the ee (FIGS. 45-46), one can in fact determine both the concentration of samples of 6 by a UV measurement and the enantiomeric composition by CD analysis of the same solution (at a given sample ee, the CD amplitude also changes linearly with the substrate concentration). Regression analysis of the CD and UV readouts enabled the calculation of these two essential parameters at once with very good accuracy (see supra Example 10, Table 2).

Examples 1-10 show that readily available palladium complexes carrying tropos ligands DPPF or BDPDE provide a distinct UV change and CD signal upon coordination of amino alcohols or diamines. This allows instantaneous in situ determination of the concentration and the ee of a wide range of chiral diamines and amino alcohols based on simple UV and CD measurements with a single sample. The quantitative sensing approach described in Examples 1-10 has several advantages: it is fast and adaptable to automated HTS protocols, it relies on dynamic metal coordination and rapid equilibration between fluxional diastereomers, which eliminates laborious derivatization and purification steps, and it requires very small sample amounts. This reduces the amount of solvents needed and effectively limits waste production.

Example 11—General Information

Biphenol 1, all reagents, and solvents were commercially available and used without further purification. Reactions were carried out under inert and anhydrous conditions. Flash chromatography was performed on silica gel, particle size 40-63 µm. NMR spectra were obtained at 400 MHz ($^1$H-NMR) and 100 MHz ($^{13}$C-NMR) using CDCl$_3$ as solvent and TMS as reference unless otherwise noted.

The compound numbers used in Examples 11-25 refer to the following compounds (where applicable, only one enantiomer is shown). Some of these compounds may be numbered differently in Examples 1-10 and/or Examples 26-32.

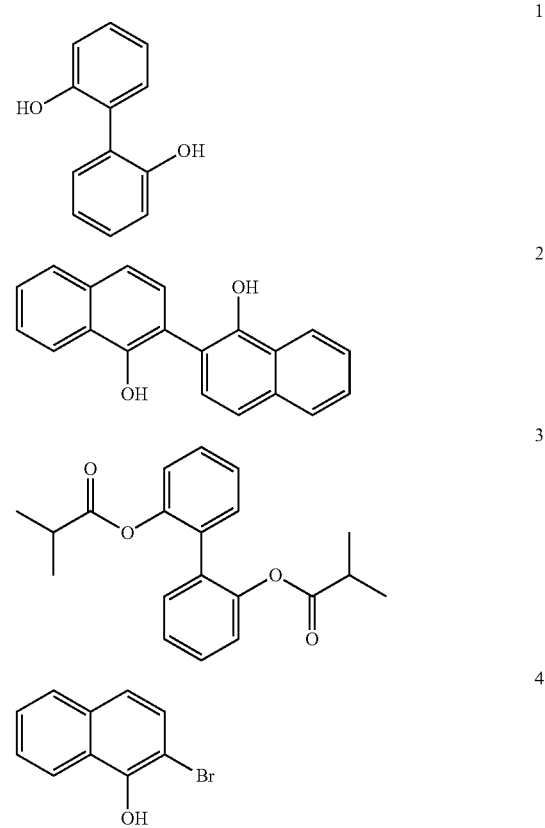

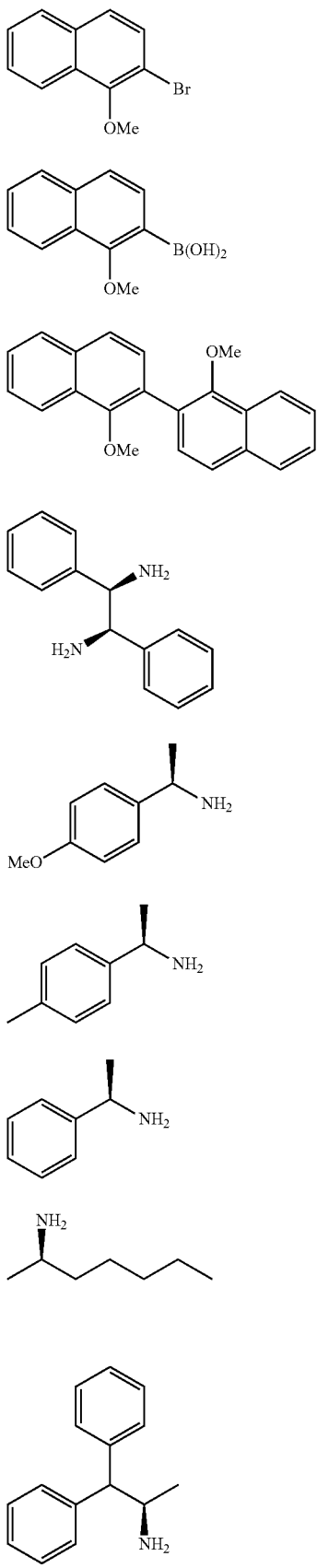
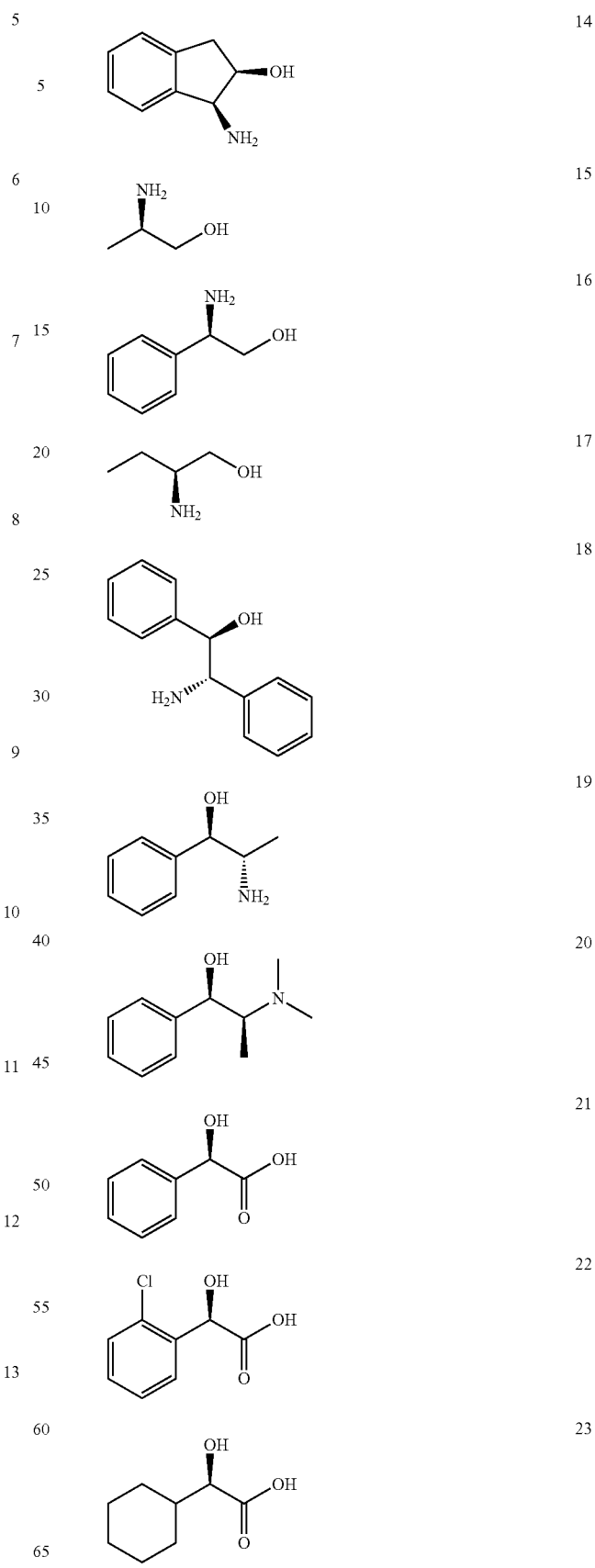

-continued
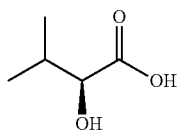
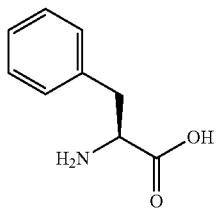
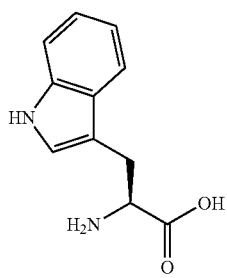
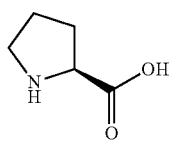
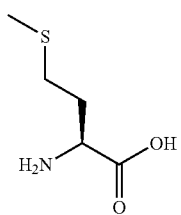
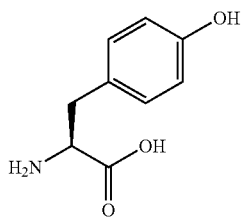
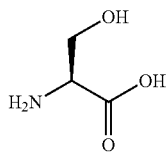
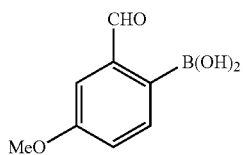
-continued
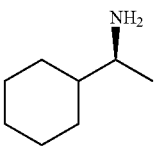
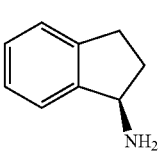
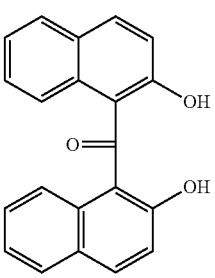
Example 12—Synthesis of Ligand 2 and Product Characterization
Ligand 2 was prepared as shown in Scheme 7.
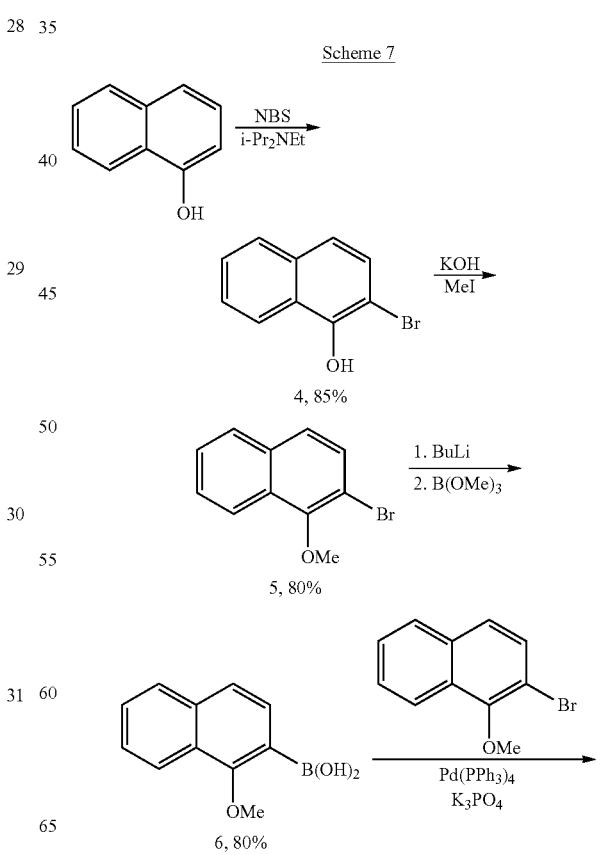

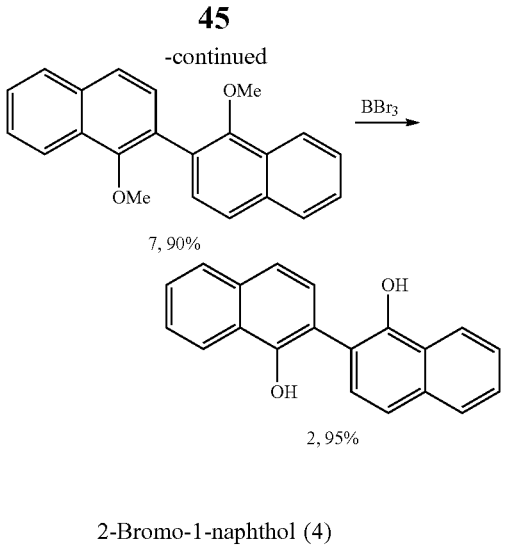

7, 90%

2, 95%

2-Bromo-1-naphthol (4)

Figure 47A:
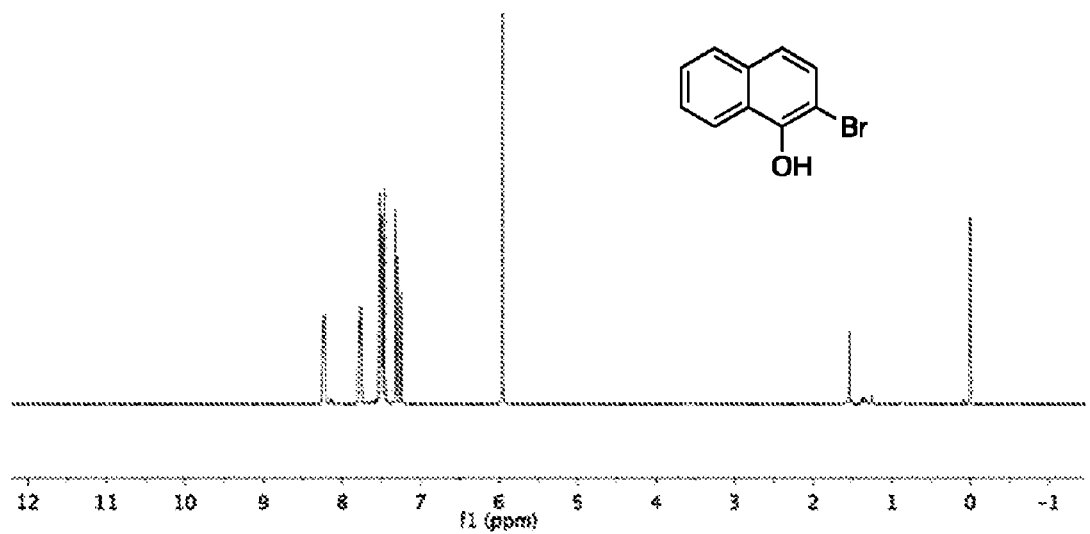
FIGS. 47A-B are the ¹H NMR (FIG. 47A) and ¹³C NMR (FIG. 47B) spectra of 4 in $CDCl_3$.
Figure 47B:
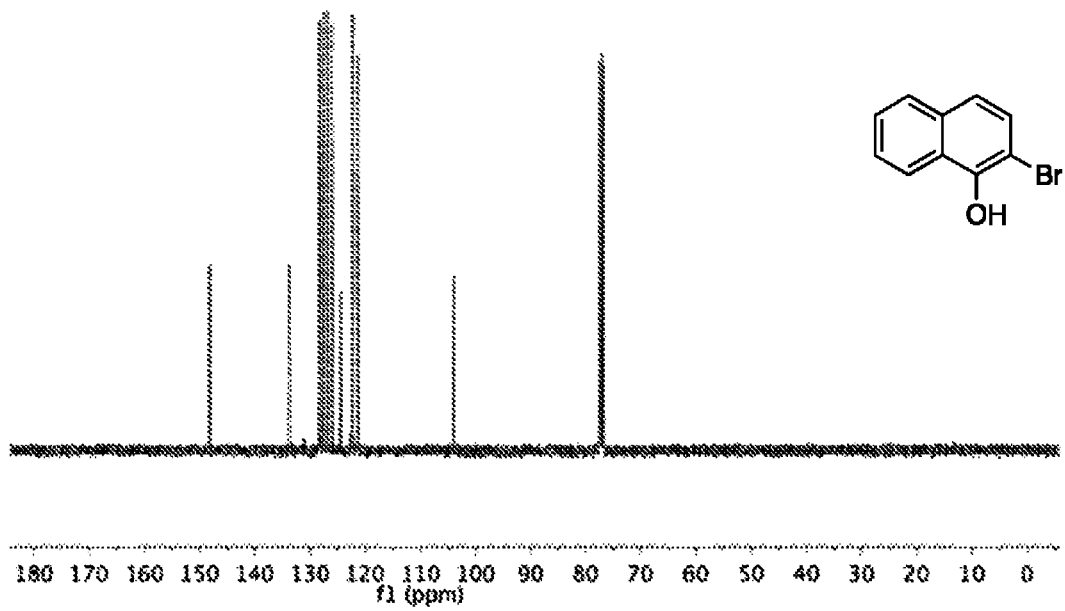

1-Naphthol (500 mg, 3.5 mmol) and diisopropylamine (49 μl, 0.35 mmol) were dissolved in 10 mL of dichloromethane. N-Bromosuccinimide (679.0 mg, 3.8 mmol) was carefully added and the reaction mixture was stirred at 40° C. for 8 hours. The resulting mixture was allowed to cool to room temperature, quenched with 2N $H_2SO_4$, and extracted with dichloromethane. The combined organic layers were dried over $MgSO_4$ and concentrated in vacuo. Purification by flash chromatography on silica gel ($CH_2Cl_2$:hexanes 2:1) afforded 650 mg (2.9 mmol, 85% yield) of 2-bromo-1-naphthol (4) (Velder et al., *Adv. Synth. Catal.* 350:1309-15 (2008), which is which is hereby incorporated by reference in its entirety) as a white solid. $^1$H NMR (FIG. 47A): δ=5.96 (s, 1H), 7.30 (d, J=8.8 Hz, 1H), 7.46 (d, J=8.8 Hz, 1H), 7.49-7.52 (m, 2H), 7.77 (m, 1H), 8.23 (m, 1H). $^{13}$C NMR (FIG. 47B): δ=104.0, 121.3, 122.3, 124.4, 126.1, 126.8, 127.6, 128.3, 133.7, 148.2.

2-Bromo-1-methoxynaphthalene (5)

Figure 48A:
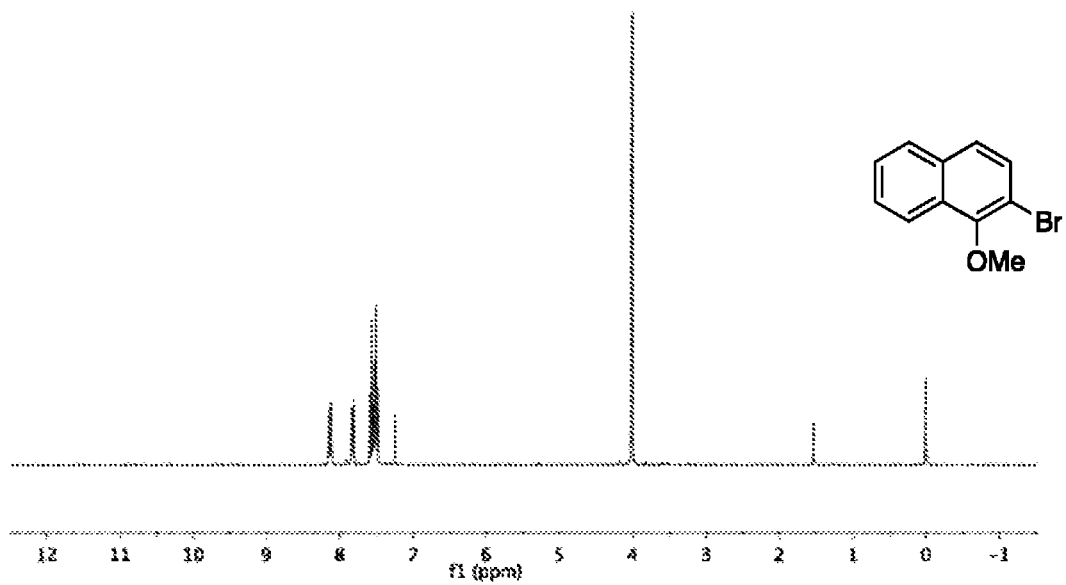
FIGS. 48A-B are the ¹H NMR (FIG. 48A) and ¹³C NMR (FIG. 48B) spectra of 5 in $CDCl_3$.
Figure 48B:
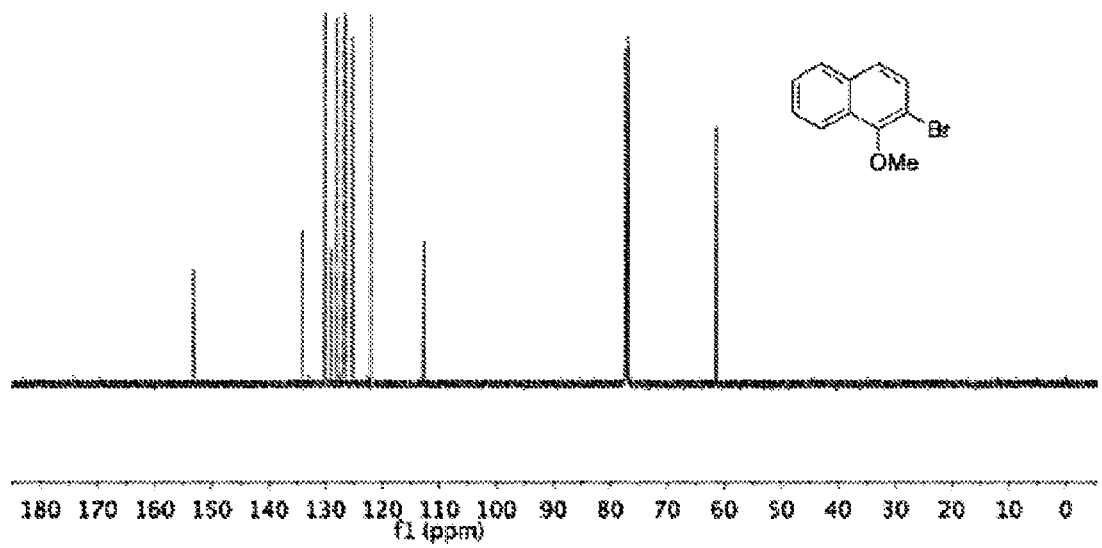

A solution of 4 (650 mg, 2.9 mmol), KOH (325 mg, 5.8 mmol), and MeI (1.08 g, 17.4 mmol) in 10 mL of ACN was stirred at room temperature for 12 hours. The mixture was washed with water, extracted with dichloromethane, dried over $MgSO_4$ and concentrated in vacuo. Purification by flash chromatography on silica gel ($CH_2Cl_2$:hexanes 1:5) afforded 550 mg (2.3 mmol, 80%) of 2-bromo-1-methoxynaphthalene (5) (Zupancic et al., *Adv. Synth. Catal.* 350:2024-32 (2008), which is hereby incorporated by reference in its entirety) as a white solid. $^1$H NMR (FIG. 48A): δ=4.01 (s, 3H), 7.48-7.58 (m, 4H), 7.81 (d, J=7.5 Hz, 1H), 8.12 (d, J=8.3 Hz, 1H). $^{13}$C NMR (FIG. 48B): δ=61.4, 112.6, 122.1, 125.2, 126.5, 126.8, 128.0, 129.0, 130.1, 134.0, 153.1.

1-Methoxy-2-naphthylboronic acid (6)

Figure 49A:
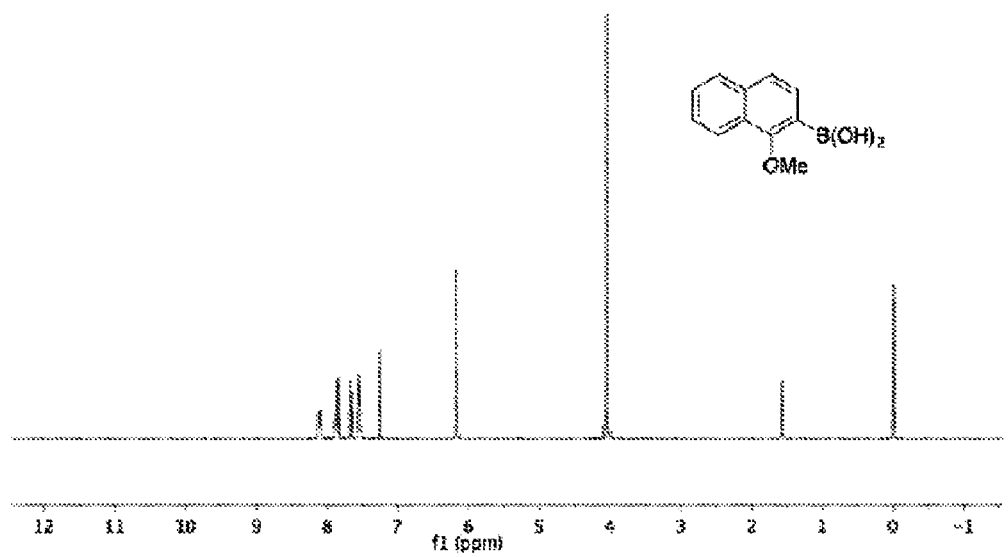
FIGS. 49A-B are the ¹H NMR (FIG. 49A) and ¹³C NMR (FIG. 49B) spectra of 6 in $CDCl_3$.
Figure 49B:
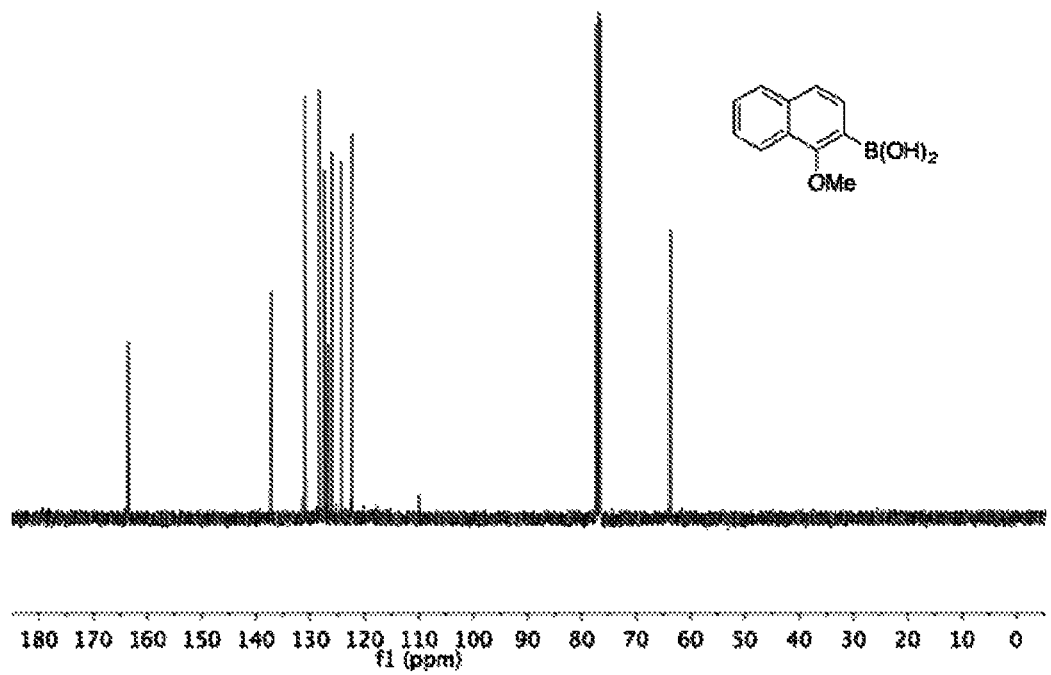

A solution of 5 (550 mg, 2.3 mmol) in 10 mL of diethyl ether was cooled to −78° C. n-BuLi (1.6 M in hexanes, 2.2 mL, 3.5 mmol) was added dropwise and the mixture was stirred at −78° C. for 30 minutes. Trimethoxyborate (0.5 mL, 4.6 mmol) was added in one portion and the mixture was allowed to come to room temperature. After 12 hours, 10 mL of 1M HCl was added. The mixture was stirred vigorously for 30 minutes and extracted with dichloromethane. The combined organic layers were extracted with 2M NaOH and the combined aqueous layers were washed with dichloromethane. The aqueous layer was acidified to pH<3 with 1M HCl and extracted with dichloromethane. The combined organic layers were dried over $MgSO_4$ and concentrated in vacuo to give 370 mg (1.8 mmol, 80%) of 1-methoxy-2-naphthylboronic acid (6) (Holmberg et al., *Bioorg. Med. Chem. Lett.* 15:747-50 (2005), which is hereby incorporated by reference in its entirety which is hereby incorporated by reference in its entirety) as a yellow solid. $^1$H NMR (FIG. 49A): δ=4.05 (s, 3H), 6.18 (s, 2H), 7.53-7.56 (m, 2H), 7.65 (d, J=8.3 Hz, 1H), 7.84 (d, J=8.4 Hz, 1H), 7.88 (m, 1H), 8.11 (m, 1H). $^{13}$C NMR (FIG. 49B): δ=63.7, 110.0, 122.3, 124.3, 126.1, 126.8, 127.4, 128.3, 131.0, 137.2, 163.5.

1,1'-Dimethoxy-2-2'-binaphthalene (7)

Figure 50A:
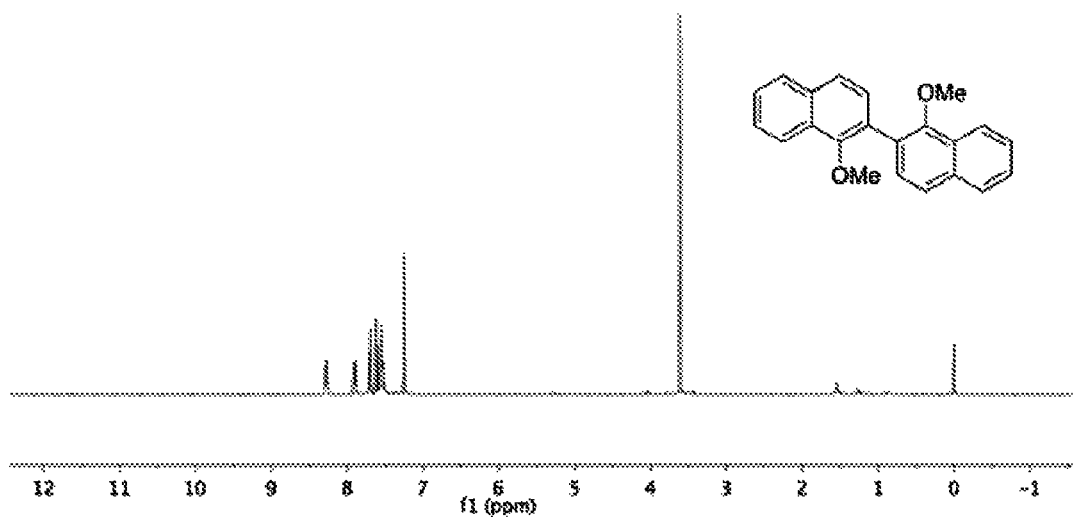
FIGS. 50A-B are the ¹H NMR (FIG. 50A) and ¹³C NMR (FIG. 50B) spectra of 7 in $CDCl_3$.
Figure 50B:
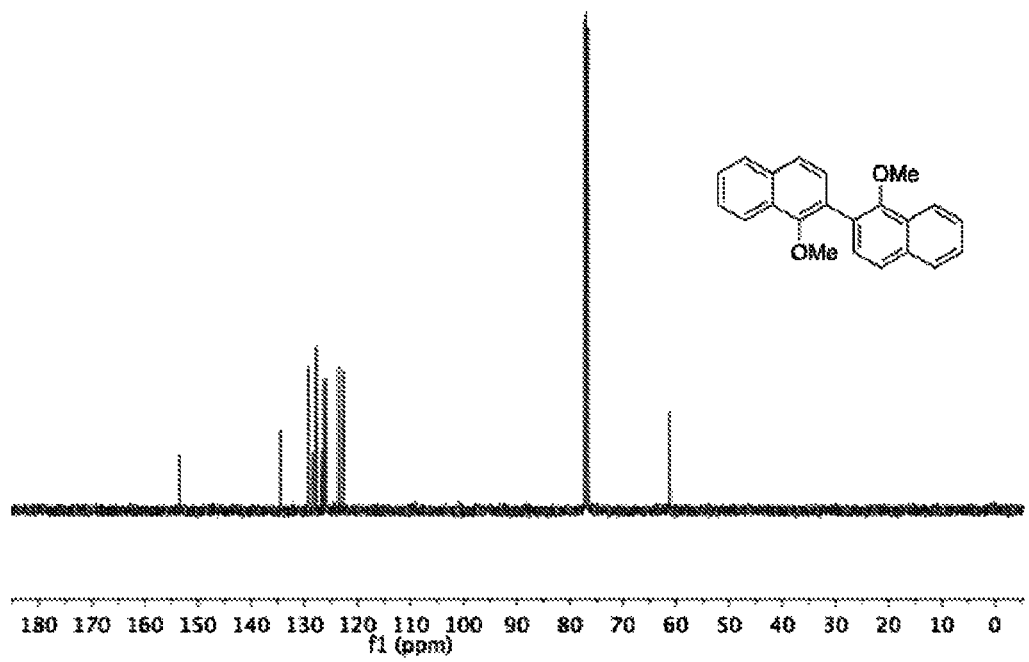

A solution of 5 (300 mg, 1.3 mmol), 6 (385 mg, 1.9 mmol), Pd(PPh$_3$)$_4$ (113 mg, 0.09 mmol), and K$_3$PO$_4$ (690 mg. 3.3 mmol) in 12 mL of toluene:EtOH:water (3:2:1 v/v) was stirred at 100° C. for 12 hours. The reaction mixture was allowed to cool to room temperature, quenched with water, and extracted with dichloromethane. The combined organic layers were dried over $MgSO_4$ and concentrated in vacuo. Purification by flash chromatography on silica gel ($CH_2Cl_2$: hexanes 1:1) afforded 370 mg (1.2 mmol, 90%) of 1,1'-dimethoxy-2-2'-binaphthalene (7) (Kashiwagi et al., *Chem. Lett.* 22:81-94 (1993), which is hereby incorporated by reference in its entirety) as a white solid. $^1$H NMR (FIG. 50A): δ=3.61 (s, 6H), 7.52-7.58 (m, 4H), 7.60 (d, J=8.5 Hz, 2H), 7.69 (d, J=8.5 Hz, 2H), 7.89 (dd, J=6.2 Hz, 2.1 Hz, 2H), 8.26 (dd, J=7.1 Hz, 1.9 Hz, 2H). $^{13}$C NMR (FIG. 50B): δ=61.2, 122.6, 123.4, 126.0, 126.3, 126.8, 127.8, 128.4, 129.3, 134.5, 153.5.

1,1'-Dihydroxy-2,2'-binaphthalene (2)

Figure 51A:
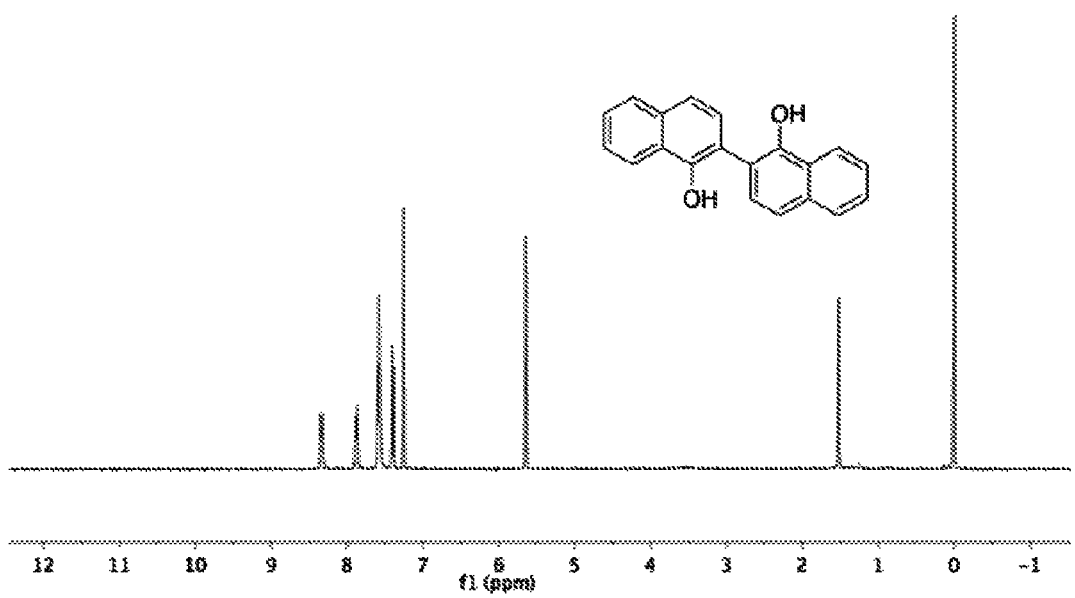
FIGS. 51A-B are the ¹H NMR (FIG. 51A) and ¹³C NMR (FIG. 51B) spectra of 2 in $CDCl_3$.
Figure 51B:
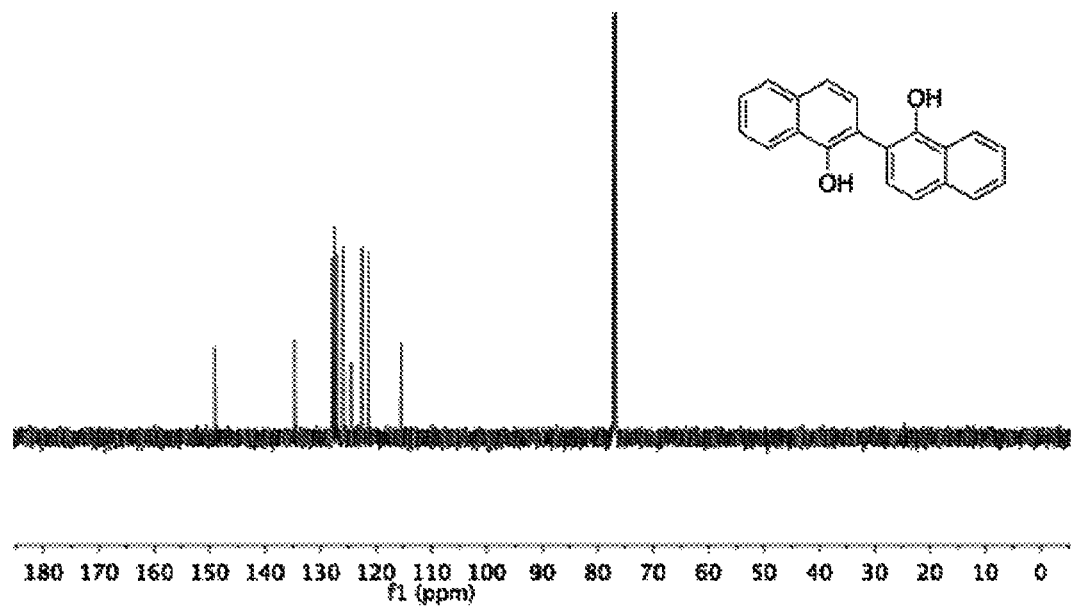

To a solution of 7 (350 mg, 1.1 mmol) in 10 mL dichloromethane was slowly added BBr$_3$ (1M in CH$_2$Cl$_2$, 6.60 mL, 6.60 mmol), and stirring was continued at room temperature for 2 hours. The mixture was cooled to 0° C., quenched with isopropyl alcohol, washed with water, and extracted with dichloromethane. The combined organic layers were dried over $MgSO_4$ and concentrated in vacuo. Purification by flash chromatography on silica gel ($CH_2Cl_2$) afforded 302 mg (1.06 mmol, 95%) of 1,1'-dihydroxy-2,2'-binaphthalene (2) (Takeya et al., *Tetrahedron* 60:6295-310 (2004), which is hereby incorporated by reference in its entirety) as a white solid. $^1$H NMR (FIG. 51A): δ=5.65 (s, 2H), 7.39 (d, J=8.4 Hz, 2H), 7.56-7.60 (m, 6H), 7.88 (m, 2H), 8.37 (m, 2H). $^{13}$C NMR (FIG. 51B): δ=115.5, 121.3, 122.5, 124.5, 126.0, 127.1, 127.6, 127.9, 134.7, 149.0.

Example 13—Sensing Experiments Generally 1,1'-Dihydroxy-2,2'-binaphthalene (2) was first treated with Et$_2$Zn or B(OMe)$_3$ using THF or CHCl$_3$ as solvent. To the corresponding zinc and boron complexes were added substrates 8-20 and 21-30, respectively, and the chiroptical properties of the resulting adducts were analyzed by CD spectroscopy as described below. None of the analytes tested was CD active under the specified conditions in the absence of 2.

Example 14—MS Analysis of the Zinc and Boron Complexes

Figure 52:
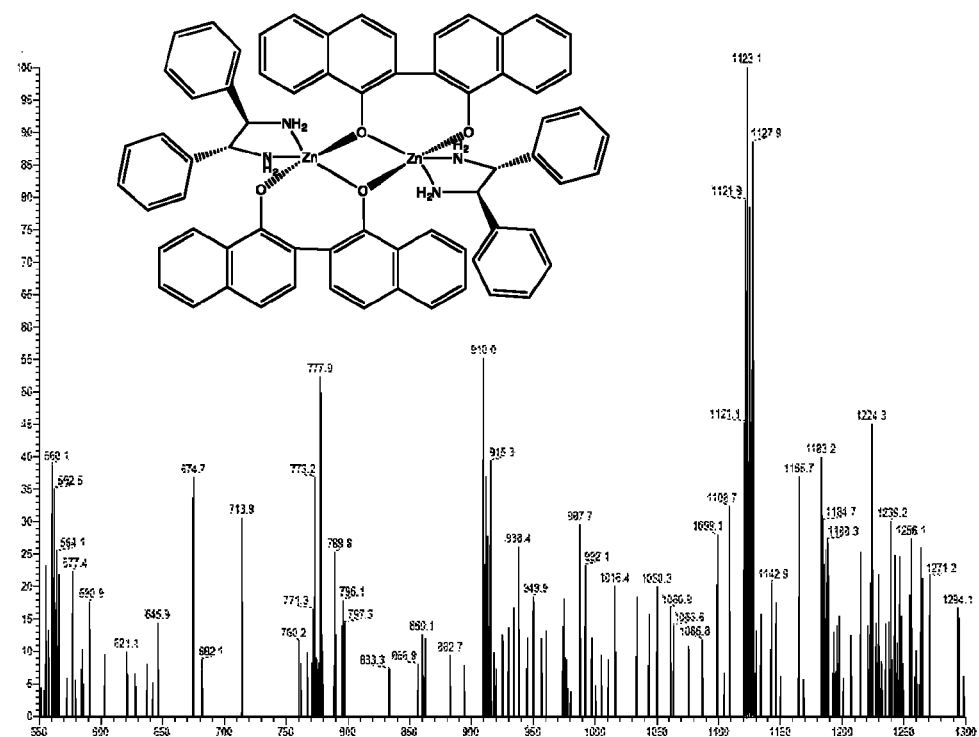
FIG. 52 is the MS spectrum of the complex obtained from 2, $ZnEt_2$, and (1R,2R)-8. ESI-MS: m/z=1123.1 (M⁺¹).

A solution of 2 (2.86 mg, 0.01 mmol) and 8 (2.12 mg, 0.01 mmol) in 1 mL of a dry THF:EtOH mixture (1:1 v/v) was prepared. Then, Et$_2$Zn (10 μl, 0.01 mmol, 1M in hexanes)

was added and the mixture was stirred for 20 minutes. Electrospray mass spectrometry (positive ion mode) showed the presence of a bimetallic complex containing two equivalents of 2, 8, Zn, and ethanol (FIG. 52). This result is in very good agreement with the crystallographic analysis of a complex prepared from a diethyl ether/chloroform solution (see Example 24, infra).

Figure 53:
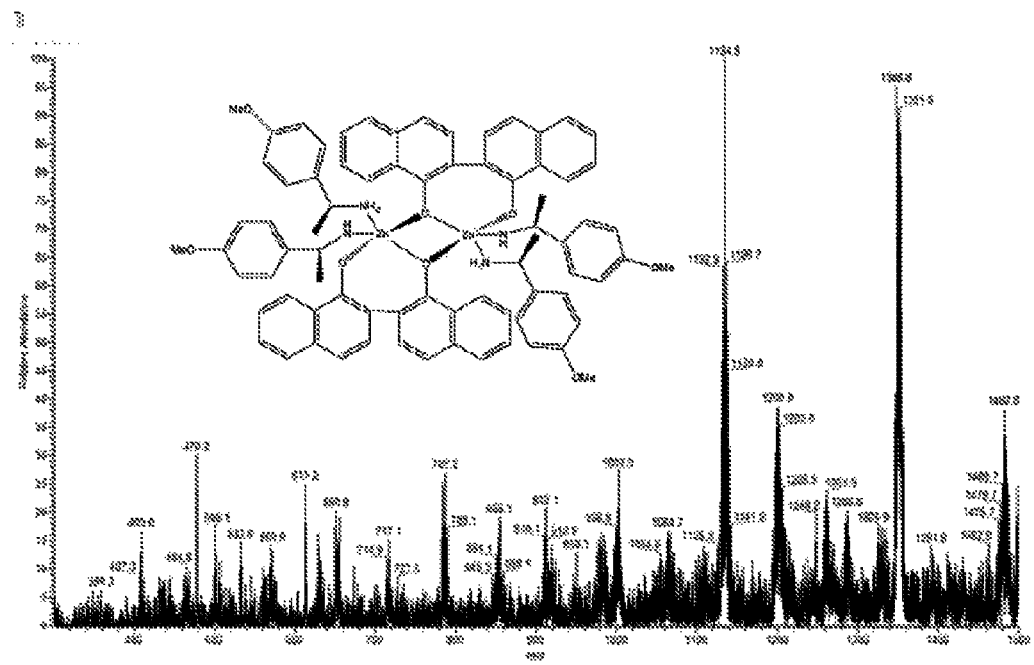
FIG. 53 is the MS spectrum of the complex obtained from 2, $ZnEt_2$, and (S)-9. ESI-MS: m/z=1348.8 (M⁺¹).
Figure 54:
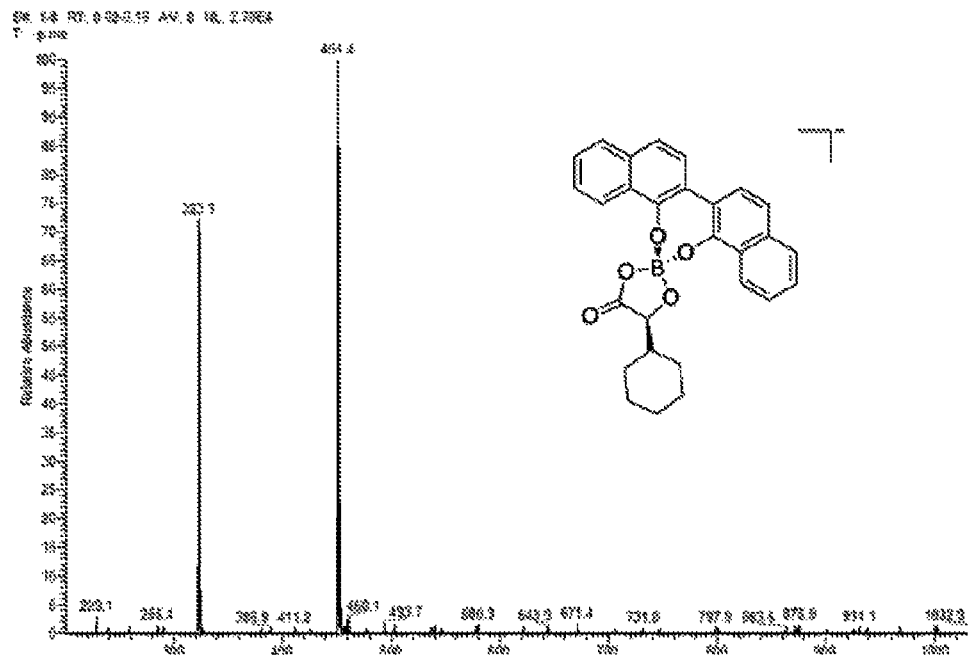
FIG. 54 is the MS spectrum of the complex formed from 2, B(OMe)₃, and (R)-23. ESI-MS: m/z=451 (M⁻).
Figure 55:
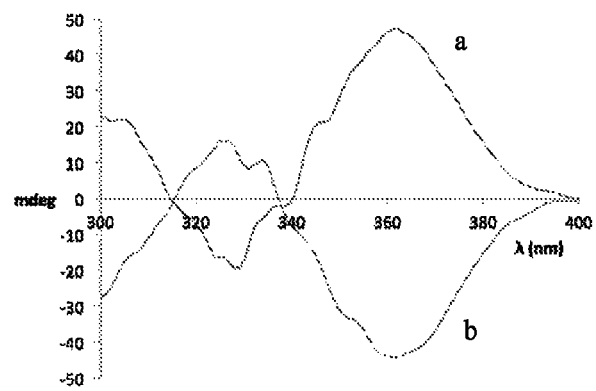
FIG. 55 is the CD spectra obtained using 2 and (1R,2R)-8 (blue (a)) and (1S,2S)-8 (red (b)).
Figure 56:
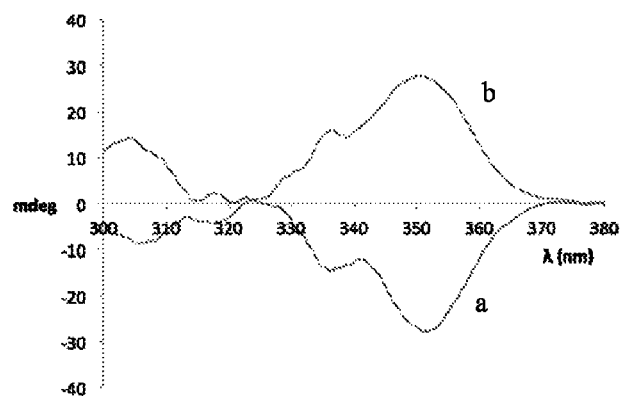
FIG. 56 is the CD spectra obtained using 2 and (R)-9 (blue (a)) and (S)-9 (red (b)).
Figure 57:
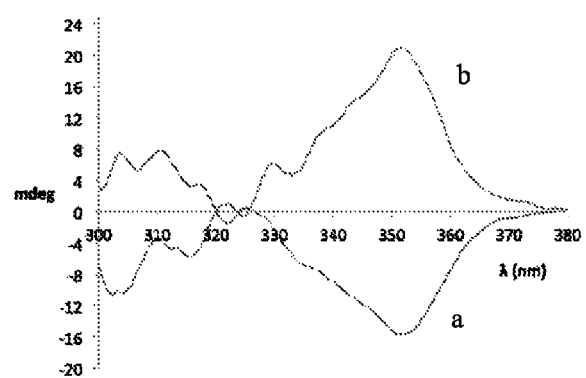
FIG. 57 is the CD spectra obtained using 2 and (R)-10 (blue (a)) and (S)-10 (red (b)).
Figure 58:
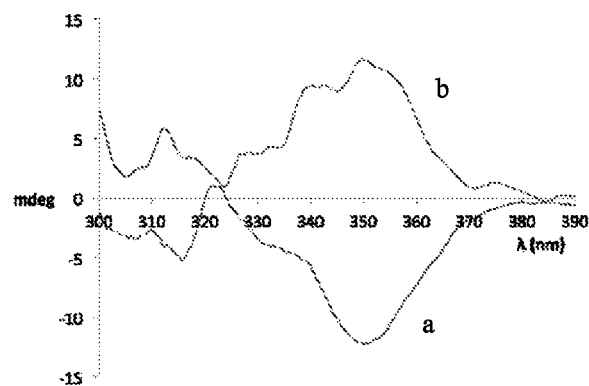
FIG. 58 is the CD spectra obtained using 2 and (R)-11 (blue (a)) and (S)-11 (red (b)).
Figure 59:
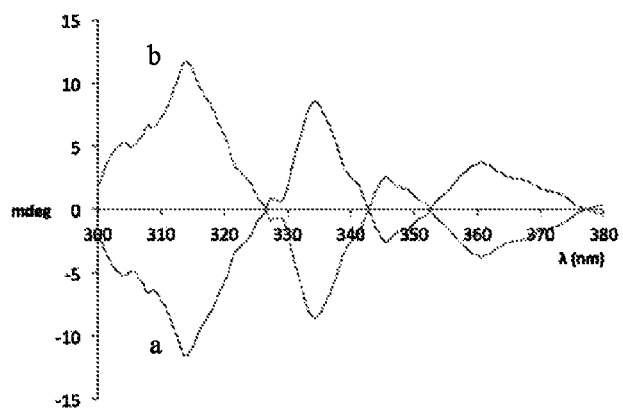
FIG. 59 is the CD spectra obtained using 2 and (R)-12 (blue (a)) and (S)-12 (red (b)).
Figure 60:
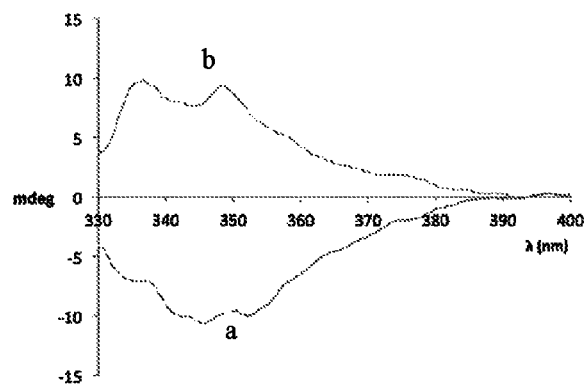
FIG. 60 is the CD spectra obtained using 2 and (R)-13 (blue (a)) and (S)-13 (red (b)).
Figure 61:
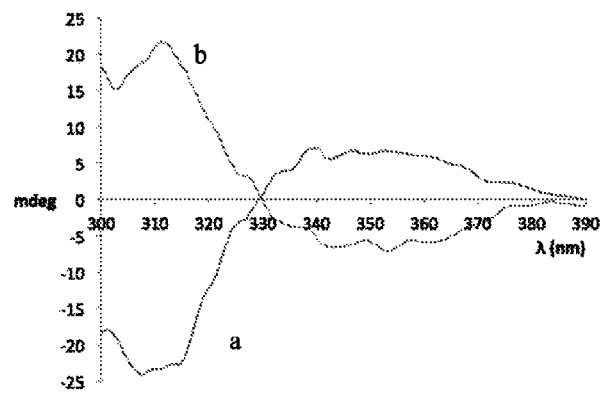
FIG. 61 is the CD spectra obtained using 2 and (1R,2S)-14 (blue (a)) and (1S,2R)-14 (red (b)).
Figure 62:
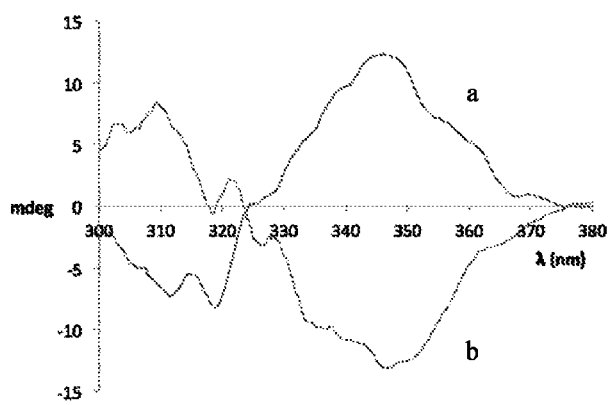
FIG. 62 is the CD spectra obtained using 2 and (R)-15 (blue (a)) and (S)-15 (red (b)).
Figure 63:
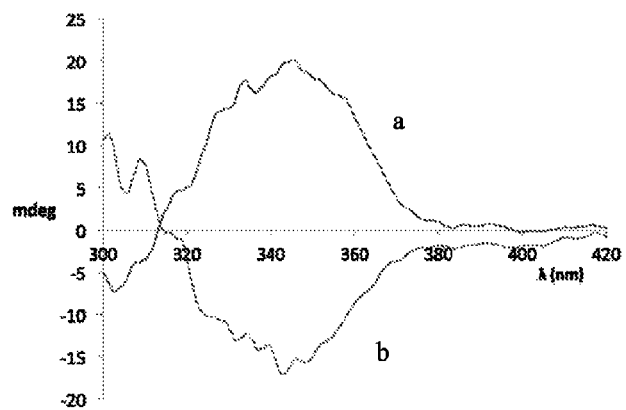
FIG. 63 is the CD spectra obtained using 2 and (R)-16 (blue (a)) and (S)-16 (red (b)).
Figure 64:
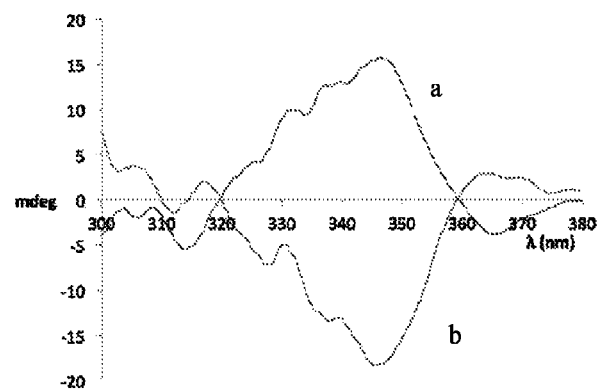
FIG. 64 is the CD spectra obtained using 2 and (R)-17 (blue (a)) and (S)-17 (red (b)).
Figure 65:
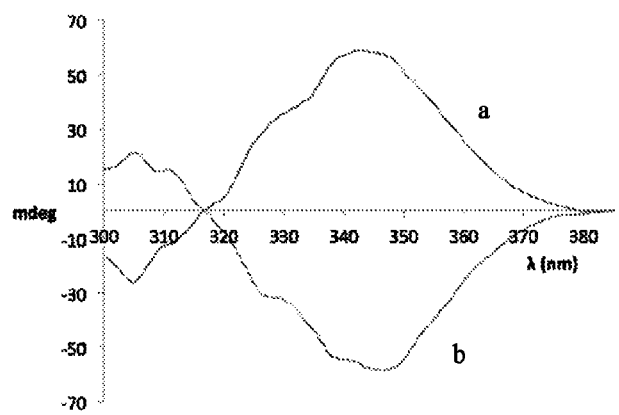
FIG. 65 is the CD spectra obtained using 2 and (1R,2S)-18 (blue (a)) and (1S,2R)-18 (red (b)).
Figure 66:
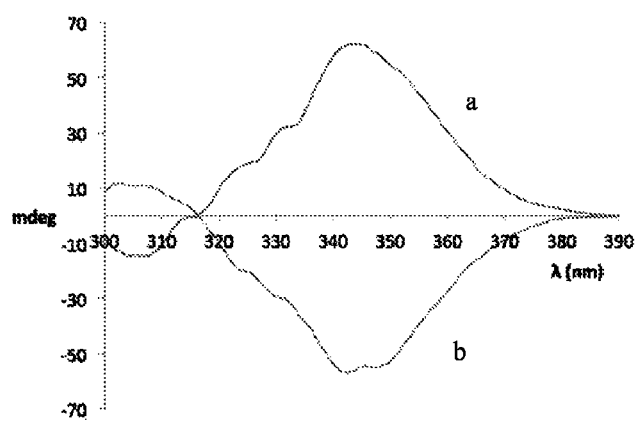
FIG. 66 is the CD spectra obtained using 2 and (1R,2S)-19 (blue (a)) and (1S,2R)-19 (red (b)).
Figure 67:
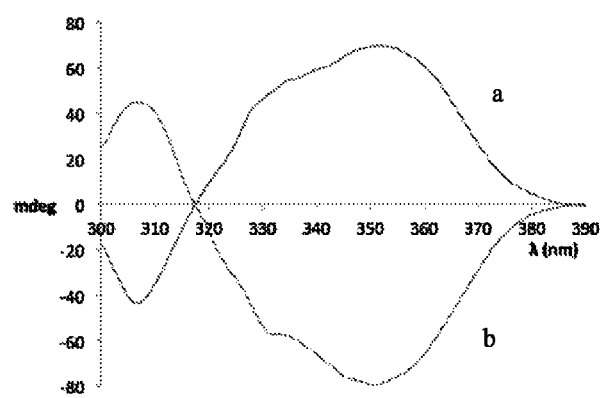
FIG. 67 is the CD spectra obtained using 2 and (1R,2S)-20 (blue (a)) and (1S,2R)-20 (red (b)).
Figure 68:
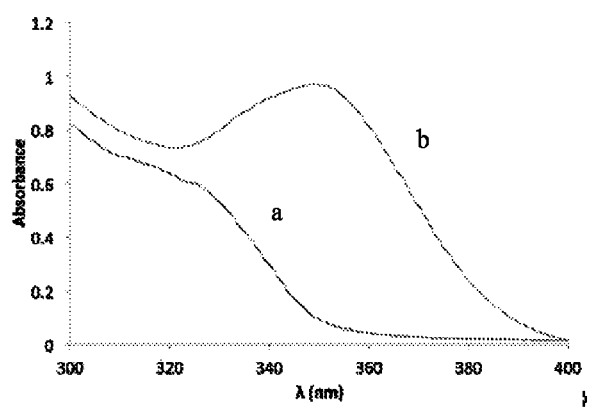
FIG. 68 is the UV spectra of the complex formed from $Et_2Zn$ and 2 (blue (a)) and upon addition of one equivalent of 8 (red (b)) in anhydrous diethyl ether (1.0×10⁻⁴ M).
Figure 69:
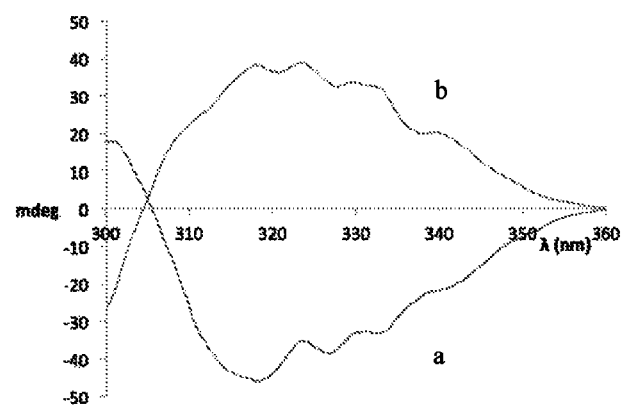
FIG. 69 is the CD spectra obtained using 2 and (R)-21 (blue (a)) and (S)-21 (red (b)).
Figure 70:
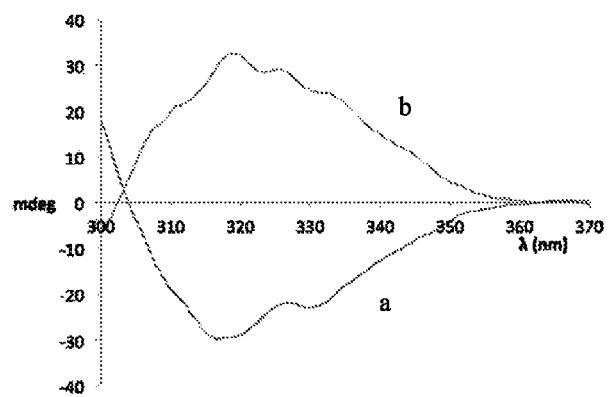
FIG. 70 is the CD spectra obtained using 2 and (R)-22 (blue (a)) and (S)-22 (red (b)).
Figure 71:
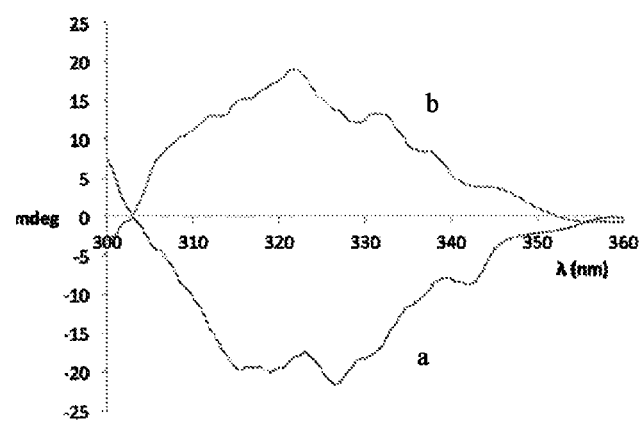
FIG. 71 is the CD spectra obtained using 2 and (R)-23 (blue (a)) and (S)-23 (red (b)).
Figure 72:
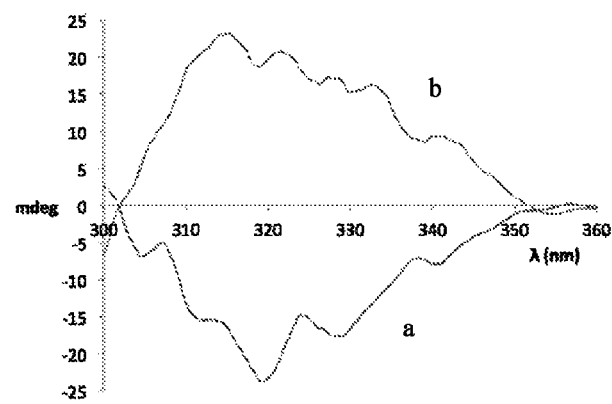
FIG. 72 is the CD spectra obtained using 2 and (R)-24 (blue (a)) and (S)-24 (red (b)).
Figure 73:
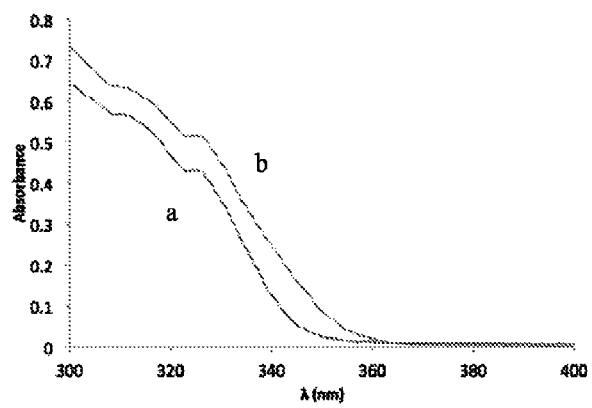
FIG. 73 is the UV spectra of the complex formed from B(OMe)₃ and 2 (blue (a)) and upon addition of one equivalent of 21 (red (b)) in anhydrous $CHCl_3$ (1.0×10⁻⁴ M).
Figure 74:
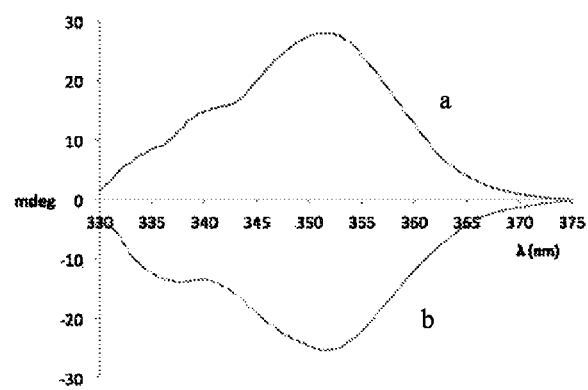
FIG. 74 is the CD spectra obtained using 2 and (R)-25 (blue (a)) and (S)-25 (red (b)).
Figure 75:
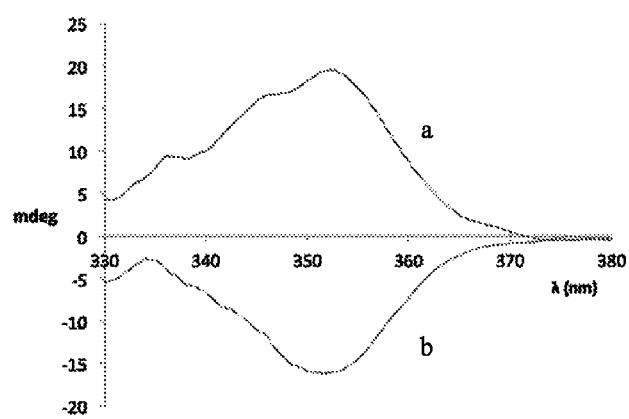
FIG. 75 is the CD spectra obtained using 2 and (R)-26 (blue (a)) and (S)-26 (red (b)).
Figure 76:
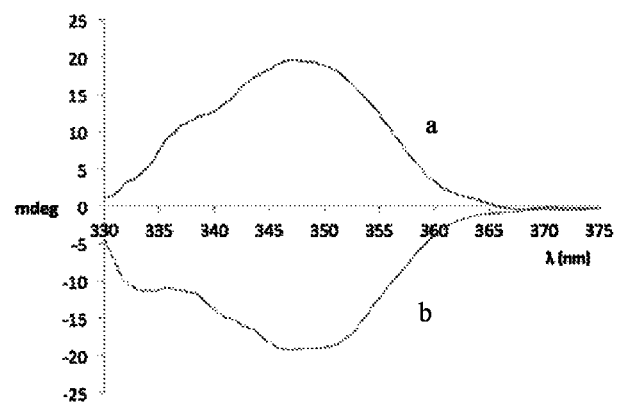
FIG. 76 is the CD spectra obtained using 2 and (R)-27 (blue (a)) and (S)-27 (red (b)).
Figure 77:
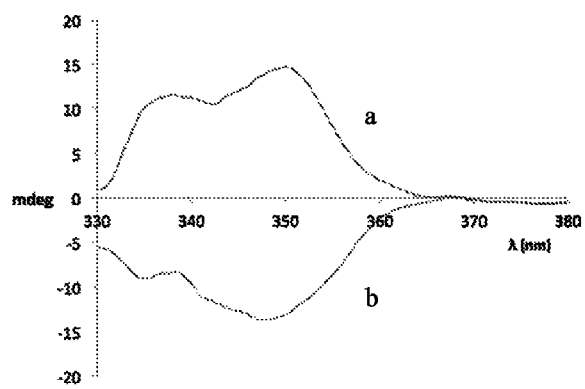
FIG. 77 is the CD spectra obtained using 2 and (R)-28 (blue (a)) and (S)-28 (red (b)).
Figure 78:
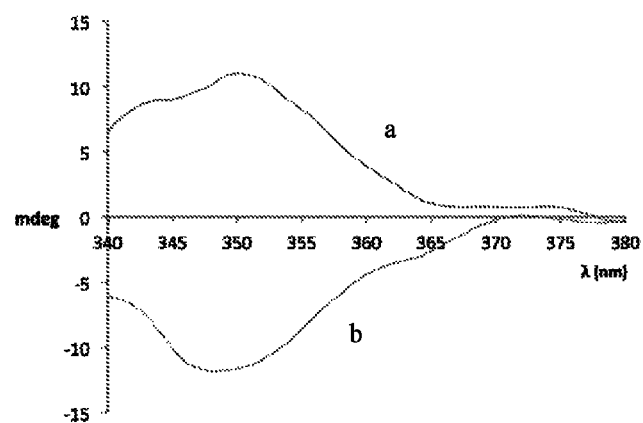
FIG. 78 is the CD spectra obtained using 2 and (R)-29 (blue (a)) and (S)-29 (red (b)).
Figure 79:
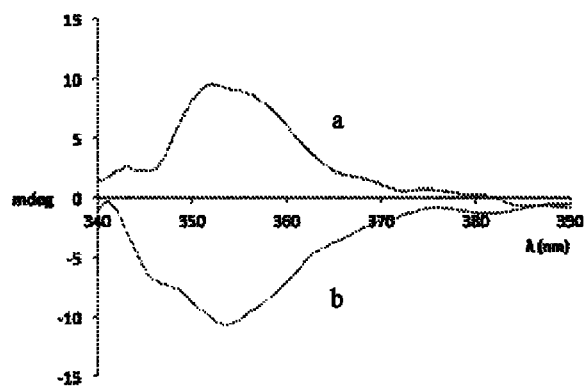
FIG. 79 is the CD spectra obtained using 2 and (R)-30 (blue (a)) and (S)-30 (red (b)).

A solution of 2 (2.86 mg, 0.01 mmol) and 9 (4.24 mg, 0.02 mmol) in 1 mL of a dry THF:EtOH mixture (1:1 v/v) was prepared. Then, $Et_2Zn$ (10 µl, 0.01 mmol, 1M in hexanes) was added and the mixture was stirred for 20 minutes. Electrospray mass spectrometry (positive ion mode) showed the presence of a bimetallic complex containing two equivalents of 2 and Zn, four equivalents of 9, and one equivalent of ethanol (FIG. 53).

A mixture of 2 (2.86 mg, 0.01 mmol) and $B(OMe)_3$ (1.04 mg, 0.01 mmol) was stirred in dry $CHCl_3$ for 10 minutes. To this solution was added 23 (1.58 mg, 0.01 mmol). After stirring an additional 5 minutes, $Et_3N$ (1.02 mg, 0.01 mmol) was added, and the solution was subjected to ESI-MS analysis (negative ion mode). A complex containing equimolar amounts of 2, boron, and 23 was detected.

Example 15—CD and UV Experiments: Amines and Amino Alcohols

A stock solution of 2 (0.01 M) in anhydrous THF was prepared and 350 µL portions were placed into 4 mL vials. To each vial, 50 µL, of a $Et_2Zn$ solution (0.07 M in hexanes) was added. Solutions of substrates 8 (0.035 M in anhydrous $CHCl_3$) and 9-20 (0.07 M in anhydrous $CHCl_3$) were prepared. To each vial containing 2 and $Et_2Zn$ was added 100 µL, of the substrate solution. The mixtures were stirred for 5 minutes and CD analyses were conducted using sample concentrations of $3.0 \times 10^{-4}$ M in anhydrous diethyl ether. The CD spectra were collected with a standard sensitivity of 100 mdeg, a data pitch of 0.5 nm, a bandwidth of 1 nm, a scanning speed of 500 nm $s^{-1}$ and a response of 0.5 s using a quartz cuvette (1 cm path length). The data were baseline corrected and smoothed using a binomial equation. Control experiments with 8-20 ($3.0 \times 10^{-4}$ M) did not show any CD signal at the wavelengths of interest. See FIGS. 55-68.

Example 16—CD and UV Experiments: α-Hydroxy Carboxylic Acids

A stock solution of 2 (2.86 mg, 0.01 mmol) in anhydrous $CHCl_3$ was prepared and 350 µL portions were placed into 4 mL vials containing molecular sieves. Solutions of substrates 21-24 were prepared (0.07 M in anhydrous ACN) and 50 µL, portions were added to each vial containing 2. Next, $B(OMe)_3$ (50 µL, 0.07 M in THF) was added to each vial and the mixture was stirred for 5 minutes, followed by addition of $Et_3N$ (50 µL, 0.07 M in $CHCl_3$). CD analyses were conducted using sample concentrations of $3.0 \times 10^{-4}$ M in anhydrous diethyl ether. All spectra were obtained utilizing the same instrumental settings as described for the analysis of substrates 8-20. See FIGS. 69-73.

Example 17—CD and UV Experiments: Amino Acids

To 4 mL vials containing substrates 25-30 (0.01 mmol) was added a stock solution of 2 (2.86 mg, 0.01 M) in anhydrous ACN and $B(OMe)_3$ (1.1 µL, 0.01 mmol). The CD analyses were conducted within 5 minutes using sample concentrations of $3.0 \times 10^{-4}$ in anhydrous $CHCl_3$. All spectra were obtained utilizing the same instrumental settings as described for substrates 8-20. See FIGS. 74-79.

Example 18—Sensing of Primary Amines with 2-Formyl-4-Methoxyphenylboronic Acid (31) and Ligand 2

Figure 80:
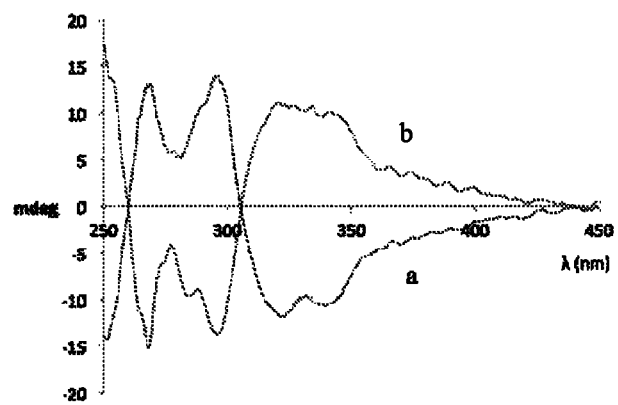
FIG. 80 is the CD spectra obtained using 2 and (R)-32 (blue (a)) and (S)-32 (red (b)).
Figure 81:
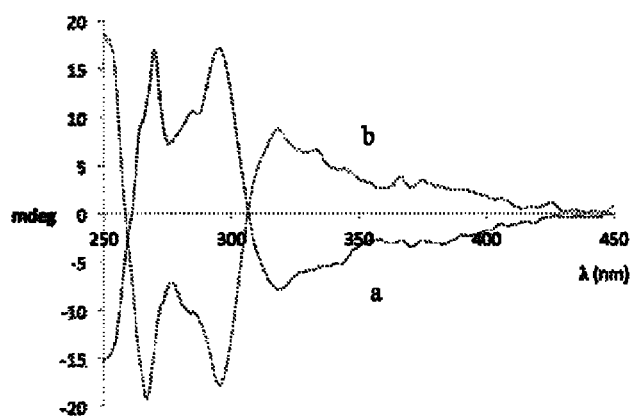
FIG. 81 is the CD spectra obtained using 2 and (R)-33 (blue (a)) and (S)-33 (red (b)).
Figure 82:
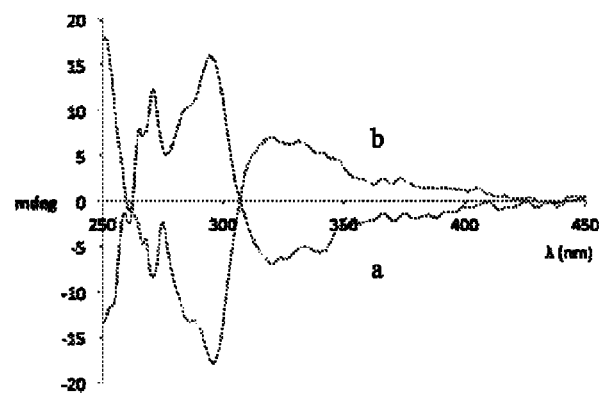
FIG. 82 is CD spectra obtained using 2 and (R)-11 (blue (a)) and (S)-11 (red (b)).

A stock solution of 2 (0.00375 M in anhydrous $CHCl_3$) was prepared and 350 µL portions were placed into 4 mL vials. To each vial was added 20 µL of the boronic acid (0.0657 M in anhydrous DMSO) and substrates 32, 33, and 11 (0.0675 M in anhydrous $CHCl_3$). The mixtures were stirred for 5 minutes and CD analyses were conducted using sample concentrations of $3.75 \times 10^{-5}$ M in anhydrous $CHCl_3$. All spectra were obtained utilizing the same instrumental settings as described for substrates 8-20. See FIGS. 80-82.

Example 19—Comparison of the CD Effects Measured with Stereodynamic Ligands 1 and 2

Figure 83:
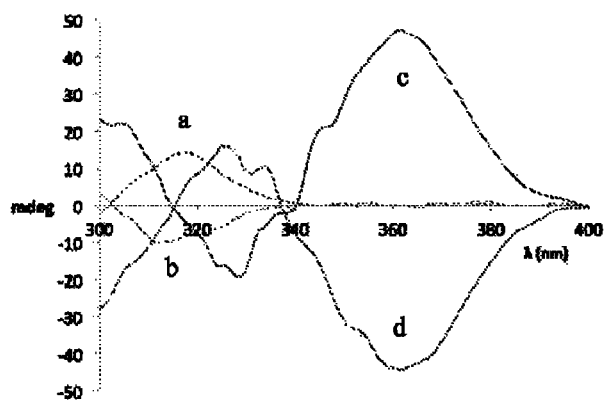
FIG. 83 is the CD spectra obtained with the Zn complexes derived from 1 and (1R,2R)-8 (dashed blue (a)) or (1S,2S)-8 (dashed red (b)) and the analogues derived from 2 and (1R,2R)-8 (solid blue (c)) or (1S,2S)-8 (solid red (d)).

A solution of 1, $Et_2Zn$, and 8 was prepared as described above for the experiments with 2 in order to compare the CD responses of the corresponding Zn complexes. The CD experiments were performed at $4.5 \times 10^{-4}$ M in anhydrous diethyl ether. See FIG. 83.

Figure 84:
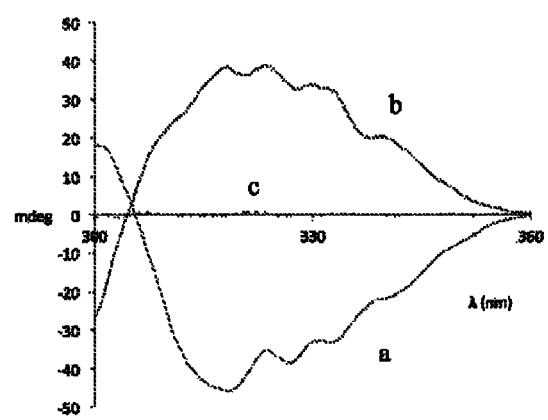
FIG. 84 is the CD spectra obtained with the boron derived complexes containing 2 and (R)-21 (blue (a)) and (S)-21 (red (b)) and the analogue derived from 1 and (R)-21 (dashed blue (c)).

A solution of 1, $B(OMe)_3$, and 21 was prepared as described above for 2 in order to compare the CD responses of the corresponding boron complexes. The CD experiments were performed at $4.5 \times 10^{-4}$ M in anhydrous $CHCl_3$. See FIG. 84.

A solution 31 and substrates 32, 33, or 11 was prepared as described above for 2 in order to compare the CD responses of the corresponding imine complexes in the absence of ligand. The CD experiments were performed at $3.75 \times 10^{-5}$ M in anhydrous $CHCl_3$. See FIGS. 85-87.

Example 20—Quantitative ee Analysis

Figure 88:
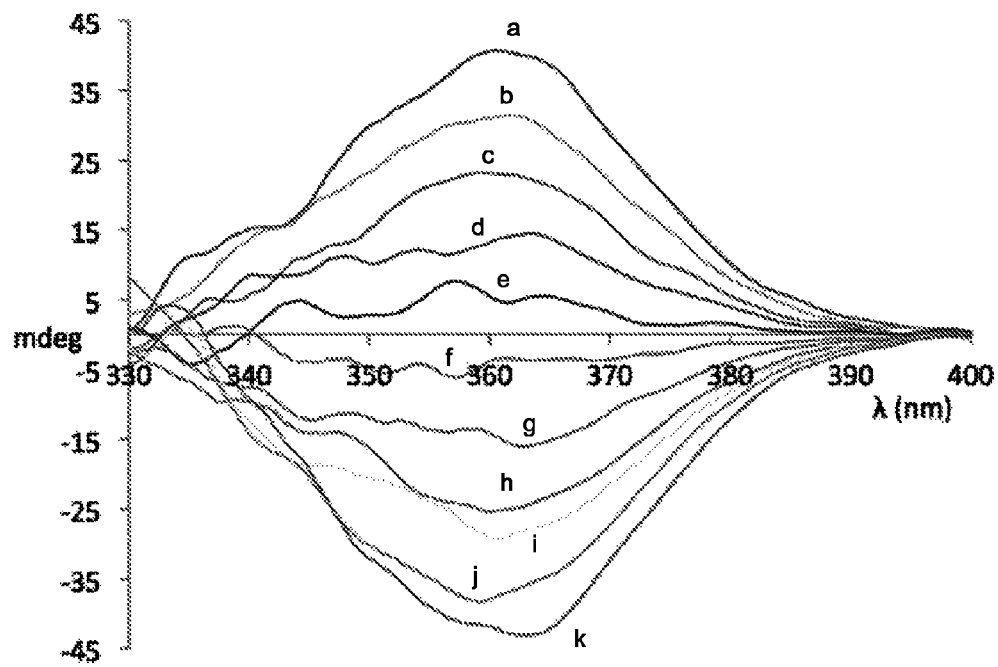
FIG. 88 is the CD spectra of the Zn complex obtained with 2 and scalemic samples of 8. a: +100; b: +80; c: +60; d: +40; e: +20; f: 0; g: −20; h: −40; i: −60; j: −80; k: −100.
Figure 89:
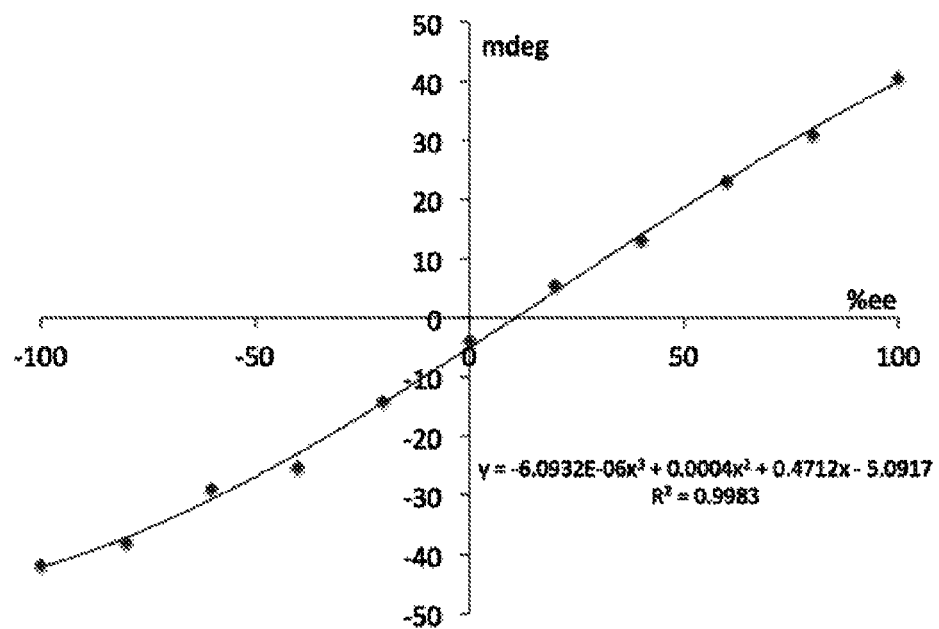
FIG. 89 is a plot showing the exponential relationship between the CD amplitudes at 360 nm and the enantiomeric excess of 8.

A calibration curve was constructed using samples of the Zn complex prepared with 2 and 8 at varying ee. Stock solutions of 2 (0.005 M) and 8 (0.005 mmol) with varying enantiomeric composition (+100, +80, +60, +40, +20, 0, −20, −40, −60, −80, −100 ee) were prepared. To these solutions was added $Et_2Zn$ (5 µL, 1 M in hexanes, 0.005 mmol). After 5 minutes, CD analysis was carried out as described above at $3.0 \times 10^{-4}$ M in anhydrous diethyl ether (FIG. 88). The Cotton effect amplitudes at 360 nm were plotted against the enantiomeric excess of 8 (FIG. 89).

Five scalemic samples of 8 were prepared and subjected to CD analysis with 2 and $Et_2Zn$ as described above. Using the regression equation obtained from the calibration curve and the CD amplitudes measured at 360 nm, the enantiomeric excess of these samples was determined. See Table 3.

TABLE 3

Comparison of the actual and the experimentally determined ee's of five scalemic samples of 8 using the CD readout of 2 at 360 nm.

| Actual % ee | Calculated % ee |
|---|---|
| 87.0 | 84.1 |
| 12.0 | 15.4 |
| −26.0 | −23.5 |
| −68.0 | −65.4 |
| −89.0 | −87.0 |

Figure 90:
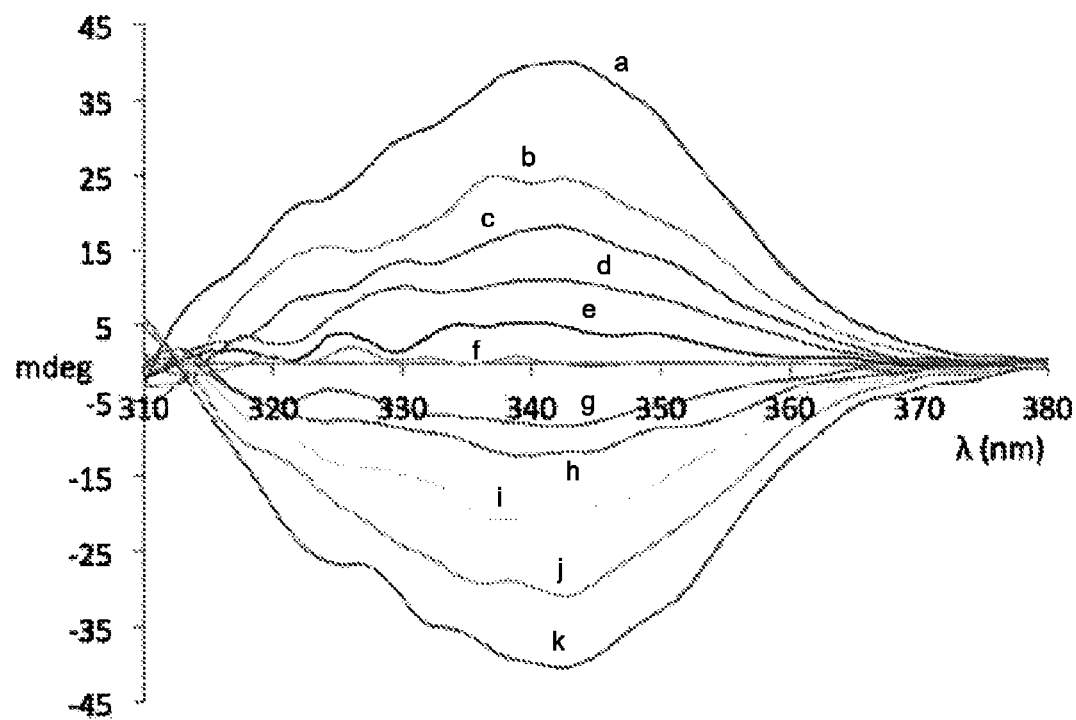
FIG. 90 is the CD spectra of the Zn complex obtained with 2 and scalemic nonracemic samples of 18 at $3.0 \times 10^{-4}$ M in diethyl ether.
Figure 91:
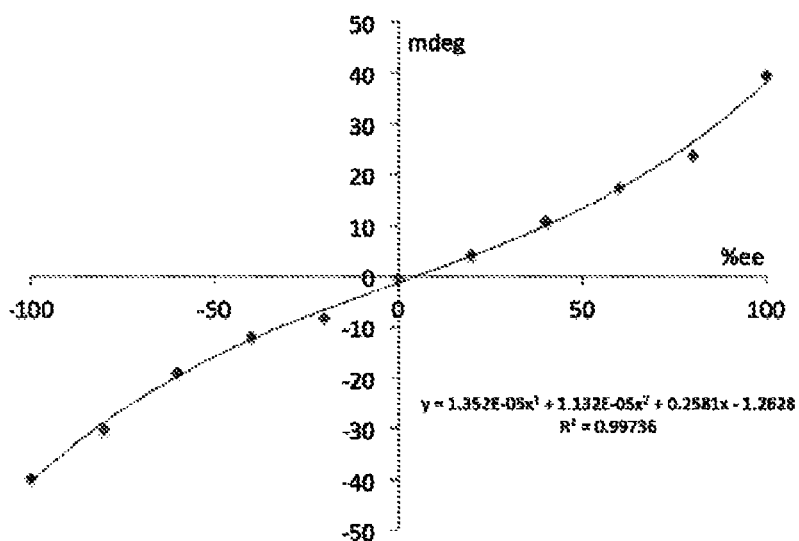
FIG. 91 is a plot showing the exponential relationship between the CD amplitudes at 360 nm and the enantiomeric excess of 18.

A calibration curve was constructed using samples of the Zn complex prepared with 2 and 18 at varying ee. Stock solutions of 2 (0.005 M) and 18 (0.01 M) with varying enantiomeric composition (+100, +80, +60, +40, +20, 0, −20, −40, −60, −80, −100 ee) were prepared. To these solutions was added Et$_2$Zn (5 μL, 1 M in hexanes, 0.005 mmol). After 5 minutes, CD analysis was carried out as described above at 3.0×10$^{-4}$ M in anhydrous diethyl ether (FIG. 90). The Cotton effect amplitudes at 340 nm were plotted against the enantiomeric excess of 18 (FIG. 91).

Five scalemic samples of 18 were prepared and subjected to CD analysis with 2 and Et$_2$Zn as described above. Using the regression equation obtained from the calibration curve and the CD amplitudes measured at 360 nm, the enantiomeric excess of these samples was determined. See Table 4.

TABLE 4

Comparison of the actual and the experimentally determined ee's of five scalemic samples of 18 using the CD readout of 2 at 340 nm.

| Actual % ee | Calculated % ee |
|---|---|
| 87.0 | 84.4 |
| 76.0 | 76.7 |
| 12.0 | 14.9 |
| −26.0 | −27.2 |
| −89.0 | −87.2 |

Example 21—Investigation of the Rotational Energy Barrier of Biphenols Generally HPLC experiments with 1 and 2 on a variety of chiral columns, including (S,S)-Whelk-O 1, Chiralcel® OD and Chiralpak® IA, did not show a sign of enantioseparation even at very low temperatures (−60° C.). Therefore diester 3 was prepared and the isopropyl groups used as an NMR probe to determine the barrier to rotation about the aryl-aryl bond.

Example 22—Investigation of the Rotational Energy Barrier of Biphenols: Synthesis and Characterization of Diester 1,1'-Biphenyl-2,2'-Diol Diisobutyrate (3)

1,1'-Biphenyl-2,2'-diol diisobutyrate (3) was synthesized as shown in Scheme 8.

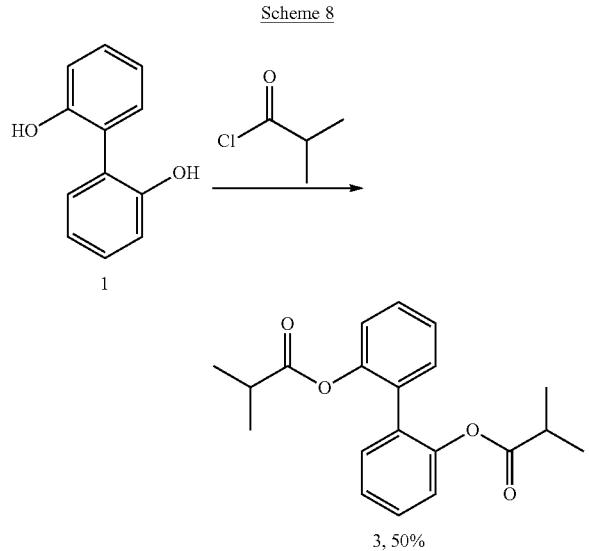

Scheme 8

Figure 92A:
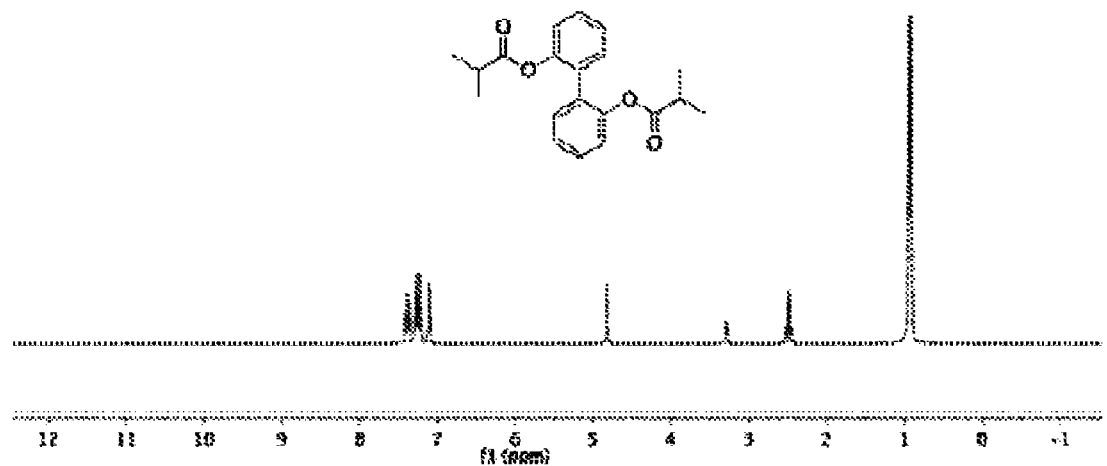
FIGS. 92A-B are the $^1$H NMR (FIG. 92A) and $^{13}$C NMR (FIG. 92B) spectra of 3 in $CD_3OD$.
Figure 92B:
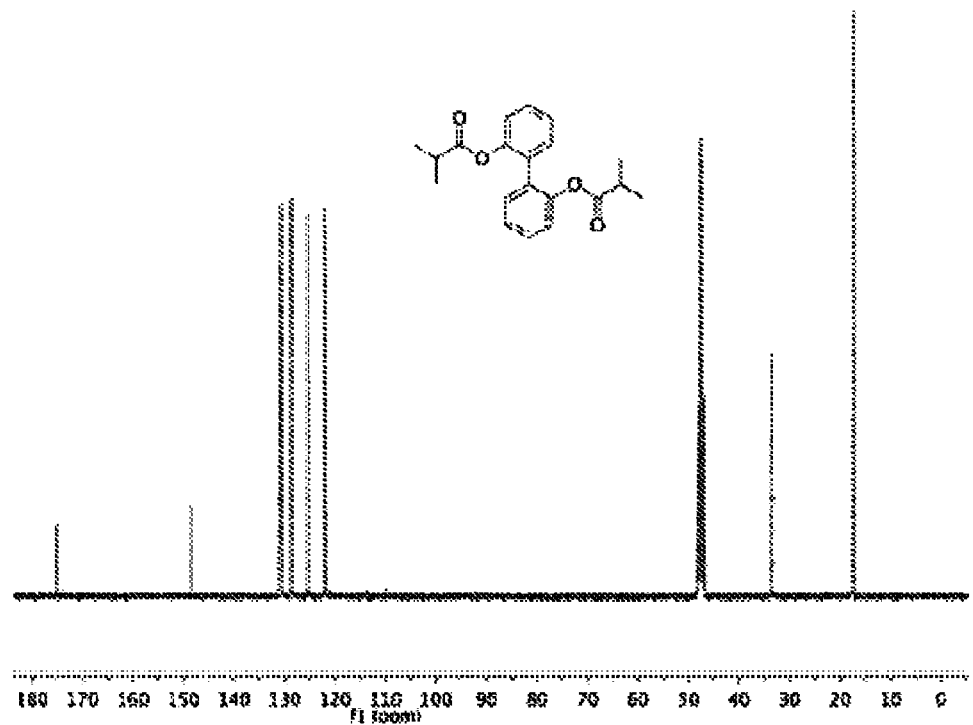

2,2'-Biphenol 1 (50 mg, 0.269 mmol) and pyridine (65 μL, 0.81 mmol) were dissolved in 5 mL of dichloromethane and cooled to 0° C. Isobutyryl chloride (84 μL, 0.81 mmol) was added and the mixture was slowly warmed to room temperature and stirred for 4 hours. The reaction was quenched with 1M HCl and extracted with dichloromethane. The combined organic layers were washed with 0.5M NaOH, dried over MgSO$_4$ and concentrated in vacuo. Purification by flash chromatography on silica gel (CH$_2$Cl$_2$:hexanes 1:1) afforded 44 mg (0.14 mmol, 50%) of 1,1'-biphenyl-2,2'-diol diisobutyrate (3) as a colorless oil. $^1$H NMR (FIG. 92A) (CD$_3$OD): δ=0.92 (d, J=7.0 Hz, 6H), 2.44 (sept, J=7.0 Hz, 2H), 7.09 (dd, J=8.1 Hz, 0.7 Hz, 2H), 7.21 (dd, J=7.6 Hz, 1.5 Hz, 2H), 7.25 (ddd, J=8.1 Hz, 7.6 Hz, 0.7 Hz, 2H), 7.36 (ddd, J=7.6 Hz, 7.6 Hz, 1.5 Hz, 2H). $^{13}$C NMR (FIG. 92B) (CD$_3$OD): δ=17.5, 33.6, 122.1, 125.4, 128.7, 130.7, 130.9, 148.4, 175.3.

Figure 93:
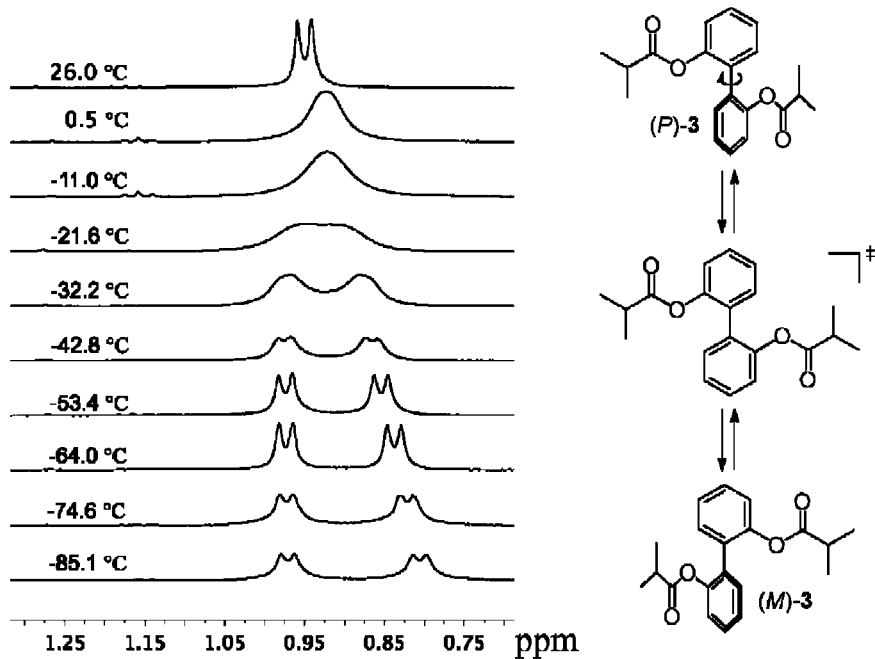
FIG. 93 is the $^1$H NMR spectra of 3 at various temperatures. Only the coalescence of the diastereotopic methyl signals is shown.

Example 23—Investigation of the Rotational Energy Barrier of Biphenols Variable-Temperature NMR Spectroscopy Diester 3 was dissolved in CD$_3$OD (0.05 M) and $^1$H NMR spectra were obtained at various temperatures (FIG. 93). The temperature readings were corrected according to a standard procedure with methanol (Ammann et al., J. Magn. Reson. 46:319-21 (1982), which is hereby incorporated by reference in its entirety which is hereby incorporated by reference in its entirety). The coalescence temperature, T$_c$, was determined as −12.3° C. (260.8 K) and Δ$^υ$ was 70.97 Hz at −85.14° C. The energy barrier to rotation about the aryl-aryl bond was calculated as 52.6 kJ/mol using equation (1) (Gutowsky & Holm, J. Chem. Phys. 25:1228-34 (1956), which is hereby incorporated by reference in its entirety).

$$\Delta G^{\ddagger} = \left[[4.575 \times 10^{-3} T_c]\left[9.972 + \log\left(\frac{T_c}{\Delta \upsilon}\right)\right]\right] \times 4.186 \quad (1)$$

Example 24—Crystallography

A single crystal of the complex formed from 2, (1S,2S)-8, and Et$_2$Zn was obtained by slow diffusion of diethyl ether into a concentrated chloroform solution. Single crystal X-ray analysis was performed at 100 K using a Siemens platform diffractometer with graphite monochromated Mo-Kα radiation (λ=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameters. The asymmetric unit contains two unique complexes having (1S,2S,P,M) configuration (depicted in FIGS. 94A-B as complexes A (FIG. 94A) and B (FIG. 94B)) and one diethyl ether molecule. Formula: C$_{68}$H$_{52}$N$_4$O$_4$Zn$_2$, M=580.48, crystal dimensions 0.4×0.2×0.1 mm, primitive, space group P1, a=12.5034(16) Å, b=14.2812(18) Å, c=16.244(2) Å, α=85.326(2)°, β=78.118(2)°, γ=78.408(2)°, V=2778.1 Å$^3$, Z=4, ρ$_{calcd}$=1.388 g cm$^{-3}$. The same complex stoichiometry of 2:2:2 (2, Zn, 8) was obtained by crystallographic analysis of a single crystal prepared by precipitation from an anhydrous ethanol solution. See Table 5.

TABLE 5

Important crystallographic distances [Å] and angles [°].

|  | A | B |
|---|---|---|
| Zn1—O1 | 1.926 | 1.942 |
| Zn1—O2 | 2.087 | 2.041 |
| Zn1—O3 | 1.979 | 2.029 |
| Zn2—O2 | 2.001 | 1.993 |
| Zn2—O3 | 2.076 | 2.029 |
| Zn2—O4 | 1.917 | 1.943 |
| Zn1—N1 | 2.144 | 2.143 |
| Zn1—N2 | 2.095 | 2.085 |
| Zn2—N3 | 2.087 | 2.121 |
| Zn2—N4 | 2.161 | 2.149 |
| L1 aryl-aryl torsion angle | 46.7 | 50.7 |
| L2 aryl-aryl torsion angle | 41.8 | 51.1 |

Figure 95:
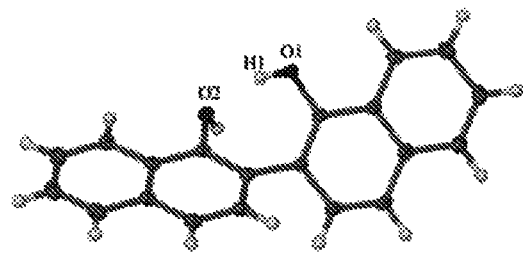
FIG. 95 is a thermal ellipsoid plot (50% probability) of a single crystal of 2.

A single crystal of 2 was obtained by slow evaporation of a chloroform solution (0.017 M). Single crystal X-ray analysis was performed at 100 K using a Siemens platform diffractometer with graphite monochromated Mo-Kα radiation ($\lambda$=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameters. The asymmetric unit contains one unique molecule of 2 (FIG. 95). Formula $C_{12}H_{14}O_2$, M=286.31, crystal dimensions 0.6× 0.5×0.2 mm, monoclinic space group P21/c, a=13.5726(13) Å, b=12.8067 Å, c=8.1004(8) Å, α=90.00 β=90.0010(10) γ=90.00 V=1390.7(2) Å$^3$, Z=4, $\rho_{calcd}$=1.3674 g cm$^{-3}$. The aryl-aryl torsion angle was calculated as 29.24°.

Example 25—CD Sensing Using Diethyl Zinc and Bis(2-Hydroxy-1-Naphthyl)Methanone (34)

Figure 96:
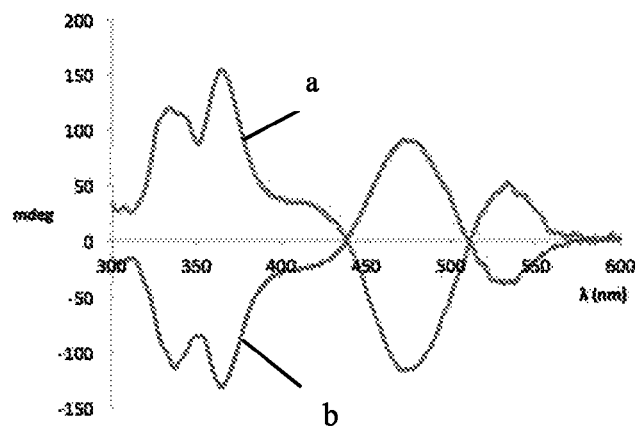
FIG. 96 is the CD spectra obtained using ligand 34 and (1R,2R)-8 (a) and (1S,2S)-8 (b) in $ZnEt_2$.

Ligand 34 (3.14 mg, 0.01 mmol) and diamine 8 (2.12 mg, 0.01 mmol) were dissolved together in anhydrous THF. To this solution was added 10 μL of ZnEt$_2$ (1 M in hexanes). The mixture was stirred for 5 minutes and CD analysis was conducted using sample concentrations of 3.0×10$^{-4}$ M in anhydrous diethyl ether (FIG. 96). The CD spectra were collected with a standard sensitivity of 100 mdeg, a data pitch of 0.5 nm, a bandwidth of 1 nm, a scanning speed of 500 nm s$^{-1}$ and a response of 0.5 s using a quartz cuvette (1 cm path length). The data was baseline corrected and smoothed using a binomial equation. See Scheme 9.

Scheme 9

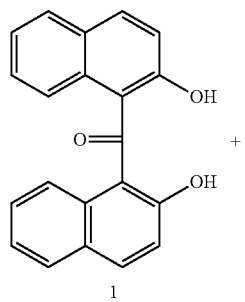

1

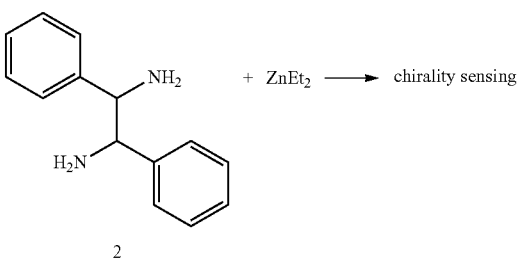

2

Discussion of Examples 11-25

A search for universal CD probes that are capable of fast and sensitive detection of the chirality and ee of a large variety of important targets, i.e., amines, diamines, amino alcohols, amino acids, and α-hydroxy carboxylic acids, was initiated.

It was envisioned that this can be accomplished with a chromophoric tropos ligand that (a) reacts with Et$_2$Zn and B(OMe)$_3$ toward stable complexes capable of binding stoichiometric amounts of a wide variety of N- and O-donating compounds, (b) is prone to an instantaneous and distinctive chiral amplification process upon coordination of a chiral substrate to such a complex, and (c) provides a strong CD response to the binding event at high wavelengths and low concentration. These considerations pointed to biphenol 1 and binaphthol 2, and it was decided to first use commercially available 1 to assess the stereodynamic properties and suitability for chiroptical sensing applications (Scheme 10).

Scheme 10

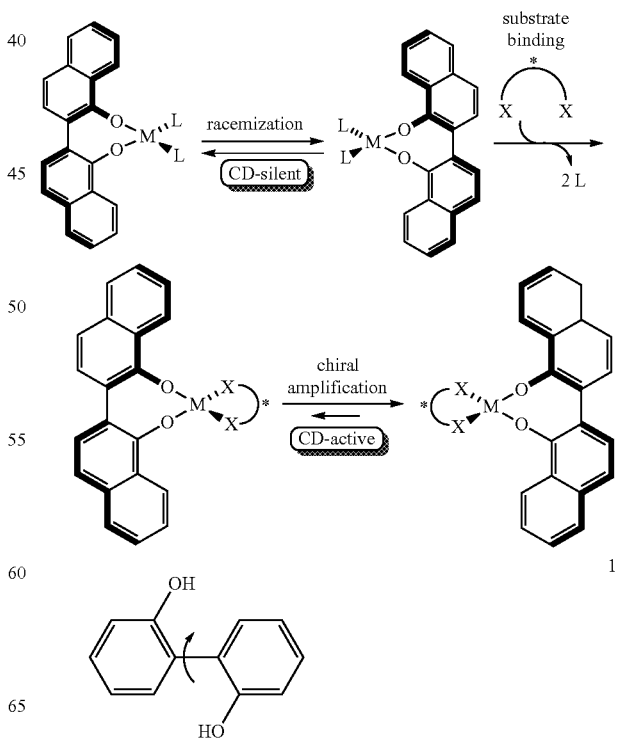

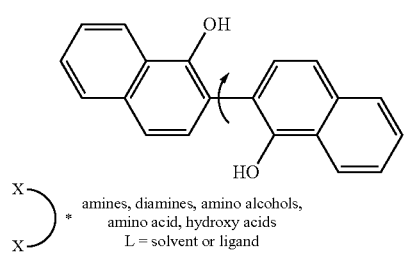

Biphenol and its derivatives have found widespread applications as amplifiers of molecular chirality in liquid crystals (Eelkema & Feringa, *J. Am. Chem. Soc.* 127:13480 (2005); Eelkema & Feringa, *Org. Lett.* 8:1331 (2006), which are hereby incorporated by reference in their entirety), because hydrogen bonding between biphenols and diamines or amino alcohols generates weak Cotton effects (Mizutani et al., *Tetrahedron Lett.* 38:1991 (1997); Ishii et al., *Tetrahedron Lett.* 47:8221 (2006); Etxebarria et al., *J. Org. Chem.* 74:8794 (2009), which are hereby incorporated by reference in their entirety), and as practical means to improve the efficiency of catalytic enantioselective reactions (Reetz & Neugebauer, *Angew. Chem. Int. Ed.* 38:179 (1999); Mikami et al., *Angew. Chem. Int. Ed.* 39:3532 (2000); Walsh et al., *Chem. Rev.* 103:3297 (2003); Mikami & Yamanaka, *Chem. Rev.* 103:3369 (2003); Reetz & Li, *Angew. Chem. Int. Ed.* 44:2959 (2005); Aikawa et al., *Angew. Chem. Int. Ed.* 48:6073 (2009); Aikawa & Mikami, *Chem. Comm.* 48:11050 (2012), which are hereby incorporated by reference in their entirety). Mikami, Kwit and others have reported that the addition of biphenols to metal-catalyzed reactions increases yield, asymmetric induction, and in some cases the reaction rate (Mikami & Matsukawa, *Nature* 385:613 (1997); Gajewy et al., *Monatsh. Chem.* 143:1045 (2012); Ueki et al., *Synlett* 1889 (2001); Chavarot et al., *Tetrahedron: Asymm.* 9:3889 (1998); Bolm & Beckmann, *Chirality* 12:523 (2000); Gajewy et al., *Eur. J. Org. Chem.* 307 (2013), which are hereby incorporated by reference in their entirety). The dynamic stereochemistry of biphenol and its analogues is critical in any of the applications mentioned above. Surprisingly, experimental racemization data for these compounds have not been reported and little is known about other tropos ligands. Maier and Trapp recently determined the enantioconversion barrier of a series of biphep (2,2'-bis(diphenylphosphino)-1,1'-biphenyl) ligands by dynamic HPLC (Maier & Trapp, *Angew. Chem. Int. Ed.* 51:2985 (2012); Wolf, Review, *Chem. Soc. Rev.* 34:595 (2005) (dynamic chromatography), which are hereby incorporated by reference in their entirety). These ligands racemize at room temperature but may become conformationally stable upon formation of a metal complex (Tudor et al., *Organometallics* 19:4376 (2000), which is hereby incorporated by reference in its entirety). Gagné observed that coordination of biphep to platinum increases its rotational energy barrier by approximately 30% from 90 kJ/mol (398 K) to 123 kJ/mol (382 K) (Desponds & Schlosser, *Tetrahedron Lett.* 37:47 (1996), which is hereby incorporated by reference in its entirety).

It was first attempted to determine the racemization kinetics of 1 by dynamic HPLC at low temperatures. The screening of several chiral stationary phases even at −60° C. did not show a sign of enantioseparation, and it was therefore decided to resort to variable-temperature NMR analysis of 1,1'-biphenyl-2,2'-diol diisobutyrate 3 (FIG. 93; see Example 23, supra). Analysis of the coalescence of the diastereotopic methyl protons at low temperature allowed for the determination of the rotational barrier, $\Delta G^{\ddagger}$, as 52.6 kJ/mol. This value is in good agreement with Fujimura's DFT calculation suggesting a racemization barrier of 48.1 kJ/mol for 1 (Sahnoun et al., *J. Phys. Chem. A.* 110:2440 (2006), which is hereby incorporated by reference in its entirety). Based on Gagné's study with biphep and because the buttressing effect of the fused benzene rings on the ortho-substituents in 1 is expected to increase the rotational energy barrier by no more than 10% (CHRISTIAN WOLF, DYNAMIC STEREOCHEMISTRY OF CHIRAL COMPOUNDS 86 (2008), which is hereby incorporated by reference in its entirety), it was concluded that both 1 and 2 undergo instantaneous enantioconversion at room temperature even in a metal complex.

To corroborate the chirality sensing strategy depicted in Scheme 10, a stoichiometric amount of enantiopure 1,2-diphenyl-1,2-diaminoethane was added to a complex formed from biphenol 1 and diethyl zinc at 3.0 $10^{-4}$ M in diethyl ether. A weak CD response above 300 nm was indeed observed, but the complex proved unstable and quickly decomposed upon exposure to air. In an effort to improve the stability and to enhance the chiral amplification, tropos ligand 2 was synthesized with the expectation that this probe would give a stronger chiroptical readout and shift the CD signal to higher wavelengths (FIG. 95; see Example 12, supra) (2,2'-binaphthalene-1,1'-diol, 2, is the stereodynamic analogue of BINOL (1,1'-binaphthalene-2,2'-diol). Bromination of 1-naphthol with NBS afforded 4, which was methylated with MeI to give 5. Conversion to the boronic acid 6 was accomplished by lithiation and treatment with B(OMe)$_3$. Suzuki coupling of 5 and 6 gave biaryl 7, and demethylation with BBr$_3$ finally generated 2 in high yield.

Enantioselective recognition of diamine 8 with 2 was found to give a red-shifted and much stronger CD signal than 1 under identical conditions (FIG. 97A). The substrate scope was then expanded to include monoamines 9-13 (FIG. 97B) and primary and tertiary amino alcohols 14-20 (FIG. 97C). The CD sensing of all aliphatic and aromatic compounds tested with the zinc binaphtholate gave strong Cotton effects showing a maximum at approximately 350 nm (FIGS. 97A-C; see Example 15, supra). The CD signals appear immediately after the samples are mixed, and all measurements were taken within 5 minutes. It was found that the binaphtholates prepared from Mg(Ot-Bu)$_2$, Zn(OTf)$_2$, and Al(Oi-Pr)$_3$ are also suitable for CD sensing but superior results were generally obtained with Et$_2$Zn. A closer look at the sign of the maximum CD amplitudes reveals trends that allow prediction of the absolute configuration (Table 6). A positive CD maximum is observed for amines with S configuration while the opposite is true for R amines (entries 2-6). Amino alcohols having a single chiral center yield a positive couplet for the R enantiomer and a negative CD response at 350 nm for the S antipodes (entries 8-10). The opposite rule applies to amino alcohols with two chiral centers (entries 7 and 11-13).

TABLE 6

Chiroptical sensing of 8-30.

| Entry | Substrate Class | Substrate | $\Delta_{max}$ (mdeg)$^a$ | $\lambda_{max}$ | Predicted CD Signal$^b$ |
|---|---|---|---|---|---|
| 1 | DA | (1R,2R)-8 | +47 | 362 | + |
|   |   | (1S,2S)-8 | −44 |   | − |

TABLE 6-continued

Chiroptical sensing of 8-30.

| Entry | Substrate Class | Substrate | $\Delta_{max}$ (mdeg)[a] | $\lambda_{max}$ | Predicted CD Signal[b] |
|---|---|---|---|---|---|
| 2 | MA | (R)-9 | −28 | 351 | − |
|   |    | (S)-9 | +28 |     | + |
| 3 | MA | (R)-10 | −16 | 352 | − |
|   |    | (S)-10 | +21 |     | + |
| 4 | MA | (R)-11 | −12 | 351 | − |
|   |    | (S)-11 | +12 |     | + |
| 5 | MA | (R)-12 | −11 | 314[c] | − |
|   |    | (S)-12 | +12 |     | + |
| 6 | MA | (R)-13 | −10 | 346 | − |
|   |    | (S)-13 | +9 |     | + |
| 7 | AA | (1R,2S)-14 | −23 | 311[c] | − |
|   |    | (1S,2R)-14 | +22 |     | + |
| 8 | AA | (R)-15 | +13 | 348 | + |
|   |    | (S)-15 | −13 |     | − |
| 9 | AA | (R)-16 | +20 | 345 | + |
|   |    | (S)-16 | −17 |     | − |
| 10 | AA | (R)-17 | +16 | 348 | + |
|    |    | (S)-17 | −18 |     | − |
| 11 | AA | (1R,2S)-18 | +59 | 345 | + |
|    |    | (1S,2R)-18 | −58 |     | − |
| 12 | AA | (1R,2S)-19 | +62 | 345 | + |
|    |    | (1S,2R)-19 | −56 |     | − |
| 13 | AA | (1R,2S)-20 | +70 | 350 | + |
|    |    | (1S,2R)-20 | −79 |     | − |
| 14 | HA | (R)-21 | −44 | 319 | − |
|    |    | (S)-21 | +41 |     | + |
| 15 | HA | (R)-22 | −30 | 318 | − |
|    |    | (S)-22 | +32 |     | + |
| 16 | HA | (R)-23 | −21 | 321 | − |
|    |    | (S)-23 | +19 |     | + |
| 17 | HA | (R)-24 | −23 | 315 | − |
|    |    | (S)-24 | +23 |     | + |
| 18 | AC | (R)-25 | +28 | 351 | + |
|    |    | (S)-25 | −25 |     | − |
| 19 | AC | (R)-26 | +19 | 352 | + |
|    |    | (S)-26 | −16 |     | − |
| 20 | AC | (R)-27 | +19 | 348 | + |
|    |    | (S)-27 | −19 |     | − |
| 21 | AC | (R)-28 | +14 | 349 | + |
|    |    | (S)-28 | −13 |     | − |
| 22 | AC | (R)-29 | +11 | 350 | + |
|    |    | (S)-29 | −11 |     | − |
| 23 | AC | (R)-30 | +9 | 354 | + |
|    |    | (S)-30 | −10 |     | − |

[a]All CD measurements were conducted within 5 minutes after mixing the probe, Et$_2$Zn or B(OMe)$_3$ and the substrate at $3.0 \times 10^{-4}$ M in Et$_2$O or CHCl$_3$.
[b]Predicted sign at 350 nm for monoamines: R is negative, S is positive; amino alcohols: R is positive, S is negative; amino alcohols with two chiral centers (the absolute configuration at the amino group is determined): R is negative, S is positive. Note that due to nomenclature rules the amino moiety in aminoindanol is at C-1 but at C-2 in the other amino alcohols; α-hydroxy acids: R is negative, S is positive; amino acids: R is positive, S is negative.
[c]The CD sensing of 12 and 14 also yields a signal at 350 nm. DA = diamine, MA = monoamine, AA = amino alcohol, HA = hydroxy acid, AC = amino acid.

Figure 94A:
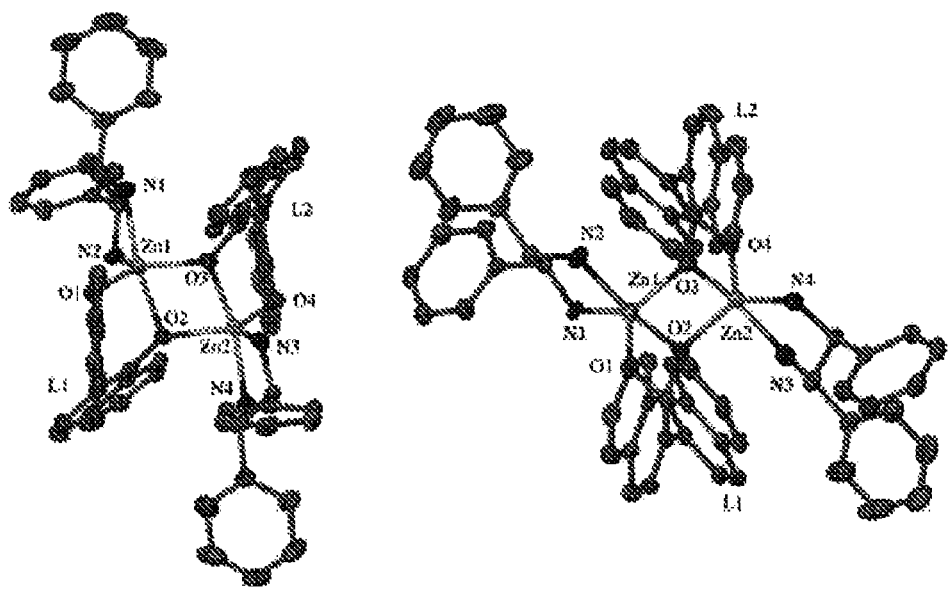
FIGS. 94A-B are thermal ellipsoid plots (50% probability) of Complex A (FIG. 94A) and Complex B (FIG. 94B) showing the view along the aryl-aryl bond of 2 (left) and side view of 2 (right). All hydrogens omitted for clarity. Selected distances [Å] and angles [°] for complex A: Zn1-O1 1.926, Zn1-O2 2.087, Zn1-N1 2.144, Zn1-N2 2.095, L1 aryl-aryl torsion angle 46.7, L2 aryl-aryl torsion 41.8. Complex B: L1 aryl-aryl torsion 50.7, L2 aryl-aryl torsion 51.1.
Figure 94B:
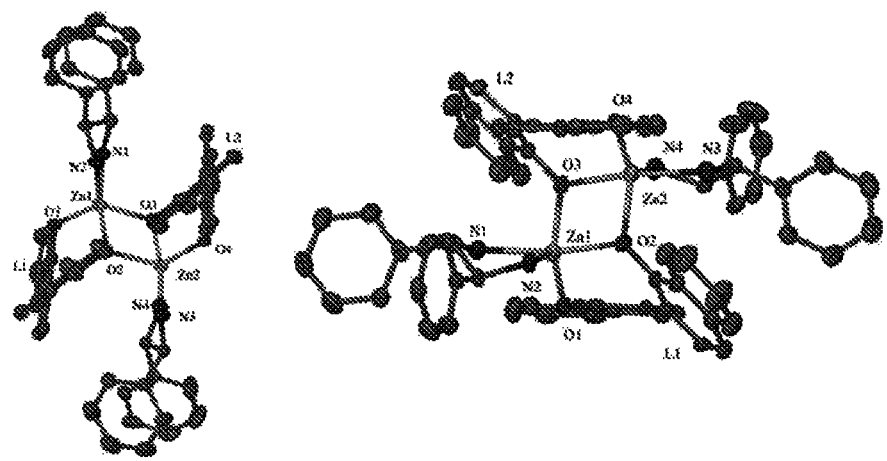

Mass spectrometric analysis of solutions containing 8 and 9, respectively, showed a bimetallic species with a stoichiometry of 2:2:2 (2:Zn:8) and 2:2:4 in the case of monodentate 9 (see Example 14, supra). Despite the important role in asymmetric catalysis, very little about the structure of (biphenolate)- and (binaphtholate)Zn(diamine) complexes is known. Walsh et al. reported the X-ray structure of a monometallic zinc complex carrying 3,3'-diphenyl-BINOLate and a bulky secondary diamine having the generally accepted 1:1:1 stoichiometry with a tetrahedral zinc center (Costa et al., J. Am. Chem. Soc. 124:6929 (2002), which is hereby incorporated by reference in its entirety). No other structural information on these complexes has been found in the literature. Because the complexes derived from 2 are stable in solution for several days, it was attempted to grow single crystals. Slow diffusion of diethyl ether into a chloroform solution of 2, Et$_2$Zn, and 8 gave blue single crystals. X-ray analysis showed two complexes in the asymmetric unit, both having a bimetallic structure with a 2:2:2 stoichiometry which is in agreement with the MS analysis (FIGS. 94A-B; see Example 24, supra). One oxygen of each binaphtholate bridges the two metal centers forming a four-membered μ-oxo ring, while each Zn carries one molecule of bidentate 8 to give a pentacoordinate bimetallic Zn complex. Both metal centers thus afford a slightly distorted bipyramidal geometry. Apparently, the formation of pentacoordinate bimetallic (binaphtholate)Zn(diamine) complexes is favored in the absence of steric hindrance, and it was assumed that this finding may prove invaluable for the interpretation of chiral induction and amplification effects in asymmetric catalysis and ee sensing, vide infra. The two binaphtholate ligands have opposite stereochemical bias in the crystal and give an overall (1S,2S,P,M) configuration. This was unexpected due to the strong CD output observed in solution and may be attributed to packing forces in the solid state.

For CD sensing of α-hydroxy acids 21-24 (FIG. 98A) and amino acids 25-30 (FIG. 98B), Et$_2$Zn was replaced with B(OMe)$_3$, following reports from Shan and Riguera on structurally related (BINOLate)borate complexes (Shan et al., Chin. J. Chem. 21:1373 (2003); Freire et al., Chem. Comm. 4147 (2008); Zhao et al., Angew. Chem. Int. Ed. 43:3461 (2004) (nonracemizing chiral boron receptors); Zhu et al., J. Am. Chem. Soc. 127:4260 (2005) (nonracemizing chiral boron receptors); Shabbir et al., Proc. Natl. Acad. Sci. 106:10487 (2009) (nonracemizing chiral boron receptors); Mirri et al., J. Am. Chem. Soc. 132:8903 (2010) (nonracemizing chiral boron receptors); Wu et al., J. Org. Chem. 76:5685 (2011) (nonracemizing chiral boron receptors); Bull et al., Acc. Chem. Res. 46:312 (2012) (nonracemizing chiral boron receptors), which are hereby incorporated by reference in their entirety). The employment of biphenol 1 as probe for CD analysis of 21 was ineffective and no CD response above 300 nm even at elevated concentrations was observed (FIGS. 98A-C). In contrast, the borate complexes obtained with binaphthol 2 and substrates 21-24 produced strong CD amplitudes at approximately 320 nm, and the expected formation of a negatively charged (binaphtholate)boron(α-alkoxy carboxylate) complex with 1:1:1 stoichiometry was confirmed by MS analysis (FIG. 98A (a), (b); see Example 16, supra). Again, the complex formation and subsequent chiroptical response of our probe were instantaneous and CD measurements were performed within 5 minutes. Inspection of the trend in Table 6 shows that substrates with R configuration display a negative CD couplet at 320 nm, while the opposite applies to the S enantiomers (entries 14-17). Finally, several amino acids were tested in the CD assay, and it was found that the instantaneous CD readout can be correlated to the absolute configuration of both aliphatic and aromatic substrates (FIG. 98B; see Example 17, supra). All R amino acids yielded a positive CD maximum at 350 nm while opposite CD responses were observed for the S enantiomers (entries 18-23).

Figure 85:
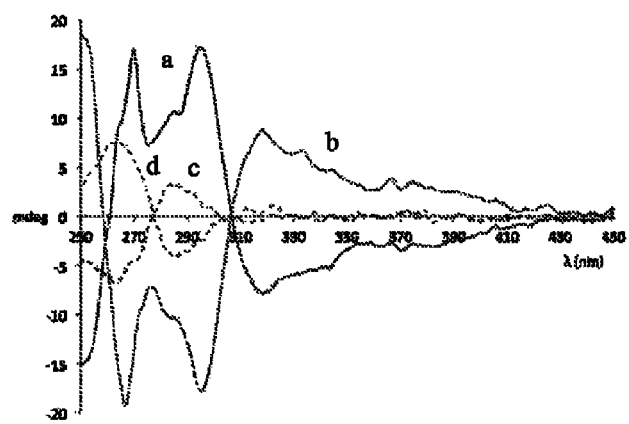
FIG. 85 is the CD spectra obtained with the imine-boron complex derived from 2, 31, and (R)-32 (solid blue (a)) or (S)-32 (solid red (b)). The spectra shown with dashed lines correspond to the condensation products of 31 with (R)-32 (dashed blue (c)) or (S)-32 (dashed red (d)) in the absence of 2. Concentrations were $3.75 \times 10^{-5}$ M in $CHCl_3$.
Figure 86:
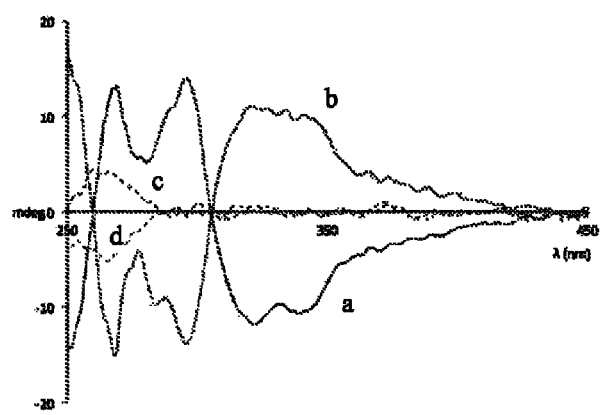
FIG. 86 is the CD spectra obtained with the imine-boron complex derived from 2, 31, and (R)-33 (solid blue (a)) or (S)-33 (solid red (b)), and the analogues derived from 1, 31, and (R)-33 (dashed blue (c)) or (S)-33 (dashed red (d)). Concentrations were $3.75 \times 10^{-5}$ M in $CHCl_3$.
Figure 87:
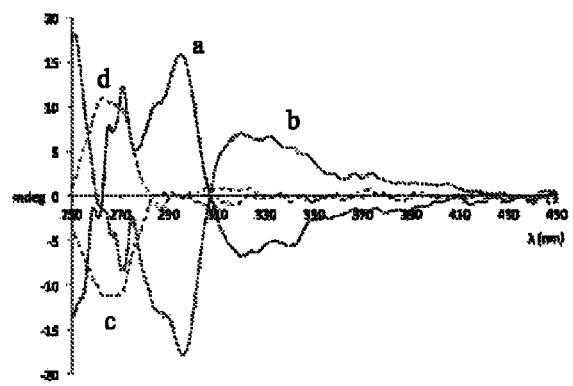
FIG. 87 is the CD spectra obtained with the imine-boron complex derived from 2, 31, and (R)-11 (solid blue (a)) or (S)-11 (solid red (b)) and the analogues derived from 1, 31, and (R)-11 (dashed blue (c)) or (S)-11 (dashed red (d)).

Recently, Anslyn, James and Bull introduced an attractive assay for the detection and ee analysis of primary amines that is based on a three-component assembly with enantiopure atropos BINOL and 2-formylphenylboronic acid (Metola et al., Chem. Sci. 3:156 (2012), which is hereby incorporated by reference in its entirety). It was assumed that the covalent binding of monoamines via condensation with a 2-formyl-4-methoxyphenylborate complex carrying binaphtholate 2 would yield a strong CD output originating from asymmetric amplification in the probe. Indeed, weak CD signals below 300 nm were obtained from the condensation product of 2-formyl-4-methoxyphenylboronic acid 31 and amines 11, 32, and 33, respectively (see Scheme 11). This largely changed when the same reaction was performed in the presence of one equivalent of 2, and significantly enhanced Cotton effects were observed at higher wavelengths (FIGS. 85 and 86; see Example 18, supra). This approach eliminates the use of enantiopure BINOL and solely relies on chiral amplification based on central-to-axial chirality induction with stereolabile binaphthol 2 serving as the CD reporter unit. Compared to the general chirality sensing method with B(OMe)$_3$ and 2 described above, the three-component assembly with 31 is limited to substrates having a primary amino group. But it is not applicable to sympathomimetic drugs such as N-methyl ephedrine, 20, and other amines or amino alcohols with secondary or tertiary amino functions.

Scheme 11

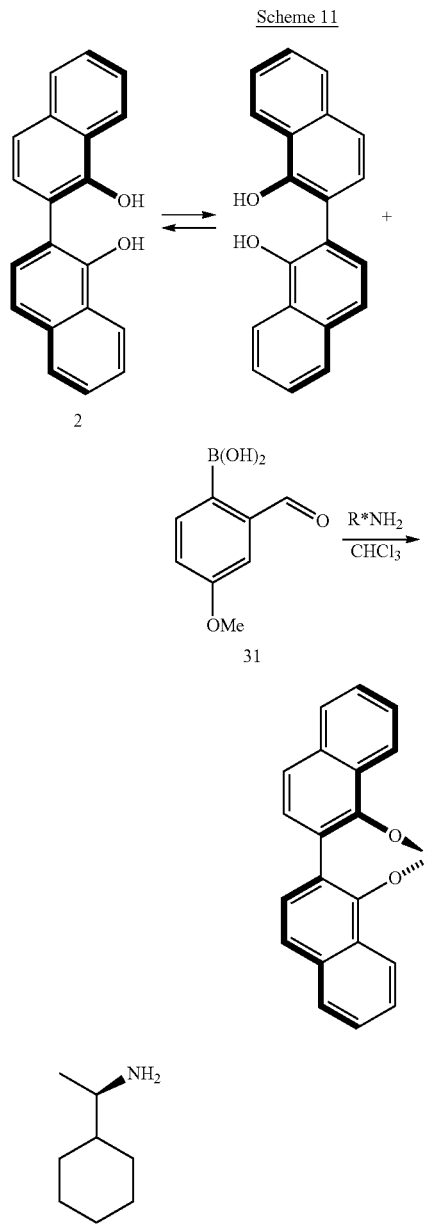

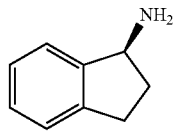

Although the use of stereodynamic probes in chirality sensing applications can involve complicated chiral recognition and amplification processes, a linear relationship between the ee of the substrate tested and the CD response of the chemosensor is typically assumed (nonlinear effects in asymmetric catalysis and chromatography are discussed in Satyanarayana et al., *Angew. Chem. Int. Ed.* 48:456 (2009); and Trapp & Schurig, *Tetrahedron Asymm.* 21:1334 (2010), which are hereby incorporated by reference in their entirety). The present examples show that this is not necessarily the case. In order to prove the efficiency of 2 for fast ee analysis, the CD readout at 360 nm was measured in the presence of nonracemic samples of 8 and 18. It was found that the chiroptical response of 2 to the enantiomeric substrate composition does not follow a linear trend, which is indicative of formation of homochiral and heterochiral aggregates (Trapp & Schurig, *Tetrahedron Asymm.* 21:1334 (2010), which is hereby incorporated by reference in its entirety) (FIGS. 90-91; see Example 20, supra). The observed nonlinear effect in ee sensing with the binaphtholate-Zn complex is in agreement with the MS and crystallographic detection of bimetallic Zn species, which one would expect to exist as a complex mixture of homo- and heterochiral adducts. Nonlinear regression plots provided the basis for accurate analysis of 10 unknown samples covering a wide ee range (Table 7). The experimentally obtained values were all within 3.4% of the actual ee compositions which is generally considered sufficient for HTS applications. It was also observed that a red shift in the UV spectrum occurs upon substrate recognition, which has potential for analysis of the total analyte concentration.

TABLE 7

Quantitative sensing results with different substrates.

| | (1R,2R)-8 | | | (1S,2R)-18 | | |
|---|---|---|---|---|---|---|
| Actual ee (%) | Calculated ee (%) | Absolute error (%) | | Actual ee (%) | Calculated ee (%) | Absolute error (%) |
| 87.0 | 84.1 | 2.9 | | 87.0 | 84.4 | 2.6 |
| 12.0 | 15.4 | 3.4 | | 76.0 | 76.7 | 0.7 |
| −26.0 | −23.5 | 2.5 | | 12.0 | 14.9 | 2.9 |
| −68.0 | −65.4 | 2.6 | | −26.0 | −27.3 | 1.3 |
| −89.0 | −87.0 | 2.0 | | −89.0 | −87.2 | 1.8 |

CD Measurements were performed at 3.0 10$^{-5}$ M in Et$_2$O.

Examples 11-25 introduce universal probes (including 2 and 34) that can be used for determination of the chirality and enantiomeric composition of many monoamines, diamines, amino alcohols, amino acids, and α-hydroxy acids. The enantioselective chemosensing is based on asymmetric transformation of the first kind of stereolabile zinc and boron binaphtholates that undergo prompt chiral amplification upon coordination of a chiral substrate. The central-to-axial chirality induction process can easily be measured by CD spectroscopy, and the sign and the amplitude of the Cotton effect can be correlated to the absolute configuration and ee of the samples tested. This sensing method is widely useful, fast, suitable for automated HTS applications, and it provides accurate results with small sample and solvent amounts.

Example 26—Synthetic Procedure

All reagents and solvents were commercially available and used without further purification. Reactions were carried out under inert and anhydrous conditions. NMR spectra were obtained at 400 MHz ($^1$H-NMR) using $(CD)_3SO$ and 100 MHz ($^{13}$C-NMR) using $CDCl_3$ as solvent and TMS as reference. Electrospray ionization mass spectra (ESI-MS, positive ion mode) were collected with samples dissolved in methanolic chloroform (1:1).

The compound numbers used in Examples 26-32 refer to the following compounds (where applicable, only one enantiomer is shown). Some of these compounds may be numbered differently in Examples 1-10 and/or Examples 11-25.

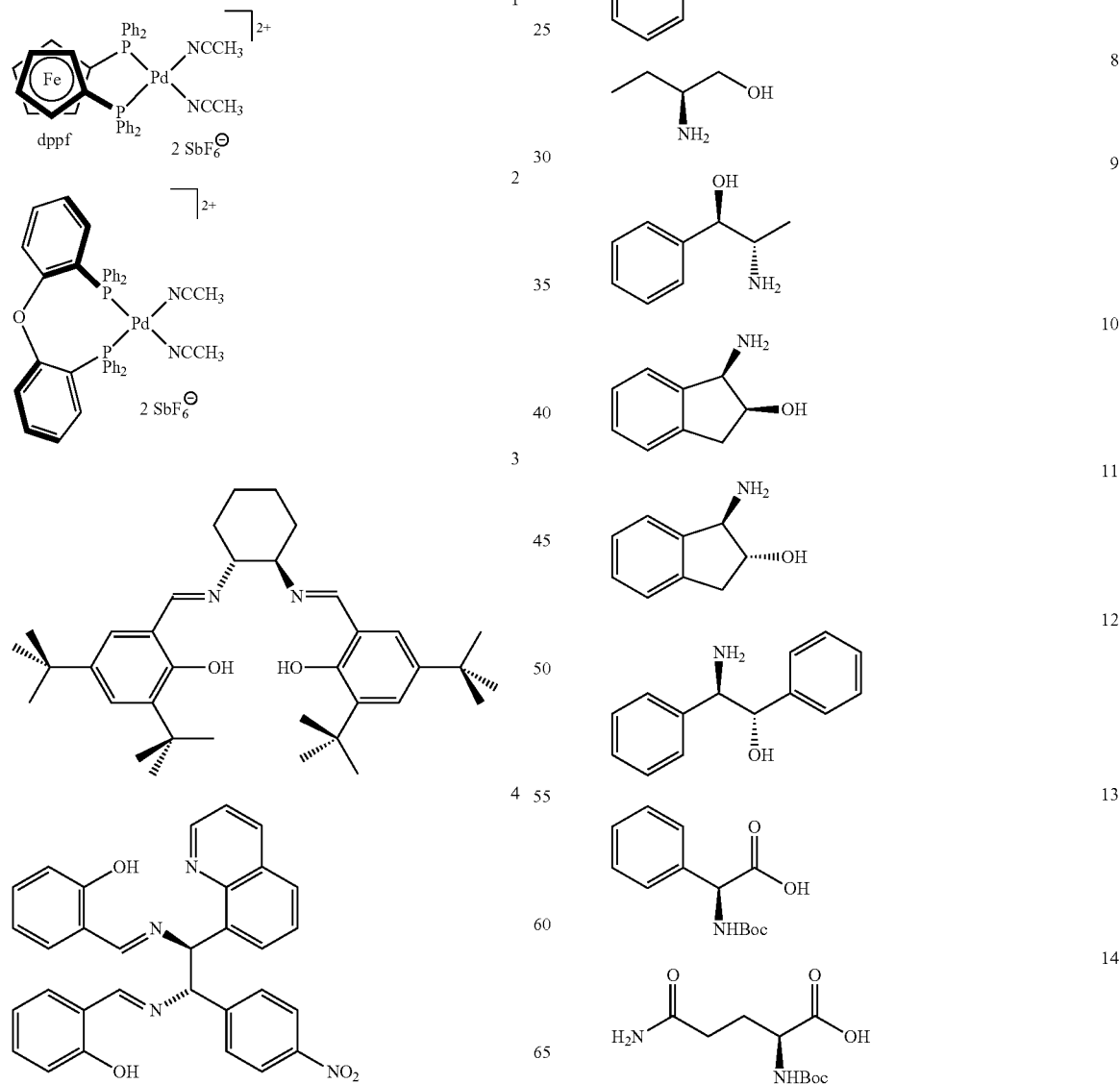

-continued

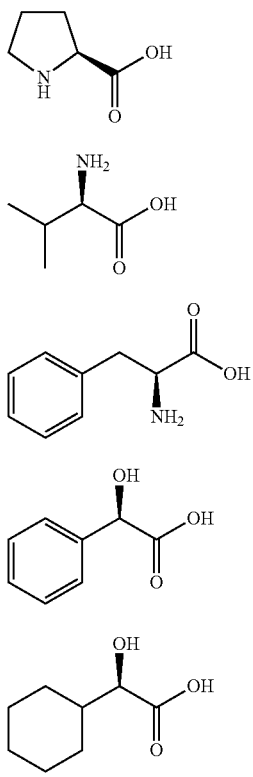

(Meso)salen ligand 5 was synthesized as shown in Scheme 12.

Scheme 12

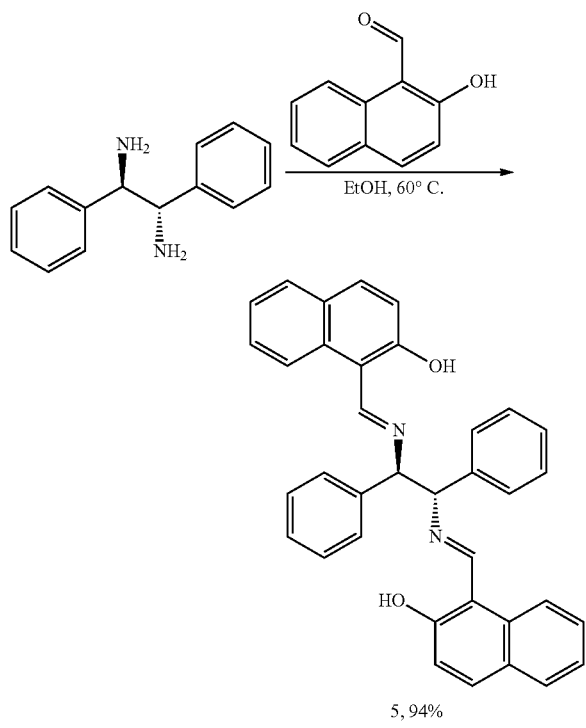

Figure 99A:
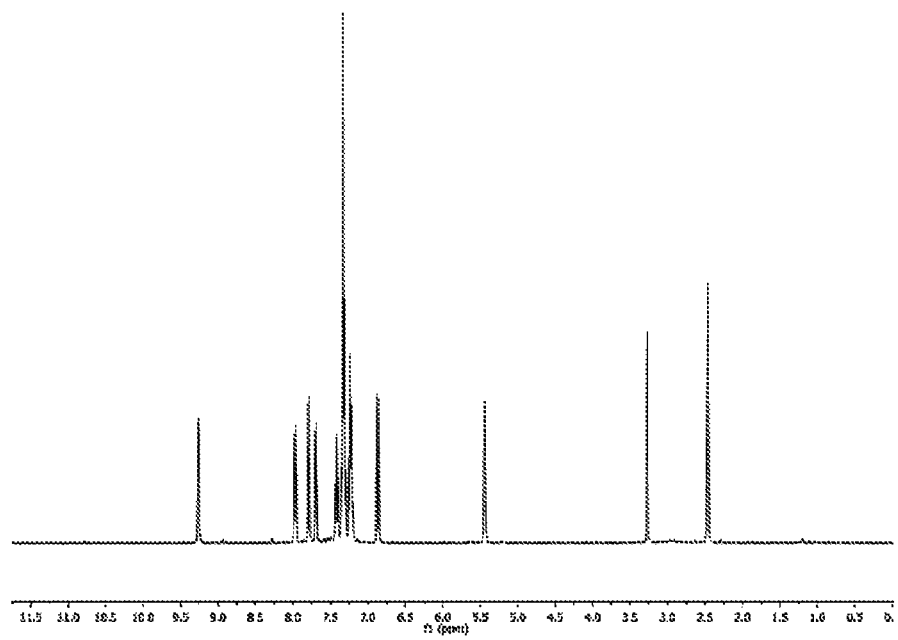
FIGS. 99A-B are the $^1$H NMR (FIG. 99A) and $^{13}$C NMR (FIG. 99B) spectra of 5 in $d_6$-DMSO and $CDCl_3$, respectively.
Figure 99B:
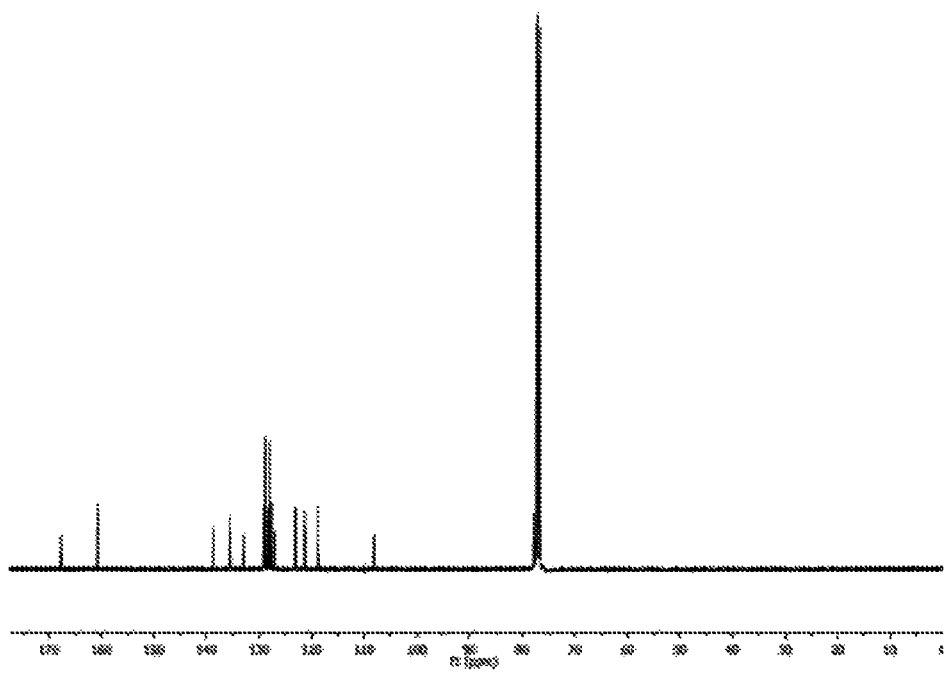

To a solution of meso 1,2-diphenylethylenediamine (51.67 mg, 0.24 mmol) in 3 mL of ethanol was added 1-(2-hydroxy) naphthaldehyde (85.42 mg, 0.50 mmol) and the solution was heated to 60° C. for 12 hours. The resulting mixture was allowed to cool to room temperature and 119.5 mg (0.23 mmol, 94% yield) of (meso)salen ligand 5 as a yellow solid was isolated with a centrifuge. $^1$H NMR (FIG. 99A): δ=9.26 (d, J=5.1 Hz, 2H), 7.97 (d, J=8.5 Hz, 2H), 7.79 (d, J=9.2 Hz, 2H), 7.70 (d, J=7.9 Hz, 2H), 7.42 (ddd, J=8.3, 7.0, 1.5 Hz, 2H), 7.29-7.36 (m, 8H), 7.19-7.26 (m, 4H), 6.87 (d, J=9.2 Hz, 2H), 5.44 (s, 2H). $^{13}$C NMR (FIG. 99B): δ=167.6, 160.6, 138.6, 135.5, 132.9, 129.0, 128.8, 128.3, 127.9, 127.6, 127.1, 123.1, 121.3, 118.7, 108.1, 77.7. Anal. Calcd. for $C_{36}H_{28}N_2O_2$: C, 83.05; H, 5.42; N, 5.38. Found: C, 83.31; H, 5.49; N, 5.59. mp>200° C. (decomp.).

Example 27—CD Sensing Experiments Generally

Figure 100:
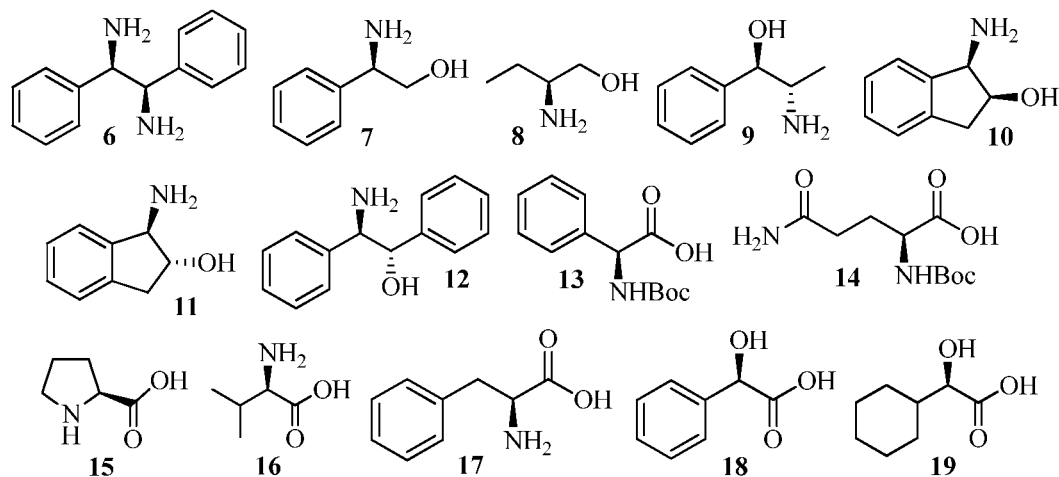
FIG. 100 shows the structures of substrates 6-19 (only one enantiomer shown).
Figure 101:
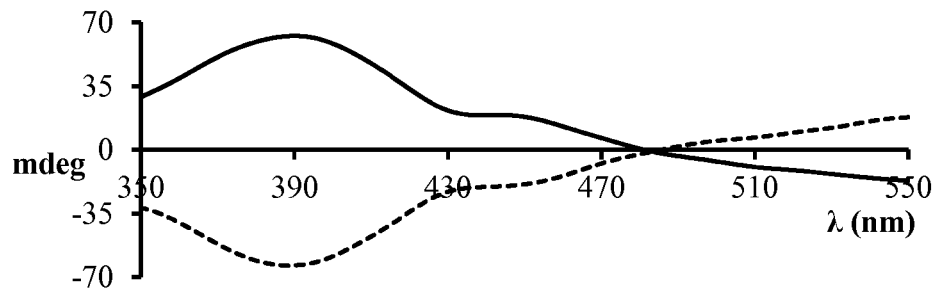
FIG. 101 is the CD spectra of (1R,2R)-6 (solid line) and (1S,2S)-6 (dashed line) with (salen 5)Co(III). All measurements were performed at 2.6×10-4 M in chloroform.

The Utility of the Salen Derived Cobalt Complex for Enantioselective CD Sensing was tested with substrates 6-19 (FIG. 100). None of the analytes tested was CD active at the wavelength of interest under the conditions specified below in the absence of 5.

Example 28—CD Sensing of Amines and Amino Alcohols

To a solution of 5 (0.03 M, 4.3 mL) in anhydrous CHCl$_3$ was added 268 μL, of a tetrabutylammonium hydroxide (TBAOH) solution (1.0 M in methanol). A solution of Co(NO$_3$)$_2$.6H$_2$O (0.31 M) in anhydrous THF was prepared and a portion of 432 μL was added to the solution containing 5 and TBAOH, thus generating 5.0 mL of a sensor stock solution. Solutions of substrates 6-9 and 12 (0.04 M in anhydrous CHCl$_3$), and 10 and 11 (0.04 M in anhydrous MeOH) were prepared. Then, 250 μL of the stock solution and 335 μL of a substrate solution were combined and diluted to 1.0 mL with anhydrous CHCl$_3$. Dioxygen was bubbled through this solution until all the solvent was evaporated. The residue was dissolved in anhydrous CHCl$_3$ to afford a concentration of 2.6×10$^{-4}$M. The CD spectra were collected with a standard sensitivity of 100 mdeg, a data pitch of 0.5 nm, a bandwidth of 1 nm, a scanning speed of 500 nm s$^{-1}$ and a response of 0.5 s using a quartz cuvette (1 cm path length). The data were baseline corrected and smoothed using a binomial equation (see FIGS. 101-107). It is noteworthy that the same results were obtained when the treatment with dioxygen was repeated 3 times and when 5 equivalents of the sensing target were added. Control experiments with 6-12 (2.6×10$^{-4}$ M) in CHCl$_3$ in the absence of 5 did not show any CD signal at the wavelengths of interest.

Example 29—CD Sensing of Amino Acids and Carboxylic Acids

To a solution of 5 (0.03 M, 4.3 mL) in anhydrous CHCl$_3$ was added 268 μL of a tetrabutylammonium hydroxide (TBAOH) solution (1.0 M in methanol). A solution of Co(NO$_3$)$_2$.6H$_2$O (0.31 M) in anhydrous THF was prepared and a portion of 432 μL was added to the solution containing 5 and TBAOH, thus generating 5.0 mL of a sensor stock solution. Solutions of substrates 13-19 (0.04 M in anhydrous MeOH) were prepared and 44.1 μL tetrabutylammonium hydroxide (1.0 M in MeOH) was added to the substrate solutions. Then, 250 μL of the stock solution and 335 μL of a substrate solution were combined and diluted to 1.0 mL with anhydrous CHCl$_3$. Dioxygen was bubbled through this solution until all the solvent was evaporated. The residue was dissolved in anhydrous $CHCl_3$ to afford a concentration of $2.6 \times 10^{-4}$ M. The CD spectra were collected with a standard sensitivity of 100 mdeg, a data pitch of 0.5 nm, a bandwidth of 1 nm, a scanning speed of 500 nm s$^{-1}$, and a response of 0.5 s using a quartz cuvette (1 cm path length). The data were baseline corrected and smoothed using a binomial equation (see FIGS. 108-114). It is noteworthy that the same results were obtained when the treatment with dioxygen was repeated 3 times and when 5 equivalents of the sensing target were added. Control experiments with 13-19 ($2.6 \times 10^{-4}$ M) in $CHCl_3$ in the absence of 5 did not show any CD signal at the wavelengths of interest.

Example 30—Quantitative ee Analysis

Figure 115:
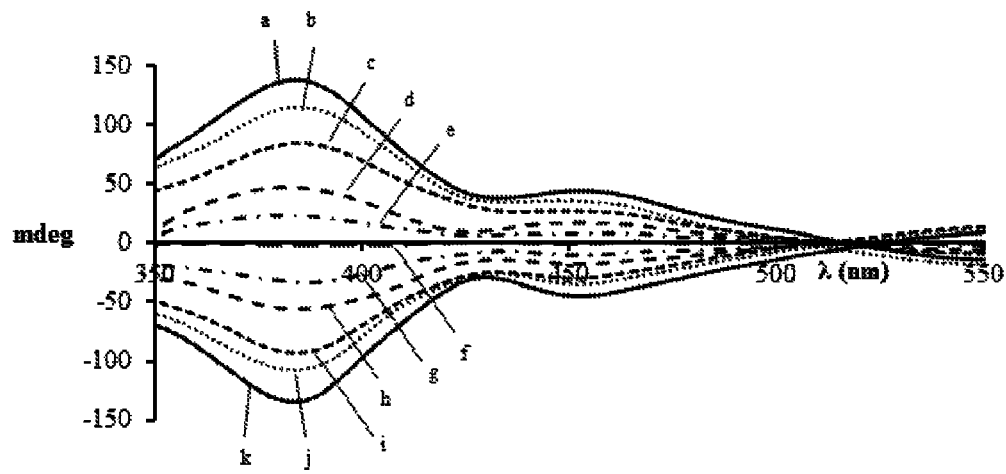
FIG. 115 is the CD spectra obtained with the salen cobalt complex and scalemic samples of amino alcohol 10. All measurements were performed at $2.6 \times 10^{-4}$M in chloroform. a: +100; b: +80; c: +60; d: +40; e: +20; f: 0; g: −20; h: −40; i: −60; j: −80; k: −100.
Figure 116:
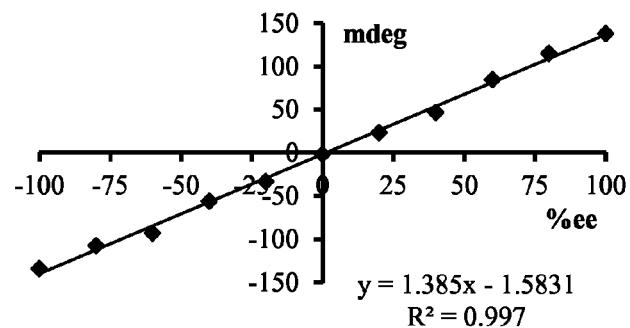
FIG. 116 is a plot showing the linear relationship between the CD amplitudes at 385 nm and the enantiomeric excess of amino alcohol 10 using the CD readout of 10 at 385 nm. All measurements were performed at $2.6 \times 10^{-4}$M in chloroform.

Stock solutions of the salen cobalt complex (0.0046 M) and 10 (0.05 mmol) with varying enantiomeric composition (+100, +80, +60, +40, +20, 0, −20, −40, −60, −80, −100 ee) were prepared as described above. Within 5 minutes, CD analysis was carried out with samples having a concentration of $2.6 \times 10^{-4}$ M in anhydrous chloroform (FIG. 115). The Cotton effect amplitudes at 385 nm were plotted against the enantiomeric excess of 10 (FIG. 116). The calibration curve was used to calculate ee's of various nonracemic samples of 10. See Table 8.

TABLE 8

Sensing of the % ee of amino alcohol 10.

| Actual % ee | Calculated % ee | Absolute error (%) |
|---|---|---|
| 87.0 | 93.2 | 6.2 |
| 76.0 | 74.3 | 1.7 |
| 12.0 | 7.2 | 4.8 |
| −26.0 | −25.4 | 0.6 |
| −68.0 | −72.8 | 4.2 |
| −89.0 | −88.7 | 0.3 |

CD measurements were performed at $2.6 \times 10^{-4}$ M in chloroform.

Example 31—Solvent and Temperature Effect

The same procedure as described above was repeated and the final solutions were prepared using anhydrous ACN, EtOH, and THF as solvent. All CD measurements were conducted at $3.0 \times 10^{-4}$ M concentration. See FIGS. 117 and 118.

Example 32—MS Analysis of the Complex Formation

A solution of 5, $Co(NO_3)_2$ and a substrate in anhydrous $CHCl_3$ (0.0038 M) was prepared as described above. The solution was oxidized with $O_2$ until the solvent was evaporated. Then, 1.0 mL of anhydrous $CHCl_3$ was added and 26 μl of the prepared solution was diluted to 1.0 mL ($10^{-4}$ M) with anhydrous $CHCl_3$:MeOH (1:1 v/v). Analysis by electrospray mass spectrometry (positive ion mode) showed the presence of a cobalt complex containing one equivalent of 5 and one equivalent of the substrates 6 and 10, respectively. See FIGS. 119 and 120.

Both CD and MS analysis showed that the initial (salen)(substrate)Co(II) complex is easily oxidized upon exposure to air. Quantitative oxidation is accomplished by bubbling dioxygen into the sample solution at room temperature for approximately 5 minutes until the solvent is evaporated.

Discussion of Examples 26-32

Examples 1-25 describe the design of several stereodynamic axially chiral probes and the application of readily available tropos ligand-derived boron, zinc, and palladium complexes to chiroptical ee sensing (Zhang & Wolf, Chem. Commun. 49:7010-12 (2013); Bentley et al., J. Am. Chem. Soc. 135:18052-55 (2013), which are hereby incorporated by reference in their entirety). The underlying idea of chirality sensing with metal complexes carrying a tropos ligand is illustrated in Scheme 13. In absence of a nonracemic substrate, the (dppf)palladium(II) complex 1 or its 2,2'-bis(diphenylphosphino)diphenyl ether analogue 2 exists as a CD-silent racemic mixture of rapidly interconverting enantiomers. Coordination of a chiral compound then induces a conformational bias in the tropos ligand and an asymmetric transformation of the first kind. The chiral amplification generates a strong Cotton effect originating from the chromophoric dppf moiety, which can be correlated to the absolute configuration and enantiomeric excess of the analyte. It was hypothesized that this concept can also be exploited with a metal complex carrying a chromophoric achiral ligand, which in principle can adopt a CD-active conformation upon coordination of a chiral substrate.

Scheme 13

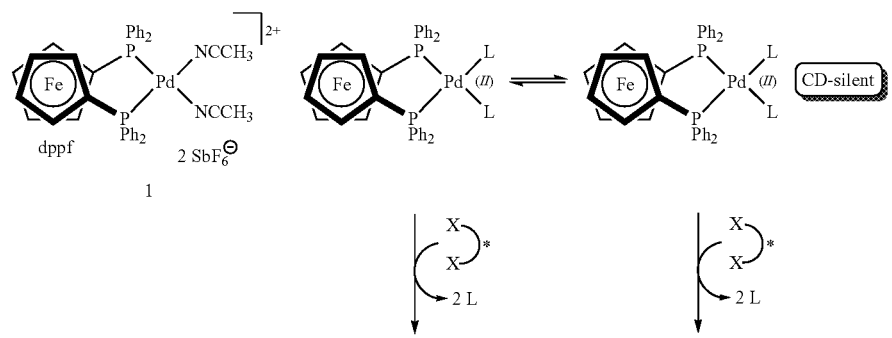

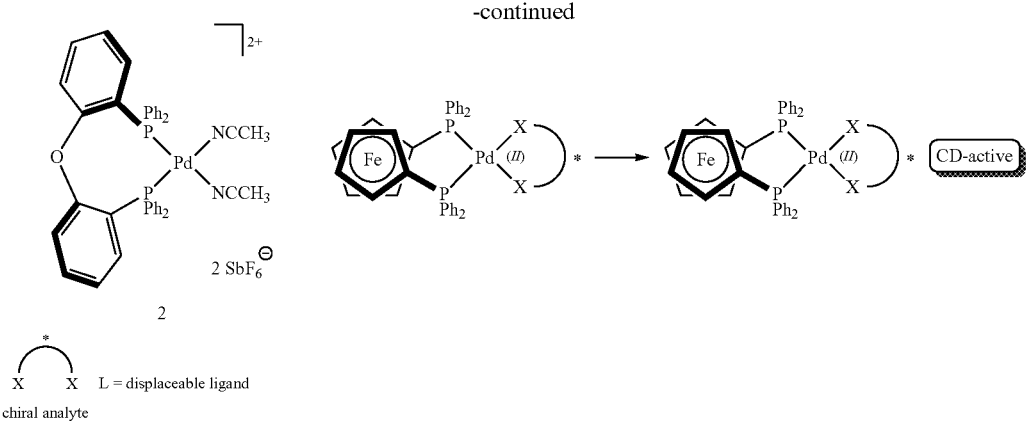

X X L = displaceable ligand
chiral analyte

Examples 26-32 introduce a readily available cobalt complex carrying meso-salen ligand 5 for enantioselective sensing of chiral substrates. This approach is based on substrate-to-ligand chirality induction resulting in a distinctive and quantifiable circular dichroism signal at high wavelengths.

Figure 121:
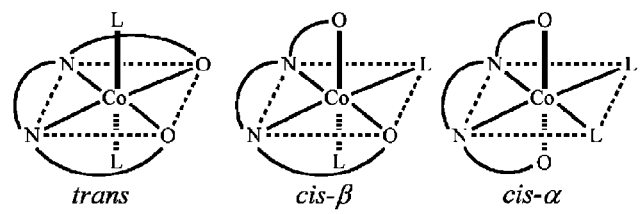

It has been established that cobalt(III) complexes carrying a tetradentate salen ligand typically exhibit a square pyramidal structure or, when an additional donor ligand is present, an octahedral coordination sphere. Octahedral (salen)cobalt(III) complexes can occur in three isomeric forms, albeit di- and trinuclear species have also been reported (Welby et al., Inorg. Chim. Acta 362:1405-11 (2009), which is hereby incorporated by reference in its entirety). The structural flexibility of the salen ligand enables it to accommodate either a facial or a meridional metal chelation (FIG. 121). The most common trans-configuration in which the salen ligand resides in the meridional plane is the predominant species when monodentate ligands occupy the axial positions (Zhang et al., Polyhedron 22:1535-45 (2003); Iranmanesh et al., Inorg. Chim. Acta 395:81-88 (2013), which are hereby incorporated by reference in their entirety). The cis-α and in particular the cis-β configuration are favored when bidentate ligands are present (Cyriac et al., Dalton Trans. 41:1444-47 (2012); Elmas et al., Green Chem. 15:1356-60 (2013), which are hereby incorporated by reference in their entirety).

It was therefore expected that coordination of a bidentate chiral compound such as a diamine or amino alcohol to a (meso-5)cobalt complex would force the salen ligand into a chiral, CD-active conformation. This substrate-to-salen chiral induction process would generate a cobalt complex exhibiting a characteristic chiroptical signal. Because the sign and amplitude of the CD signal would be dependent on the enantiopurity of the substrate added, the chirality and ee of the latter could be determined by a simple CD measurement. Important prerequisites for practical chiroptical sensing include the generation of a distinctive CD readout at high wavelengths to avoid interference with chiral impurities, effective chiral amplification and a strong sensor CD response to allow accurate ee measurements at low sensor and substrate concentrations, elimination of cumbersome purification steps, and fast in-situ analysis based on a simple mix-and-measure protocol. In this regard, it is important to note that cobalt(II) complexes typically undergo rapid ligand exchange while cobalt(III) analogues are known to be rather kinetically inert. To address the need for time-efficient chirality sensing, it was decided to resort to Co(II) nitrate to first establish the coordination of the salen and the substrate to the metal center followed by fast oxidation with air to generate an air-stable Co(III) complex for CD analysis.

Figure 102:
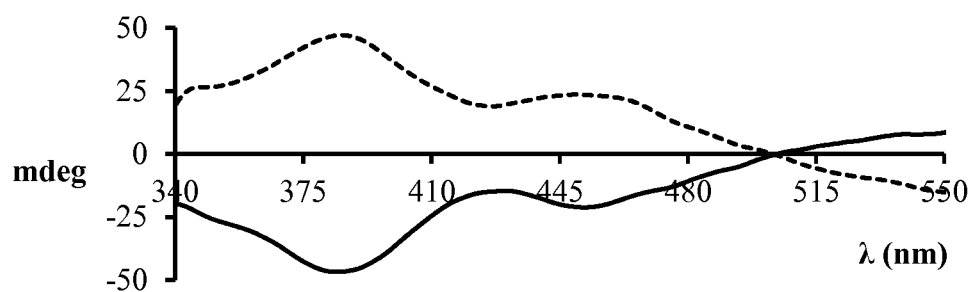
FIG. 102 is the CD spectra of (R)-7 (solid line) and (S)-7 (dashed line) with (salen 5)Co(III). All measurements were performed at 2.6×10-4 M in chloroform.
Figure 103:
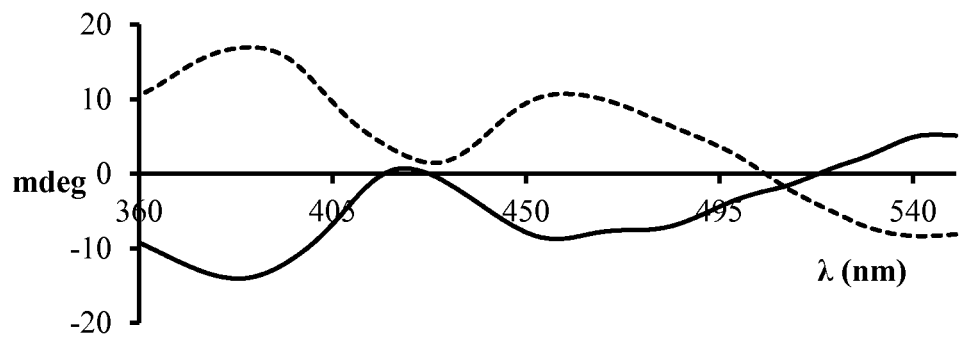
FIG. 103 is the CD spectra of (R)-8 (solid line) and (S)-8 (dashed line) with (salen 5)Co(III).
Figure 104:
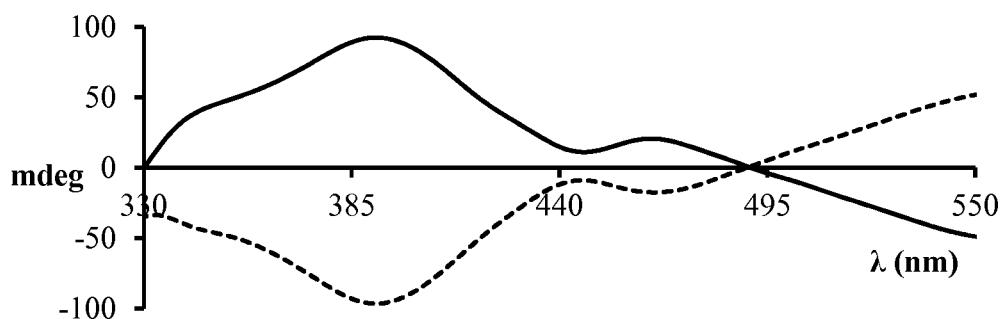
FIG. 104 is the CD spectra of (1S,2R)-9 (solid line) and (1R,2S)-9 (dashed line) with (salen 5)Co(III).
Figure 105:
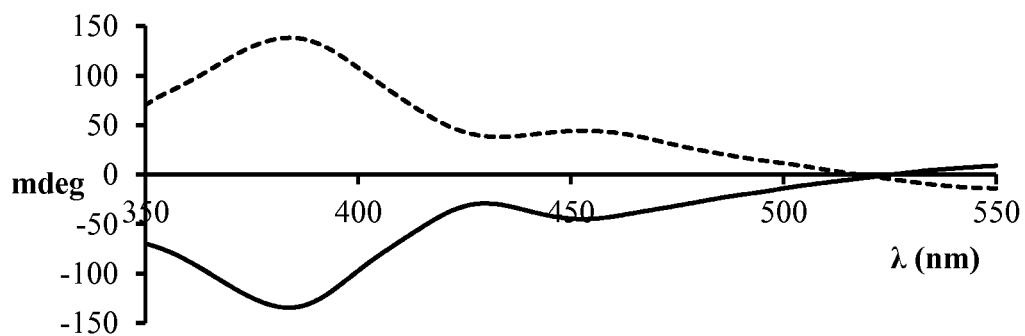
FIG. 105 is the CD spectra of (1S,2R)-10 (solid line) and (1R,2S)-10 (dashed line) with (salen 5)Co(III).
Figure 106:
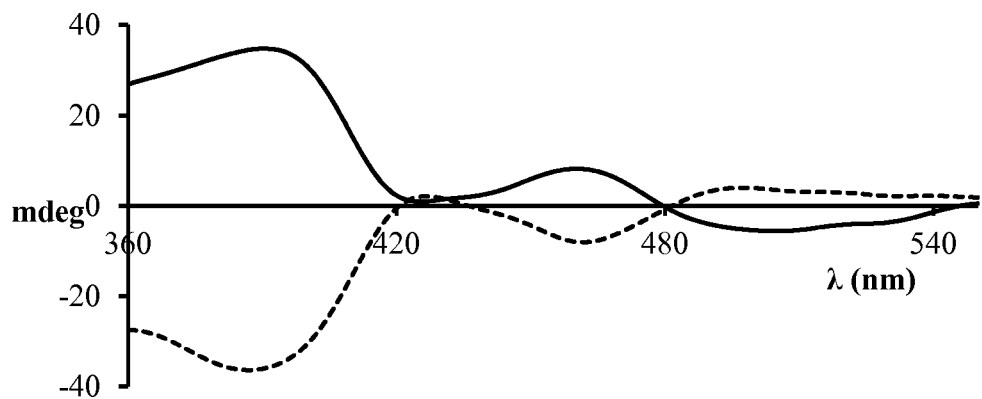
FIG. 106 is the CD spectra of (1R,2R)-11 (solid line) and (1S,2S)-11 (dashed line) with (salen 5)Co(III).
Figure 107:
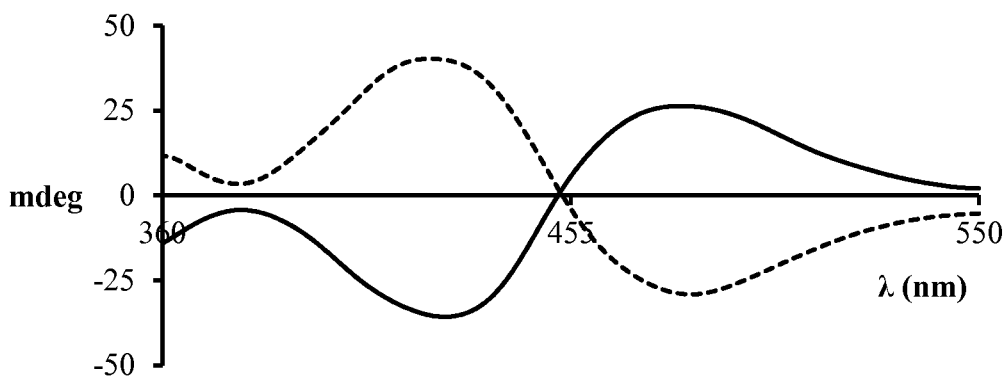
FIG. 107 is the CD spectra of (1S,2R)-12 (solid line) and (1R,2S)-12 (dashed line) with (salen 5)Co(III).
Figure 108:
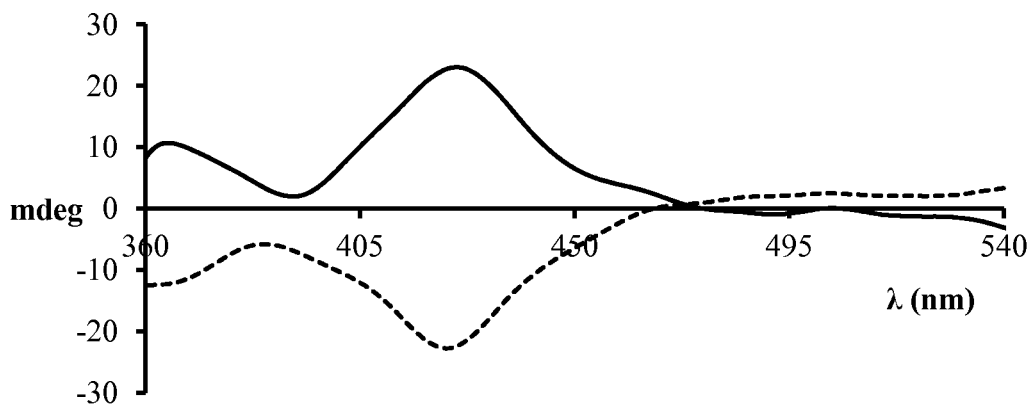
FIG. 108 is the CD spectra of (R)-13 (solid line) and (S)-13 (dashed line) with (salen 5)Co(III).
Figure 109:
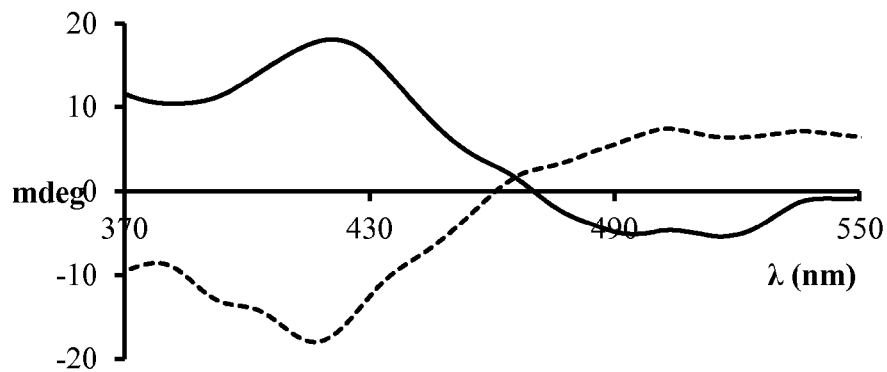
FIG. 109 is the CD spectra of (R)-14 (solid line) and (S)-14 (dashed line) with (salen 5)Co(III).
Figure 110:
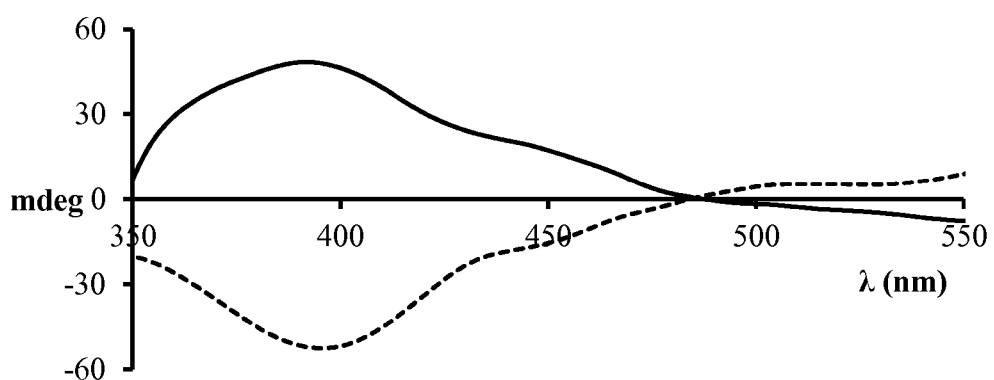
FIG. 110 is the CD spectra of (R)-15 (solid line) and (S)-15 (dashed line) with (salen 5)Co(III).
Figure 111:
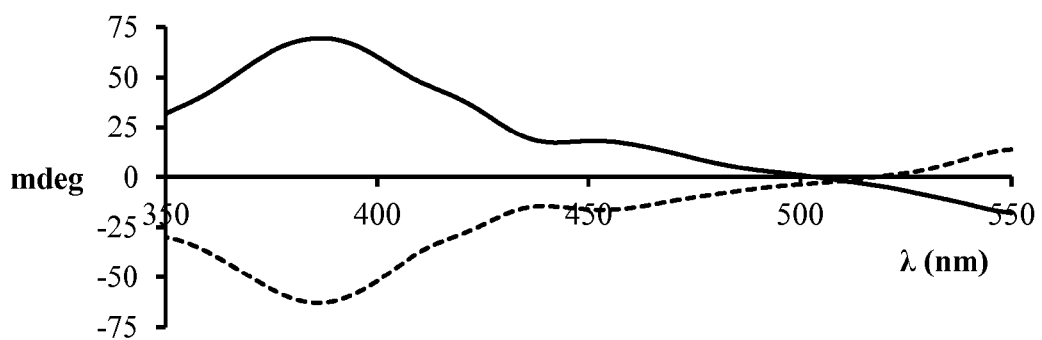
FIG. 111 is the CD spectra of (R)-16 (solid line) and (S)-16 (dashed line) with (salen 5)Co(III).
Figure 112:
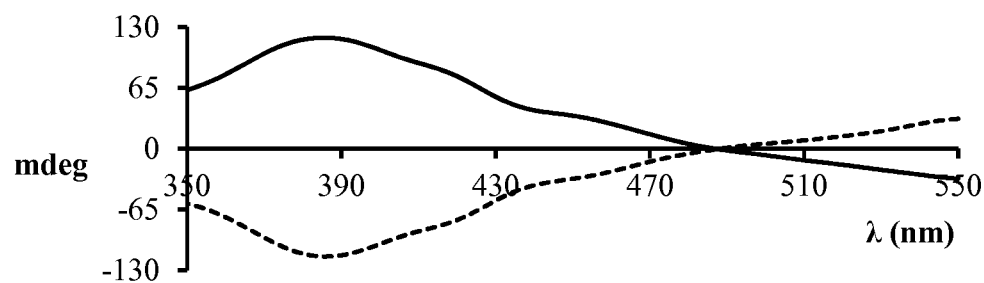
FIG. 112 is the CD spectra of (R)-17 (solid line) and (S)-17 (dashed line) with (salen 5)Co(III). All measurements were performed at $2.6 \times 10^{-4}$M in chloroform.
Figure 113:
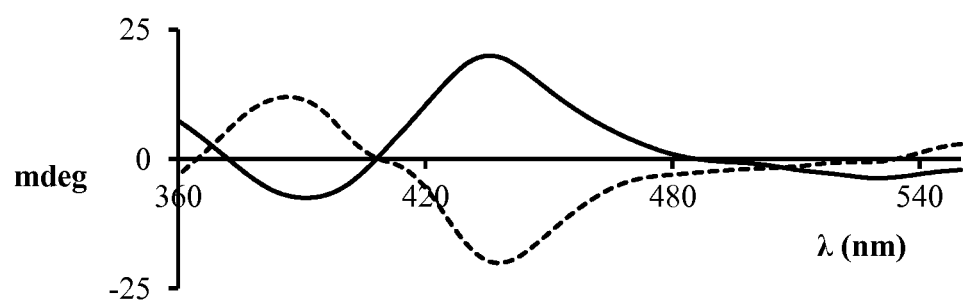
FIG. 113 is the CD spectra of (R)-18 (solid line) and (S)-18 (dashed line) with (salen 5)Co(III). All measurements were performed at $2.6 \times 10^{-4}$M in chloroform.
Figure 114:
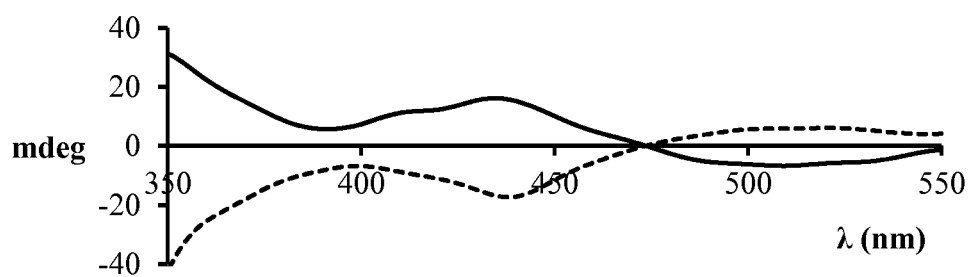
FIG. 114 is the CD spectra of (R)-19 (solid line) and (S)-19 (dashed line) with (salen 5)Co(III).
Figure 119:
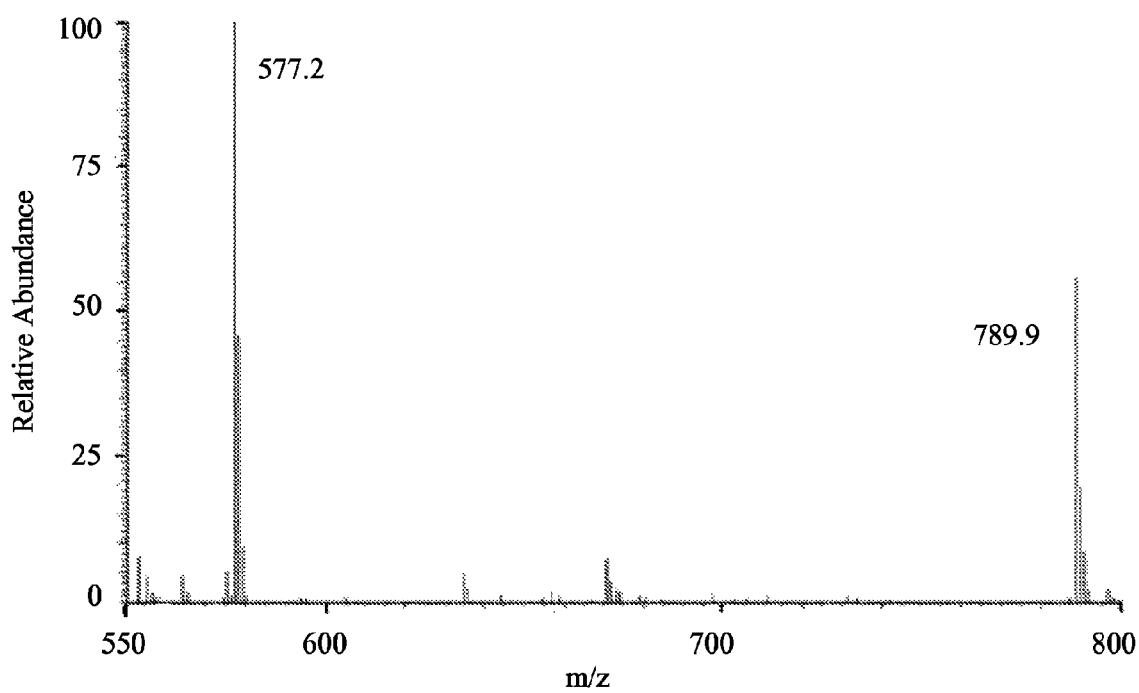
Figure 120:
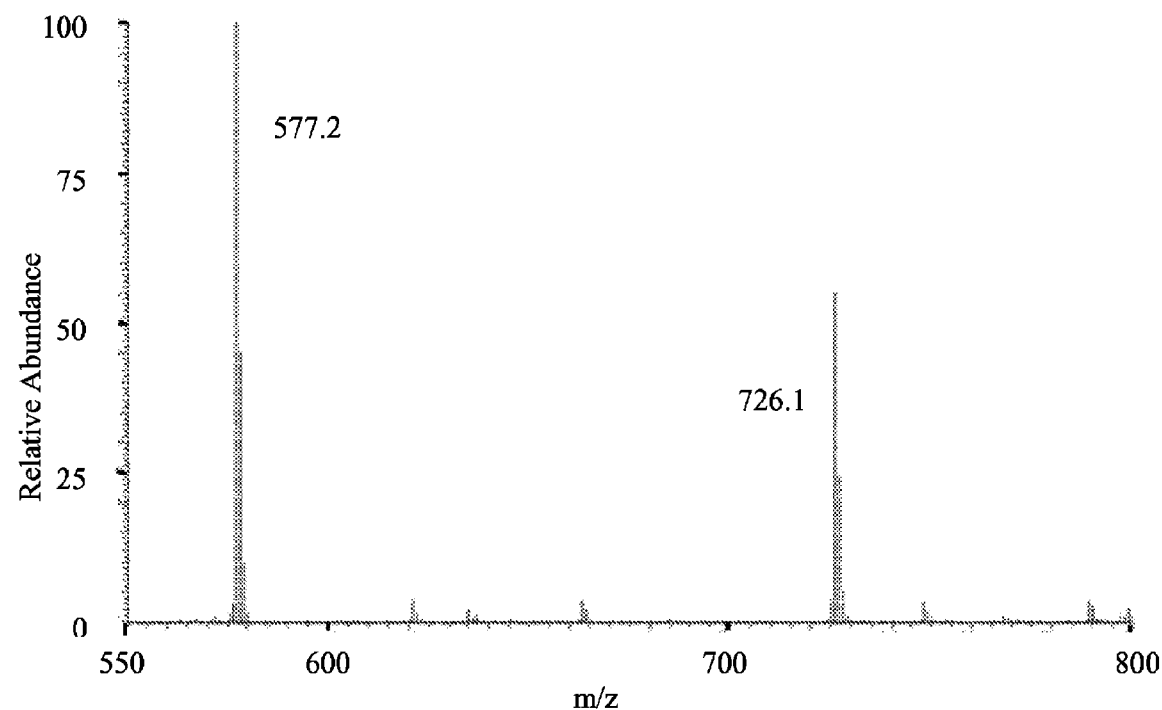

The salen ligand 5 was synthesized in one step from meso-1,2-diphenylethylenediamine and 1-naphthaldehyde in 94% yield (see Example 26, supra). Based on the considerations outlined above, a variety of aliphatic and aromatic sensing targets were selected, and diamine 6, amino alcohols 7-12, amino acids 13-17, and α-hydroxy acids 18 and 19 (FIG. 100) were tested to explore the potential and general utility of the (salen 5)Co probe. Initial screening experiments showed that mixing of Co(II) nitrate, meso-5, two equivalents of tetrabutylammonium hydroxide (TBAOH), and slight excess of a chiral diamine or amino alcohol in chloroform followed by short treatment with dioxygen affords a highly CD active complex. Strong Cotton effects were measured in all cases with highly diluted samples (2.6 $10^{-4}$ M in chloroform), and MS analysis of the solutions obtained with diamine 6 and aminoindanol 10 confirmed the formation of a stoichiometric [(salen)(substrate)Co(III)]$^+$ complex (FIGS. 119 and 120; see Example 32, supra). Coordination of the (R,R)-enantiomer of diamine 6 to the cobalt probe results in a positive CD maximum at 390 nm (FIG. 101) while (R)-7 and (R)-8 generate a negative CD response at approximately 385 nm (FIGS. 102 and 103). The chiroptical sensing of amino alcohols 9-12 exhibiting two chiral centers and either conformationally flexible or rigid cyclic structures affords distinct Cotton effects and the CD responses appear to be substrate specific (FIGS. 104-107; see Example 28, supra).

The chirality sensing of amino acids and α-hydroxy acids 13-19 in the presence of an additional equivalent of TBAOH gave equally strong Cotton effects (FIGS. 108-114; see Example 29, supra). The protected and unprotected amino acids with (R)-configuration yield a positive CD maximum at either 390 or 420 nm while the (S)-enantiomers generate a negative CD response with the same amplitude (see FIGS. 108-112 and entries 8-12 in Table 9). The results obtained with the α-hydroxy acids 18 and 19 reveal the same trend (see FIGS. 113 and 119 and entries 13 and 14 in Table 9), and this underscores the possibility of fast determination of the absolute configuration of chiral compounds by a simple CD sensing experiment.

TABLE 9

Chiroptical Sensing of Compounds 6-19.

| Entry | Substrate | $\Delta_{max}$ (mdeg)$^a$ | $\lambda_{max}$ |
|---|---|---|---|
| 1 | (1R,2R)-6 | +63 | 390 |
|   | (1S,2S)-6 | 63 |  |
| 2 | (R)-7 | −47 | 386 |
|   | (S)-7 | +47 |  |
| 3 | (R)-8 | −14 | 384 |
|   | (S)-8 | +16 |  |
| 4 | (1S,2R)-9 | +92 | 392 |
|   | (1R,2S)-9 | −96 |  |
| 5 | (1S,2R)-10 | −134 | 384 |
|   | (1R,2S)-10 | +138 |  |
| 6 | (1R,2R)-11 | +34 | 388 |
|   | (1S,2S)-11 | −36 |  |
| 7 | (1S,2R)-12 | −36 | 426 |
|   | (1R,2S)-12 | +40 |  |
| 8 | (R)-13 | +23 | 426 |
|   | (S)-13 | −22 |  |
| 9 | (R)-14 | +18 | 419 |
|   | (S)-14 | −18 |  |
| 10 | (R)-15 | +48 | 391 |
|    | (S)-15 | −51 |  |
| 11 | (R)-16 | +69 | 387 |
|    | (S)-16 | −63 |  |
| 12 | (R)-17 | +118 | 385 |
|    | (S)-17 | −115 |  |
| 13 | (R)-18 | +20 | 438 |
|    | (S)-18 | −20 |  |
| 14 | (R)-19 | +17 | 435 |
|    | (S)-19 | −16 |  |

$^a$All CD measurements were performed at 2.6 × 10$^{−4}$ M in CHCl$_3$.

Figure 117:
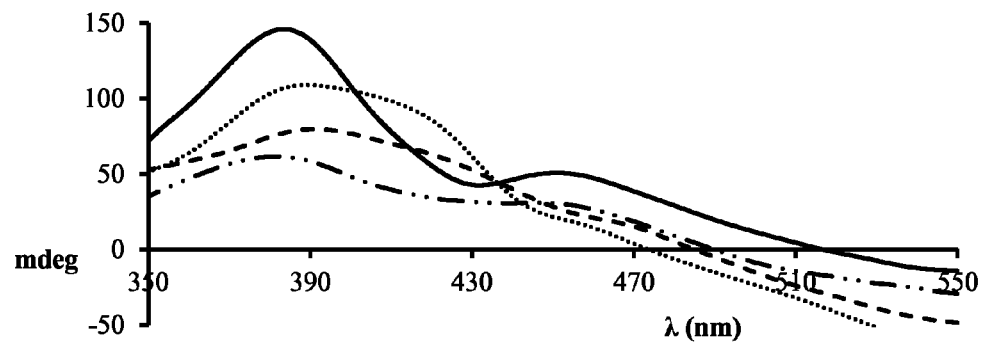
FIG. 117 is the CD spectra obtained using (salen 5)Co(III) in the presence of cis-(1R,2S)-aminoindanol 10 in $CHCl_3$ (solid line), acetonitrile (dashed-double dotted line), EtOH (dotted line), and THF (dashed line). All measurements were performed at $3.0 \times 10^{-4}$M in chloroform.
Figure 118:
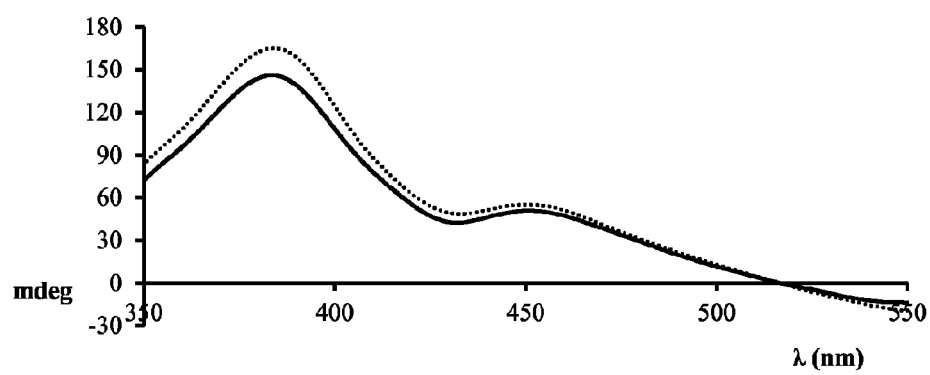
FIG. 118 is the CD spectra obtained using (salen 5)Co(III) and (1R,2S)-10 at room temperature (solid line) and at 5° C. (dotted line). All measurements were performed at $3.0 \times 10^{-4}$M in chloroform.

The CD sensing can be conducted in a wide range of solvents. Comparison of the CD response of the achiral cobalt probe to cis-(1R,2S)-aminoindanol in chloroform, acetonitrile, ethanol, and tetrahydrofuran shows that the chiral amplification process is most effective in chloroform (FIGS. 117 and 118). However, strong induced Cotton effects were also measured in the other solvents. Although all CD measurements can be conveniently performed at room temperature under air, cooling of the sample to 5° C. slightly increases the CD signal.

Finally, the suitability of the chemosensor for the determination of the enantiomeric composition of chiral compounds was investigated. CD sensing of nonracemic samples of cis-(1R,2S)-aminoindanol 10 revealed that the Co complex gives a linear chiroptical response with regard to the substrate ee (FIGS. 115 and 116). Linear regression analysis was then used to measure the enantiopurity of six samples covering a wide ee range (see supra Example 30, Table 8). The chemsosensing results are generally in good agreement with the actual data and of sufficient accuracy for high-throughput screening applications.

Examples 26-32 show the potential of chirality sensing using a meso-ligand derived metal complex as probe. The imprinting of the substrate chirality onto the (salen 5)cobalt (III) complex generates a strong CD response at high wavelengths. This can be used to determine the absolute configuration and ee of bidentate substrates, which has been demonstrated with a variety of diamines, amino alcohols, amino acids, and α-hydroxy acids. Attractive features of this sensing approach include the use of a readily available, inexpensive probe, a wide application scope, a practical and time-efficient mix-and-measure protocol, reduced production of solvent waste compared to HPLC or GC ee analysis, and accurate results with small sample amounts. The general scope, practicality, and accuracy of this assay are similar to other chiroptical sensing methods with stereodynamic metal complexes.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An analytical method comprising:

providing a sample potentially containing a chiral analyte that can exist in stereoisomeric forms;

providing a racemic mixture of a probe having the formula $A_m$-$MR_n$—$Y_o$, wherein:

each A is independently a chiral stereodynamic ligand that undergoes rapid stereoisomeric interconversion at room temperature, M is a metal, each R is independently a metal coordinating ligand, each Y is independently a displaceable ligand, m is an integer from 1 to 6, and n and o are each independently an integer from 0 to 6, wherein the sum of m, n, and o is from 1 to 6;

contacting the sample with the racemic mixture under conditions effective to form probe-analyte complexes; and determining, based on the probe-analyte complexes that form, the stereoisomeric excess of the analyte in the sample and/or the concentration of the analyte in the sample.

2. The analytical method according to claim 1, wherein A is selected from the group consisting of 1,1'-bis(diphenylphosphino)ferrocene (DPPF), 2,2'-bis(diphenylphosphino) diphenyl ether (BDPDE), 2,2'-bis(diphenylphosphino)-1,1'-biphenyl (BIPHEP), BIPHOS, 2,2'-diaminobiphenyls, 2,2'-dihydroxybiphenyls, and analogues of each of the preceding compounds.

3. The analytical method according to claim 1, wherein M is selected from the group consisting of palladium, magnesium, boron, aluminum, copper, zinc, iron, cobalt, nickel, platinum, gold, titanium, vanadium, manganese, chromium and cobalt.

4. The analytical method according to claim 3, wherein M is Pd(II).

5. The analytical method according to claim 1, wherein each Y is independently selected from the group consisting of H, OH, NH$_2$, NCCH$_3$, CF$_3$SO$_3^-$, alkyls, alkenyls, alkynyls, halogens, halides, halogen-containing anions, haloalkyls, haloalkenyls, hydroxyls, alcohols, hydrides, carbonyls, aldehydes, carbonate esters, carboxylates, carboxyls, esters, alkoxyls, alkoxides, ethers, hemiacetals, hemiketals, acetals, ketals, orthoesters, orthocarbonate esters, amides, amines, imines, imides, azides, diimides, cyanates, cyanides, nitrates, nitriles, nitrites, nitrosos, pyridyls, thiols, thioethers, disulfides, sulfoxides, sulfones, sulfonates, thiocyanates, thiones, phosphines, phosphoric acids, phosphates, aryls, heteroaryls, arylalkyls, heterocycles, cycloalkyls, cycloalkenyls, and acyls.

6. The analytical method according to claim 1, wherein the probe is selected from the group consisting of

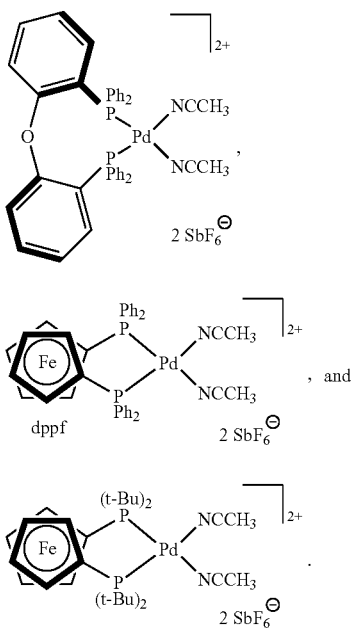

7. The analytical method according to claim 1, wherein the analyte is a compound selected from the group consisting of amines, alcohols, amino alcohols, carboxylic acids, amino acids, thiols, aldehydes, ketones, amides, esters, and any combination thereof.

8. The analytical method according to claim 7, wherein the analyte is a diamine or an amino alcohol.

9. The analytical method according to claim 1, wherein the stereoisomeric excess of the probe-analyte complexes is determined.

10. The analytical method according to claim 9, wherein the analyte is a reaction product and the stereoselectivity of the reaction is determined by determining the stereoisomeric excess of the analyte.

11. The analytical method according to claim 1, wherein the concentration of the probe-analyte complexes is determined.

12. The analytical method according to claim 11, wherein the analyte is a reaction product and the yield of the reaction is determined by determining the concentration of the analyte.

13. The analytical method according to claim 1, wherein the stereoisomeric excess of the probe-analyte complexes and the concentration of the probe-analyte complexes are both determined.

14. The analytical method according to claim 13 further comprising:

determining the individual concentration of any particular stereoisomers present in the sample based on the determined concentration of the analyte and the determined stereoisomeric excess.

* * * * *